US007037716B2

(12) United States Patent  
Vogels et al.

(10) Patent No.: US 7,037,716 B2  
(45) Date of Patent: May 2, 2006

(54) PACKAGING SYSTEMS FOR HUMAN RECOMBINANT ADENOVIRUS TO BE USED IN GENE THERAPY

(75) Inventors: Ronald Vogels, Linschoten (NL); Abraham Bout, Moerkapelle (NL)

(73) Assignee: Crucell Holland B.V., Leiden (NL)

( * ) Notice: Subject to any disclaimer, the term of this patent is extended or adjusted under 35 U.S.C. 154(b) by 249 days.

(21) Appl. No.: 10/396,548

(22) Filed: Mar. 25, 2003

(65) Prior Publication Data

US 2005/0074885 A1    Apr. 7, 2005

Related U.S. Application Data

(60) Continuation of application No. 09/900,062, filed on Jul. 6, 2001, now abandoned, which is a division of application No. 09/065,752, filed on Apr. 24, 1998, now Pat. No. 6,670,188.

(51) Int. Cl.  
C12N 15/00    (2006.01)

(52) U.S. Cl. ............... 435/320.1; 536/23.1; 536/24.1; 536/23.72

(58) Field of Classification Search ............ 435/320.1, 435/69.1, 235.1; 536/23.1, 24.1, 23.72  
See application file for complete search history.

(56) References Cited

U.S. PATENT DOCUMENTS

| | | | |
|---|---|---|---|
| 4,405,712 | A | 9/1983 | Vande Woude et al. |
| 4,497,796 | A | 2/1985 | Salser et al. |
| 4,727,028 | A | 2/1988 | Santerre et al. |
| 4,740,463 | A | 4/1988 | Weinberg et al. |
| 5,190,931 | A | 3/1993 | Inouye |
| 5,208,149 | A | 5/1993 | Inouye |
| 5,378,618 | A | 1/1995 | Sternberg et al. |
| 5,518,913 | A | 5/1996 | Massie et al. |
| 5,545,522 | A | 8/1996 | Van Gelder et al. |
| 5,652,224 | A | 7/1997 | Wilson et al. |
| 5,670,488 | A | 9/1997 | Gregory et al. |
| 5,707,618 | A | 1/1998 | Armentano et al. |
| 5,753,500 | A | 5/1998 | Shenk et al. |
| 5,837,511 | A | 11/1998 | Falck-Pedersen et al. |
| 5,922,576 | A | 7/1999 | He et al. |
| 5,935,935 | A | 8/1999 | Connelly et al. |
| 5,994,106 | A | 11/1999 | Kovesdi et al. |
| 5,994,128 | A | 11/1999 | Fallaux et al. |
| 6,033,908 | A | 3/2000 | Bout et al. |
| 6,040,174 | A | 3/2000 | Imler et al. |
| 6,238,893 | B1 | 5/2001 | Hoeben et al. |
| 6,306,652 | B1 | 10/2001 | Fallaux et al. |
| 6,413,776 | B1 | 7/2002 | Vogels et al. |
| 6,602,706 | B1 | 8/2003 | Fallaux et al. |

FOREIGN PATENT DOCUMENTS

| | | |
|---|---|---|
| AU | A-28533/95 | 3/1996 |
| CA | 2053187 | 4/1993 |
| CA | 2117668 | 9/1995 |
| EP | 95201611.1 | 6/1995 |
| EP | 95201728.3 | 6/1995 |
| FR | 2 707 664 | 1/1995 |
| WO | WO 91/02804 | * 3/1991 |
| WO | WO 94/12649 | 6/1994 |
| WO | WO 94/23582 | 10/1994 |
| WO | WO 94/26914 | 11/1994 |
| WO | WO 94/28152 | 12/1994 |
| WO | WO 95/00655 | 1/1995 |
| WO | WO 95/02697 | 1/1995 |
| WO | WO 95/27071 | 10/1995 |
| WO | WO 96/16676 | 6/1996 |
| WO | WO 96/18418 | 6/1996 |
| WO | WO 96/33280 | 10/1996 |
| WO | WO 96/40955 | 12/1996 |
| WO | WO 97/00326 | 1/1997 |
| WO | WO 97/00947 | 1/1997 |
| WO | WO 97/04119 | 2/1997 |
| WO | WO 97/05255 | 2/1997 |

OTHER PUBLICATIONS

Amalfitano et al., "Improved adenovirus packaging cell lines to support the growth of replication-defective gene-delivery vectors," *Proc. Natl. Acad. Sci. USA*, 93:3352-3356, Apr. 1996.

Amalfitano et al., "Isolation and characterization of packaging cell lines that coexpress the adenovirus E1, DNA polymerase, and preterminal proteins: implications for gene therapy," *Gene Therapy*, 4:258-263, 1997.

Armentano et al., "Characterization of an Adenovirus Gene Transfer Vector Containing an E4 Deletion," *Human Gene Therapy*, 6:1343-1353, Oct. 1995.

Berkner, Expression of Heterologous Sequences in Adenoviral Vectors, Current Topics in Microbiology and Immunology, vol. 158, Springer-Verlag Berlin Heidelberg 1992.

(Continued)

*Primary Examiner*—David Guzo  
(74) *Attorney, Agent, or Firm*—TraskBritt

(57) ABSTRACT

The invention provides improved methods and products based on adenoviral materials which can advantageously be used in gene therapy. In one aspect, an adenoviral vector is provided having no overlap with a suitable packaging cell line. The suitable packaging cell line is another aspect. The combination excludes the possibility of homologous recombination, thereby excluding the possibility of the formation of replication competent adenovirus. Another aspect embodies an adenovirus based helper construct which by its size is incapable of being encapsidated. This helper virus can be transferred into any suitable host cell making it a packaging cell. Furthermore, a number of useful mutations to adenoviral based materials and combinations of such mutations are disclosed, all of which have in common the safety of the methods and the products, in particular avoiding the production of replication competent adenovirus and/or interference with the immune system.

2 Claims, 27 Drawing Sheets

OTHER PUBLICATIONS

Blaese et al., Vectors in Cancer therapy: how will they deliver?, *Cancer Gene Therapy*, vol. 2, No. 4, 1995, pp. 291-297.

Bout et al., "In vivo adenovirus-mediated transfer of human CFTR cDNA to Rhesus monkey airway epithelium: efficacy, toxicity and safety," *Gene Therapy* 1, pp. 385-394, 1994.

Bout et al., "Lung Gene Therapy: In Vivo Adenovirus-Mediated Gene Transfer to Rhesus Monkey Airway Epithelium," *Human Gene Therapy*, 5:3-10, 1994.

Brough et al., "A Gene Transfer Vector-Cell Line System for Complete Functional Complementation of Adenovirus Early Regions E1 and E4," *Journal of Virology*, 70(9):6497-6501, Sep. 1996.

Brough et al., Stable Cell Lines for Complementation of Adenovirus Early Regions E1, E2A and E4; *Abstract Book CSH Conference on Gene Therapy*, 42, 1996.

Brough et al., "Construction, Characterization, and Utilization of Cell Lines Which Inducibly Express the Adenovirus DNA-Binding Protein," *Virology*, 190:624-634, 1992.

Caravokyri et al., "Constitutive Episomal Expression of Polypeptide IX (pIX) in a 293-Based Cell Line Complements the Deficiency of pIX Mutant Adenovirus Type 5," *Journal of Virology*, 69(11):6627-6633, Nov. 1995.

Fallaux et al., "Characterization of 911: A New Helper Cell Line for the Titration and Propagation of Early Region 1-Deleted Adenoviral Vectors," *Human Gene Therapy*, 7: 215-222, 1996.

Fisher et al., "Recombinant Adenovirus Deleted of All Viral Genes for Gene Therapy of Cystic Fibrosis," *Virology*, 217:11-22, 1996.

Gao et al., "Biology of Adenovirus Vectors with E1 and E4 Deletions for Liver-Directed Gene Therapy," *Journal of Virology*, 70(12):8934-8943, Dec. 1996.

Gorziglia et al., "Elimination of both E1 and E2a from Adenovirus Vectors Further Improves Prospects for In Vivo Human Gene Therapy," *Journal of Virology*, 70(6):4173-4178, Jun. 1996.

Haddada et al., "Adenoviral Interleukin-2 Gene Transfer into P815 Tumor Cells Abrogates Tumorigenicity and Induces Antitumoral Immunity in Mice," *Human Gene Therapy*, 4:703-711, 1993.

Hardy et al., "Construction of Adenovirus Vectors through Cre-lox Recombination," *Journal of Virology*, 71(3):1842-1849, Mar. 1997.

Hehir et al., "Molecular Characterization of Replication-Competent Variants of Adenovirus Vectors and Genome Modifications to Prevent Their Occurrence," *Journal of Virology*, 70(12):8459-8467, Dec. 1996.

Imler et al., "Novel complementation cell lines derived from human lung carcinoma A549 cells support the growth of E1-deleted adenovirus vectors," *Gene Therapy*, 3:75-84, 1996.

Kornberg, Arthur, "DNA Replication," W.H.Freeman and Company, San Francisco, 4 pages (double sided).

Krougliak et al., "Development of Cell Lines Capable of Complementing E1, E4, and Protein IX Defective Adenovirus Type 5 Mutants," *Human Gene Therapy*, 6: 1575-1586, Dec. 1995.

Lieber et al., "Recombinant Adenoviruses with Large Deletions Generated by Cre-Mediated Excision Exhibit Different Biological Properties Compared with First-Generation Vectors In Vitro and In Vivo," *Journal of Virology*, 70:8944-8960, Dec. 1996.

Ngo et al., "Computational Complexity, Protein Structure Prediction, and the Levinthal Paradox," *The Protein Folding Problem and Tertiary Structure Prediction*, 5 pages.

Sabatie et al., "Process Development for the Production of Second Generation Adenovirus Vectors for Gene Transfer in Clinical Protocols," *Abstract Book 14th Meeting on Animal Cell Technolgoy*, BI3, 1996.

Schaack et al., "Adenivorus Type 5 Precursor Terminal Protein-Expressing 293 and HeLa Cell Lines," *Journal of Virology*, 69(7):4079-4085, Jul. 1995.

Stratford-Perricaudet et al., Gene transfer into animals: the promise of adenovirus, Human Gene Transfer, 1991, vol. 219, pp. 51-61.

Vanhaesebroeck et al., "Modulation of Cellular Susceptibility to the Cytotoxic/Cytostatic Action of Tumor Necrosis Factor by Adenovirus E1 Gene Expression Is Cell Type-Dependent," *Virology*, 176(2), pp. 362-368, Jun. 1990.

Vincent et al., "Herpes Simplex Virus Thymidine Kinase Gene Therapy for Rat Malignant Brain Tumors," *Human Gene Therapy* 7:197-205, Jan. 20, 1996.

Vincent et al., "Treatment of leptomeningeal metastases in a rat model using a recombinant adenovirus containing the HSV-tk gene," *J. Neurosurg.*, vol. 85, pp. 648-654, 1996.

Wang et al., "A packaging cell line for propagation of recombinant adenovirus vectors containing two lethal gene-region deletions," *Gene Therapy*, 2:775-783, 1995.

Yeh et al., "Efficient Dual Transcomplementation of Adenovirus E1 and E4 Regions from a 293-Derived Cell Line Expressing a Minimal E4 Functional Unit", *Journal of Virology*, 70(1):559-565, Jan. 1996.

Zhou et al., "Development of a Complementing Cell Line and a System for Construction of Adenovirus Vectors with E1 and E2a Deleted," *Journal of Virology*, 70(1):7030-7038, Oct. 1996.

McKinnon et al., Tn5 mutagenesis of the transforming genes of human adenovirus type 5. Gene, 1982, pp. 33-42, vol. 19.

* cited by examiner

```
5'-GTACACTGACCTAGTGCCGCCCGGGCA
        |||||||||||||||| A
        GATCACGGCGGGCCCGA
```

(SEQ ID NO:47)

FIG. 15

Figure 20: Cloned adenovirus fragments

Figure 21: Adapter plasmid pAd5/L420-HSA

Figure 22: Adapter plasmid pAd5/CLIP

Figure 23: Generation of recombinant adenoviruses

Figure 24: Minimal adenovirus vector pMV/L42OH

Figure 25: Construction of pWE/AdΔ5'

Figure 26
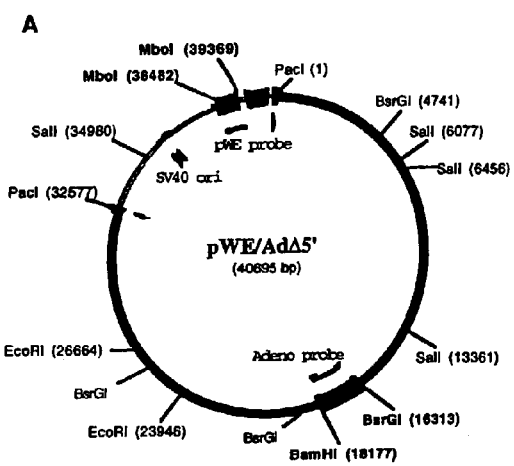
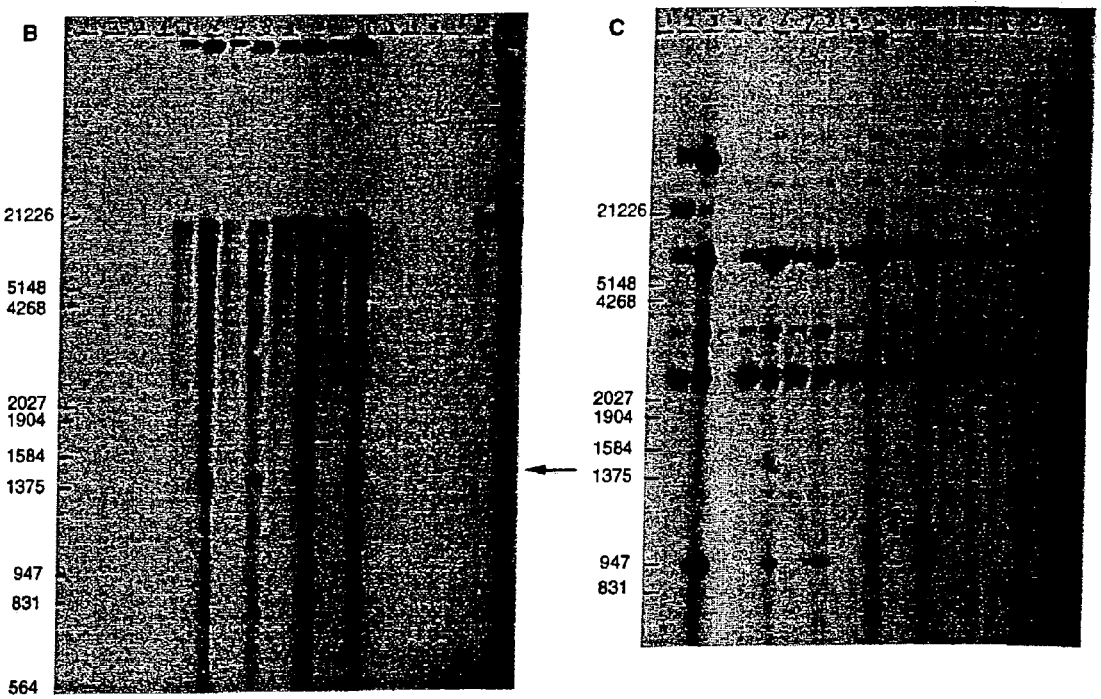

PACKAGING SYSTEMS FOR HUMAN RECOMBINANT ADENOVIRUS TO BE USED IN GENE THERAPY

CROSS-REFERENCE TO RELATED APPLICATION

This application is a continuation of application Ser. No. 09/900,062, filed Jul. 6, 2001, now abandoned, which was a divisional of application Ser. No. 09/065,752, filed Apr. 24, 1998, now U.S. Pat. No. 6,670,188, issued Dec. 30, 2003.

FIELD OF THE INVENTION

The invention relates to the field of recombinant DNA technology, especially to the field of gene therapy. More specifically, the invention relates to gene therapy using materials derived from adenoviruses, in particular human recombinant adenoviruses. The invention particularly relates to novel virus derived vectors and novel packaging cell lines for vectors based on adenoviruses.

BACKGROUND OF THE INVENTION

Gene therapy is a recently developed concept for which a wide range of applications can be and have been envisaged. In gene therapy a molecule carrying genetic information is introduced into some or all cells of a host, as a result the genetic information is added to the host in a functional format. Gene therapy includes the treatment of genetic disorders by providing the genetic information for supplementing a protein or other substance. The protein or other substance is not present or is at least present in insufficient amounts in the host. Gene therapy is also used for the treatment of tumors and (other) acquired disease such as (auto) immune diseases or infections, or other processes. The genetic information added may be a gene or a derivative of a gene, such as a cDNA, which encodes a protein. In this case, the functional format means that the protein can be expressed by the machinery of the host cell. The genetic information can also be a sequence of nucleotides complementary to a sequence of nucleotides (be it DNA or RNA) present in the host cell. The functional format in this case is that the added DNA (nucleic acid) molecule or copies made thereof in situ are capable of base pairing with the complementary sequence present in the host cell.

Thus, there are basically three different approaches in gene therapy, one directed towards compensating a deficiency present in a (mammalian) host; the second directed towards the removal or elimination of unwanted substances (organisms or cells); and the third directed towards application of a recombinant vaccine (tumors or foreign microorganisms).

For the purposes of gene therapy, adenoviruses carrying deletions have been proposed as suitable vehicles. Adenoviruses are non-enveloped DNA viruses. Gene transfer vectors derived from adenoviruses (so called adenoviral vectors) have a number of features that make them particularly useful for gene transfer. Examples of these features include the biology of the adenoviruses which has been characterized in detail, the adenovirus is not associated with severe human pathology, the virus is extremely efficient in introducing its DNA into the host cell, the virus can infect a wide variety of cells and has a broad host range, the virus can be produced in large quantities with relative ease and the virus can be rendered replication defective by deletions in the early region 1 (E1) of the viral genome.

The adenovirus (Ad) genome is a linear double-stranded DNA molecule of approximately 36,000 base pairs with the 55-kDa terminal protein covalently bound to the 5' terminus of each strand. The Ad DNA contains identical Inverted Terminal Repeats (ITR) of about 100 base pairs with the exact length depending on the serotype. The viral origins of replication are located within the ITRs, exactly at the genome ends. DNA synthesis occurs in two stages. The replication proceeds by strand displacement by generating a daughter duplex molecule and a parental displaced strand. The displaced strand is single stranded and can form a so called "panhandle" intermediate, which allows replication initiation and generation of a daughter duplex molecule. Alternatively, replication may proceed from both ends of the genome simultaneously obviating the requirement to form the panhandle structure. The replication is summarized in FIG. 14 adapted from Lechner et al, (1977) *J. Mol. Biol.* 174:493–510.

During the productive infection cycle, the viral genes are expressed in two phases: the early phase, which is the period up to viral DNA replication, and the late phase, which coincides with the initiation of viral DNA replication. During the early phase, only the early gene products encoded by regions E1, E2, E3 and E4 are expressed. These regions carry out a number of functions that prepare the cell for synthesis of viral structural proteins (Berk, A. J. (19.86) *Ann. Rev. Genet.* 20: 45–79). During the late phase, the late viral gene products are expressed in addition to the early gene products, and host cell DNA and protein synthesis are shut off. Consequently, the cell becomes dedicated to the production of viral DNA and of viral structural proteins (Tooze, J. (1981) *DNA Tumor Viruses (revised)*, Cold Spring Harbor Laboratory, Cold Spring Harbor, N.Y.).

The E1 region of adenovirus is the first region of adenovirus expressed after infection of the target cell. This region consists of two transcriptional units, the E1A and E1B genes, both of which are required for oncogenic transformation of primary (embryonal) rodent cultures. The main functions of the E1A gene products are to induce quiescent cells to enter the cell cycle and resume cellular DNA synthesis, and to transcriptionally activate the E1B gene and the other early regions (E2, E3 and E4) of the viral genome. Transfection of primary cells with the E1A gene alone can induce unlimited proliferation (immortalization), but does not result in complete transformation. However, expression of E1A in most cases results in induction of programmed cell death (apoptosis), and only occasionally immortalization is obtained (Jochemsen et al, (1987) *EMBO J* 6:3399–3405). Co-expression of the E1B gene is required to prevent induction of apoptosis and for complete morphological transformation to occur. In established immortal cell lines, high level expression of E1A can cause complete transformation in the absence of E1B (Roberts et al, (1985) *J. Virol.* 56:404–413).

The E1B encoded proteins assist E1A in redirecting the cellular functions to allow viral replication. The E1B 55 kD and E4 33 kD proteins, which form a complex that is essentially localized in the nucleus, function in inhibiting the synthesis of host proteins and in facilitating the expression of viral genes. Their main influence is to establish selective transport of viral mRNAs from the nucleus to the cytoplasm, concomitantly with the onset of the late phase of infection. The E1B 21 kD protein is important for correct temporal control of the productive infection cycle, thereby preventing premature death of the host cell before the virus life cycle has been completed. Mutant viruses incapable of expressing the E1B 21 kD gene product exhibit a shortened infection cycle that is accompanied by excessive degradation of host cell chromosomal DNA (deg-phenotype) and in an enhanced cytopathic effect (cyt-phenotype) (Telling et al, (1994) *J. Virol.* 68:541–7). The deg and cyt phenotypes are suppressed when in addition the E1A gene is mutated, indicating that these phenotypes area function of E1A (White et al, (1988) *J. Virol.* 62:3445–3454). Furthermore, the E1B 21 kDa protein slows down the rate by which E1A switches on the other viral genes. It is not yet known through which mechanisms E1B 21 kD quenches these E1A dependent functions.

Vectors derived from human adenoviruses, in which at least the E1 region has been deleted and replaced by a gene of interest, have been used extensively for gene therapy experiments in the pre-clinical and clinical phase. Currently, all adenovirus vectors used in gene therapy have a deletion in the E1 region, where novel genetic information can be introduced. The E1 deletion renders the recombinant virus replication defective (Stratford-Perricaudet et al, (1991) pp. 51–61. In O. Cohen-Adenaur, and M. Boiron (Eds): *Human Gene Transfer*, John Libbey Eurotext).

In contrast to, for example, retroviruses, adenoviruses do not integrate into the host cell genome, are able to infect non-dividing cells and are able to efficiently transfer recombinant genes in vivo (Brody et al, (1994) *Ann. N.Y. Acad. Sci.* 716:90–101). These features make adenoviruses attractive candidates for in vivo gene transfer of, for example, suicide or cytokine genes into tumor cells. However, a problem associated with current recombinant adenovirus technology is the possibility of unwanted generation of replication competent adenovirus (RCA) during the production of recombinant adenovirus (Lochmüller et al, (1994) *Hum. Gene Ther.* 5:1485–1492; Imler et al, (1996) *Gene Ther.* 3:75–84). This is caused by homologous recombination between overlapping sequences from the recombinant vector and the adenovirus constructs present in the complementing cell line, such as the 293 cells (Graham et al, (1977) *J. Gen. Virol.* 36:59–72). RCA in batches to be used in clinical trials is unwanted because RCA i) will replicate in an uncontrolled fashion; ii) can complement replication defective recombinant adenovirus, causing uncontrolled multiplication of the recombinant adenovirus; and iii) batches containing RCA induce significant tissue damage and hence strong pathological side effects (Lochmüller et al, (1994) *Hum. Gene Ther.* 5:1485–1492). Therefore, batches to be used in clinical trials should be, proven free of RCA (Ostrove, J. M. (1994) *Cancer Gene Ther.* 1:125–131).

One of the additional problems associated with the use of recombinant adenovirus vectors is the host defense reaction against treatment with adenovirus. Briefly, recombinant adenoviruses are deleted for the E1 region (see above). The adenovirus E1 products trigger the transcription of the other early genes (E2, E3, E4), which consequently activate expression of the late virus genes. Therefore, it was generally thought that E1 deleted vectors would not express any other adenovirus genes. However, recently it has been demonstrated that some cell types are able to express adenovirus genes in the absence of E1 sequences. This indicates, that some cell types possess the machinery to drive transcription of adenovirus genes. In particular, it was demonstrated that such cells synthesize E2A and late adenovirus proteins. In a gene therapy setting, this means that transfer of the therapeutic recombinant gene to somatic cells not only results in expression of the therapeutic protein, but may also result in the synthesis of viral proteins. Cells that express adenoviral proteins are recognized and killed by cytotoxic T Lymphocytes, which eradicate the transduced cells and cause inflammation (Bout et al, (1994a) *Gene Therapy* 1:385–394; Engelhardt et al, (1993) *Human Gene Therapy* 4:759–769; Simon et al, (1993) *Human Gene Therapy* 4:771–780). As this adverse reaction hampers gene therapy, several solutions to this problem have been suggested, such as using immunosuppressive agents after treatment, retaining the adenovirus E3 region in the recombinant vector (see patent application EP 9520221 B) or using ts mutants of human adenovirus, which have a point mutation in the E2A region (patent WO/28938). However, these strategies to circumvent the immune response have their limitations. The use of a ts mutant recombinant adenovirus diminishes the immune response to some extent, but is not as effective in preventing pathological responses in the lungs (Engelhardt et al, (1994a) *Human Gene Ther.* 5:1217–1229). The E2A protein may induce an immune response by itself and it plays a pivotal role in the switch to the synthesis of late adenovirus proteins. Therefore, it is attractive to make recombinant adenoviruses which are mutated in the E2 region, rendering it temperature sensitive (ts), as has been claimed in patent application WO/28938. A major drawback of this system is the fact that, although the E2 protein is unstable at the non-permissive temperature, the immunogenic protein is still synthesized. In addition, it is expected that the unstable protein activates late gene expression to a low extent. ts125 mutant recombinant adenoviruses have been tested, and prolonged recombinant gene expression was reported (Yang et al, (1994b) *Nat Genet.* 7:362–369; Engelhardt et al, (1994a) *Hum. Gene Ther.* 5:1217–1229; Engelhardt et al, (1994b) *Proc Natl Acad Sci USA* 91:6196–200; Yang et al, (1995) *J. Virol.* 69:2004–2015). However, pathology in the lungs of cotton rats was still high (Engelhardt et al, (1994a) *Human Gene Ther.* 5:1217–1229), indicating that the use, of ts mutants results in only a partial improvement in recombinant adenovirus technology. Others (Fang et al, (1996) *Gene Ther.* 3:217–222) did not observe prolonged gene expression in mice and dogs using ts 125 recombinant adenovirus. An additional difficulty associated with the use of ts125 mutant adenoviruses is that a high frequency of reversion is observed. These revertants are either real revertants or the result of second site mutations (Kruijer et al, (1983) *Virology* 124:425–433; Nicolas et al, (1981) *Virology* 108:521–524). Both types of revertants have an E2A protein that functions at normal temperature and therefore have similar toxicity as the wild-type virus.

E1 deleted recombinant adenoviruses are usually made by one of the following methods. In the first method, adenovirus DNA, be it wild type (wt) or E1 and/or E3 deleted, is digested with a restriction enzyme e.g. ClaI, to remove the left ITR, packaging signal and at least part of the E1 sequences. The remaining adenovirus genome fragment (1) is then purified. Cotransfection of (1) with a linearized adapter construct (2) containing the left ITR, packaging signal, an expression cassette with the gene of interest and adenovirus sequences overlapping with (1) in a cell line complementing for E1 functions (packaging cell line) will give rise to recombinant adenovirus particles by intracellular homologous recombination. Alternatively, an adapter construct (3) containing the left ITR, packaging signal, and an expression cassette with the gene of interest is such that it can be ligated to the adenovirus DNA fragment (1) followed by transfection into packaging cells. The disadvantage of these methods is that the purification of (1) is laborious, and that incomplete digestion of wt DNA results in introduction of wt adenovirus into the culture leads to contamination. An approach to circumvent this problem has been by the construction of clone pHBG10 described by Bett et al, (1994) *Natl. Acad. Sci. USA* 91:8802–8806. This plasmid clone contains Ad5 sequences with a deletion of the packaging signal and part of the E1 region and with the viral ITRs attached to each other. However, this clone comprises adenovirus sequences that are also present in E1-complementing cell lines, including those of the present invention (see EP 95201611.1). Furthermore, since the ITRs are attached to each other, the clone cannot be linearized, thus resulting in less efficient recombination with the E1 substitution plasmid.

In the second method, the recombinant adenoviruses is constructed either by homologous recombination in bacteria (Chartier et al, (1996) *J. Virol.* 70, No.7:4805–4810; Croozet et al, (1997) *Proc. Natl. Acad. Sci. USA* 94:1414–1419) or by cloning into cosmid vectors (Fu et al, (1997) *Hum. Gene Ther.* 8:1321–1330) and subsequent transfection into an E1 complementing cell line. The disadvantage of this method is that it demands extensive analysis of each generated clone (~35 kb) by restriction enzyme digestion before transfection to exclude deletions that occurred due to recombination in the bacteria. In addition, the use of cloned adenovirus sequences does not solve the problem of sequence overlap between commonly used packaging cells and recombinant viruses leading to production of RCA during propagation.

A third method used, is a two-step gene replacement technique in yeast, starting with a complete adenovirus genome (Ad2; Ketner et al, (1994) *Proc. Natl. Acad. Sci. USA* 91:6186–6190) cloned in a Yeast Artificial Chromosome (YAC) and a plasmid containing adenovirus sequences to target a specific region in the YAC clone, an expression cassette for the gene of interest and a positive and negative selectable marker. This method requires yeast technology and extensive analysis of each new recombinant clone (even more cumbersome than the above described method, due to the large size of YACs).

A fourth method uses a cosmid clone (pAdexlw; Miyake et al, (1996) *Medical Sciences* 93:1320–1324) that carries the Ad5 sequence with deletions in the E1 and E3 sequences. This clone has a unique restriction site replacing part of the E1 region that allows insertion of a foreign expression cassette. For the generation of recombinant adenoviruses, a DNA-terminal protein complex (DNA-TPC) is isolated from cells infected with a replication competent adenovirus Ad-dlX (wt Ad5 with an XbaI deletion in the E3 region). This DNA is digested with EcoT22I to remove the 5' part of the DNA, and cotransfected with the cosmid cloned into E1 complementing cells. Intracellular recombination generates the recombinant virus (Miyake et al, (1996) *Medical Sciences* 93:1320–1324). This method has the disadvantage that replication competent viral DNA is used and that the E1 deletion in the cosmid clone is not enough to remove all overlap with E1 sequences currently used in packaging cell lines including those used in the present invention. Thus, current methods to generate RCA-free recombinant adenoviruses have several disadvantages, including the risk of introducing wild-type viruses in the culture, instability of cloned adenovirus sequences, the necessity to check the complete ~35 kb recombinant clone by restriction analysis for each new virus to be generated, and the system being suitable only for E1 deleted recombinant adenoviruses and much more laborious for use with recombinant adenoviruses comprising E3 substitutions. Furthermore, despite the use of cloned adenovirus DNA in some of the methods, extensive overlap with adenovirus sequences present in commonly used packaging cells like 293 and 911 cells do not solve the problem of appearance of RCA due to homologous recombination during propagation of the virus. Therefore, a need persists for methods and means to produce RCA-free recombinant adenovirus preparations that solve the disadvantages of prior art methods and means discussed above. Gene addition is currently by far the most widely applied gene therapy technique. This is mainly due to the fact that a) homologous recombination is very inefficient and b) for homologous recombination relatively large DNA fragments are required for which no suitable vector systems were available. Thus, there is currently an unmet need for vector systems that efficiently introduce large nucleic acid molecules into mammalian cells.

Recombinant adenoviruses are able to efficiently transfer recombinant genes to the rat liver and airway epithelium of rhesus monkeys (Bout et al, (1994b) *Human Gene Therapy* 5:3–10; Bout et al, (1994a) *Gene Therapy* 1:385–394). In addition, Vincent et al, ((1996) *J. Neurosurg* 85:648–654; Vincent et al, (1996b) *Hum. Gene Ther.* 7:197–205) and others (see for example Haddada et al, (1993) *Hum Gene Ther.* 4:703–11) have observed an efficient in vivo adenovirus mediated gene transfer to a variety of tumor cells in vitro and to solid tumors in animal models (lung tumors, glioma) and human xenografts in immunodeficient mice (lung) in vivo (reviewed by Blaese et al, *Cancer Gene Ther.* 2:291–297).

Generation of minimal adenovirus vectors has been disclosed in WO 94/12649. The method described exploits the function of the protein IX for the packaging of minimal adenovirus vectors (Pseudo Adenoviral Vectors (PAV) in the terminology of WO 94/12649). PAVs are produced by cloning an expression plasmid with the gene of interest between the left-hand (including the sequences required for encapsidation) and the right-hand adenoviral ITRs. The PAV is propagated in the presence of a helper virus. Encapsidation of the PAV is preferred compared to the helper virus because the helper virus is partially defective for packaging (either by virtue of mutations in the packaging signal or by virtue of its size (virus genomes greater than 37.5 kb package inefficiently)). In addition, the authors propose that in the absence of the protein IX gene the PAV will be preferentially packaged. However, neither of these mechanisms appear to be sufficiently restrictive to allow packaging of only PAVs/minimal vectors. The mutations proposed in the packaging signal diminish packaging, but do not provide an absolute block, as the same packaging activity is required to propagate the helper virus. Also, neither an increase in the size of the helper virus nor the mutation of the protein IX gene will ensure that PAV is packaged exclusively. Thus, the method described in WO 94/12649 is unlikely to be useful for the production of helper-free stocks of minimal adenovirus vectors PAVs.

BRIEF SUMMARY OF THE INVENTION

Novel compositions and methods are provided for producing recombinant adenoviruses, not only E1-deleted, but also minimal adenoviruses which are free of replication competent adenoviruses. The compositions include constructs suitable for the generation of double insert viruses. The system provided by the invention to generate E1 deleted adenoviruses consists of two nucleic acid moieties. The first nucleic acid moiety is a relatively small and easy to manipulate adapter plasmid containing at least, in an operable configuration, the left ITR, the packaging signal, an expression cassette with the nucleic acid molecule of interest and adenovirus sequences homologous to a part of the second moiety that comprises one, or two or more partially overlapping, nucleic acid molecules that comprise at least all adenovirus sequences necessary for replication and packaging, and the packaging cells of the invention described infra. Co-transfection of the, two nucleic acid moieties into the packaging cells leads to homologous recombination between the overlapping sequences in said two nucleic acid moieties. This generates a recombinant viral DNA that is able to replicate and propagate on the packaging cells. The nucleic acid moieties have no sequence overlap with the E1 complementing sequences in packaging cells that can lead to the formation of replication competent adenovirus (RCA). Preferably, at least one of the ITRs on the nucleic acid moieties is flanked by a restriction enzyme recognition site not present in the adenoviral sequences so that the ITR can be made free from vector sequences by digestion of the DNA with that restriction enzyme. Thus, replication occurs more efficiently. The system provided by the present invention also greatly facilitates the production of RCA-free recombinant adenoviruses with further modifications in the adenovirus genome, including but not limited to modifications in the coding regions for the penton base protein or fiber protein or E2A protein.

BRIEF DESCRIPTION OF THE DRAWINGS

FIG. 15 illustrates the potential hairpin conformation of a single-stranded DNA molecule that contains the HP/asp sequence. Asp718 I digestion of pICLha, containing the cloned oligonucleotides, HP/asp1 and HP/asp2 yields a linear double-stranded DNA with an Ad5 ITR at one terminus and the HP/asp sequence at the other terminus. In cells, expressing the adenovirus E2 region, a single-stranded DNA is produced with an Ad5 ITR at the 5'-terminus and the hairpin conformation at the 3'-terminus. Once formed, the hairpin can serve as a primer for cellular and or adenovirus DNA polymerase to convert the single stranded DNA to double stranded DNA.

FIG. 26 (Parts A–C) depicts evidence for SV40-LargeT/ori mediated replication of large adenoviral constructs in Cos-1 cells. Part A: Schematic presentation of construct pWE/Ad.Δ5' and the location of the SV40 ori sequence and the fragments used to prepare probes.

Figure 1:
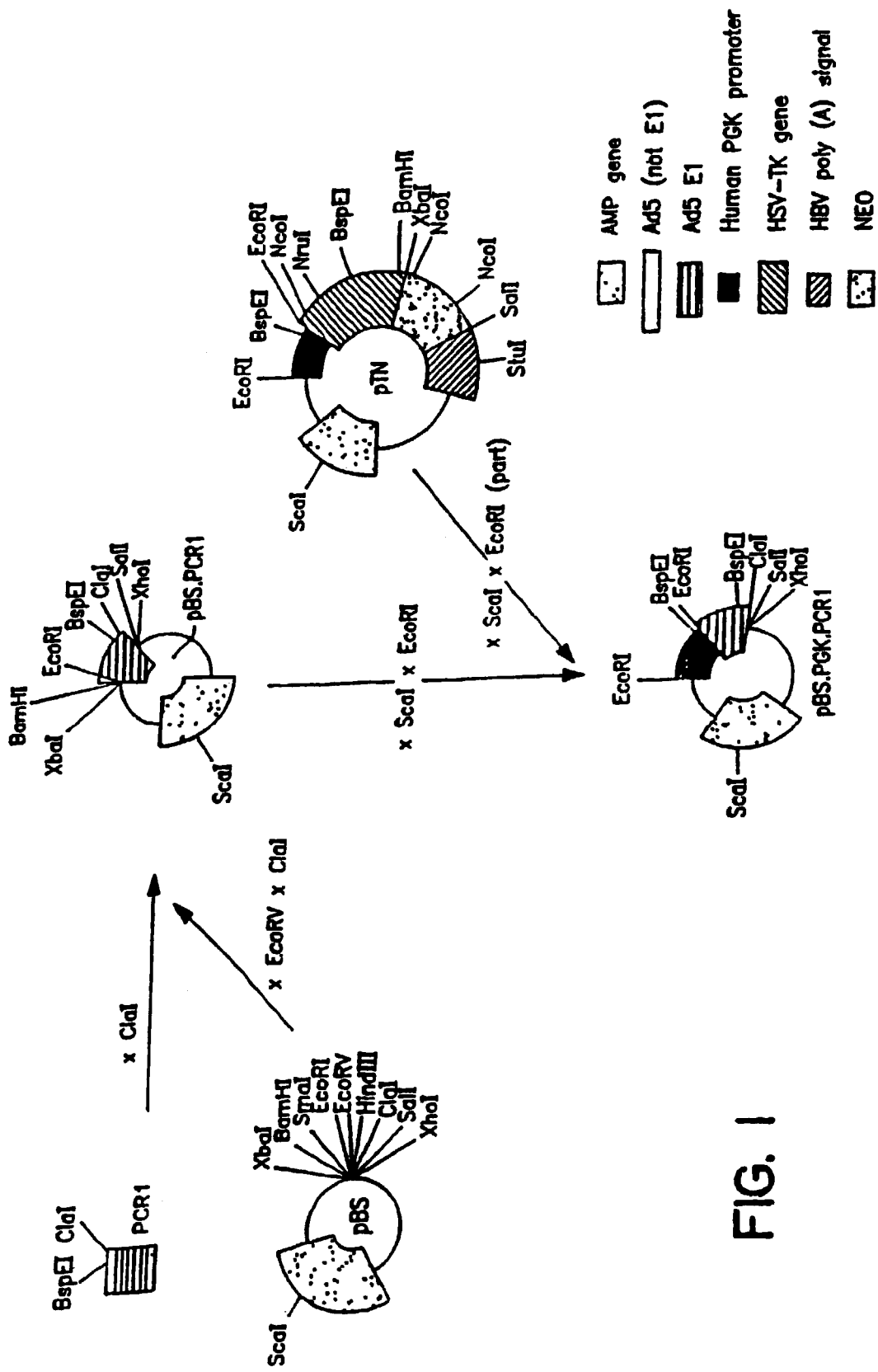
FIG. 1 depicts construction of pBS.PGK.PCRI. pBS.PGK.PCRI encodes the human phosphoglycerate kinase promoter (PGK) operatively linked to adenovirus 5 (Ad5) E1 nucleotides 459–916. To construct this plasmid, Ad5 nucleotides 459–916 were PCR amplified with primers Ea-1 and Ea-2, digested with Cla I and cloned into the Cla I-EcoR V sites of pBluescript (Stratagene), resulting in pBS.PCRI. The PGK promoter was excised from pTN by complete digestion with Sca I and partial digestion with EcoR I and cloned into the corresponding sites of pBS.PCRI, resulting in pBS.PGK.PCRI.

Part B: Autoradiogram of the Southern blot hybridised to the adenovirus probe. C) Autoradiogram of the Southern blot hybridised to the pWE probe. Lanes 1, marker lane: λDNA digested with EcoRI and HindIII. Lane 4 is empty. Lanes 2, 5, 7, 9, 11, 13, 15 and 17 contain undigested DNA and Lanes 3, 6, 8, 10, 12, 14, 16 and 18 contain MboI digested DNA. All lanes contain DNA from Cos-1 cells as described in the text transfected with pWE.pac (lanes 2 and 3), pWE/Ad.Δ5' construct #1 (lanes 5 and 6), #5 (lanes 7 and 8) and #9 (lanes 9 and 10), pWE/Ad.AflII-rITR (lanes 11 and 12), pMV/CMV-LacZ (lanes 13 and 14), pWE.pac digested with PacI (lanes 15 and 16) or pWE/Ad.AflII-rITR digested with PacI (lanes 17 and 18). Arrows point at the expected positive signal of 1416 bp (B) and 887 bp (C).

DETAILED DESCRIPTION OF THE INVENTION

In one aspect of the invention, the problem with RCA production is solved in that we have developed packaging cells that have no overlapping sequences with a new basic vector and thus, are suited for safe large scale production of recombinant adenoviruses.

In another aspect of the present invention, we deleted E2A coding sequences from the recombinant adenovirus genome and transfected these E2A sequences into the (packaging) cell lines containing E1 sequences to complement recombinant adenovirus vectors.

Major hurdles in this approach are a) that E2A should be expressed to very high levels; and b) that E2A protein is very toxic to cells.

The current invention also discloses use of the ts125 mutant E2A gene, which produces a protein that is not able to bind DNA sequences at the non permissive temperature. High levels of this protein may be maintained in the cells (because it is not toxic at this temperature) until the switch to the permissive temperature is made. This can be combined with placing the mutant E2A gene under the direction of an inducible promoter, such as for instance tet, methallothionein, steroid inducible promoter, retinoic acid β-receptor or other inducible systems. However, in yet another aspect of the invention, the use of an inducible promoter to control the moment of production of toxic wild-type E2A is disclosed. Two salient additional advantages of E2A-deleted recombinant adenovirus are the increased capacity to harbor heterologous sequences, and the permanent selection for cells that express the mutant E2A. This second advantage relates to the high frequency of reversion of ts 125 mutation: when reversion occurs in a cell line harboring ts125 E2A, this will be lethal to the cell. Therefore, there is a permanent selection for those cells that express the ts125 mutant E2A protein. In addition, we will not have the problem of reversion in our adenoviruses as we generate E2A-deleted recombinant adenoviruses.

In yet another aspect of the invention, a further improvement of the use of non-human cell lines as packaging cell lines is disclosed.

For GMP production of clinical batches of recombinant viruses it is desirable to use a cell line that has been used widely for production of other biotechnology products. Most of the latter cell lines are from monkey origin, which have often been used to produce vaccines.

These cells cannot be used directly for the production of recombinant human adenovirus, as human adenovirus cannot replicate in cells of monkey origin or only replicate at low levels. A block in the switch of early to late phase of adenovirus lytic cycle underlies the defective replication. However, host range (hr) mutations in the human adenovirus genome are described(hr400–404) which allow replication of human viruses in monkey cells. These mutations reside in the gene encoding E2A protein (Klessig et al; (1979) *Cell* 17:957–966; Klessig et al,. (1984). *Virus Res.* 1:169–188; Rice et al, (1985) *J. Virol.* 56:767–778) (Klessig et al, (1984) *Virus Res.* 1:169–188). Moreover, mutant viruses have been described that harbor both the hr and temperature-sensitive ts125 phenotype (Brough et al, (1985) *J. Virol.* 55,206–212; Rice et al, (1985) *J. Virol.* 56:767–778).

We therefore generate packaging cell lines of monkey origin (e.g., VERO, CV1) that harbor:
  a) E1 sequences, to allow replication of E1/E2 defective adenoviruses, and
  b) E2A sequences, containing the hr mutation and the ts125 mutation, named ts400 (Brough et al, (1985) *J. Virol.* 55:206–212; Rice et al, (1985) *J. Virol.* 56:767–778 to prevent cell death by E2A overexpression, and/or
  c) E2A sequences, just containing the hr mutation, under the control of an inducible promoter, and/or
  d) E2A sequences, containing the hr mutation and the ts125 mutation (ts400), under the control of an inducible promoter.

Furthermore, we disclose the construction of novel and improved combinations of (novel and improved) packaging cell lines and (novel and improved) recombinant adenovirus vectors.

We provide:
1) a novel packaging cell line derived from diploid human embryonic retinoblasts (HER) that harbors nt. 80–5788 of the Ad5 genome. This cell line, named 911, deposited under no. 95062101 at the ECACC, has many characteristics that make it superior to the commonly used 293 cells (Fallaux et al, (1996) *Hum. Gene Ther.* 7:21;5–222).
2) novel packaging cell lines that express just E1A genes and not E1B genes. Established cell lines (and not human diploid cells of which 293 and 911 cells are derived) are able to express E1A to high levels without undergoing apoptotic cell death, as is often evidenced in human diploid cells that express E1A in the absence of E1B. Such cell lines are able to transcomplement E1B-defective recombinant adenoviruses, because viruses mutated for E1B 21 kD protein are able to complete viral replication even faster than wild-type adenoviruses (Telling et al, (1994) *J. Virol* 68:541–7). The constructs are described in detail below, and graphically represented in FIGS. 1–5. The constructs are transfected into the different established cell lines and are selected for high expression of E1 A. This is done by operatively linking a selectable marker gene (e.g. NEO gene) directly to the E1B promoter. The E1B promoter is transcriptionally activated by the E1A gene product and therefore resistance to the selective agent (e.g. G418 in the case NEO is used as the selection marker) results in direct selection for desired expression of the E1A gene.
3) Packaging constructs that are mutated or deleted for E1B 21 kD, but just express the 55 kD protein.
4) Packaging constructs to be used for generation of complementing packaging cell lines from diploid cells (not exclusively of human origin) without the need of selection with marker genes. These cells are immortalized by expression of E1A. However, in this particular case expression of E1B is essential to prevent apoptosis induced by E1A proteins. Selection of E1 expressing cells is achieved by selection for focus formation (immortalization), as described for 293 cells (Graham et al,) *J. Gen. Virol.* 36:59–72) and 911 cells (Fallaux et al, (1996) *Hum. Gene Ther.* 7:215–222) that are E1 transformed human embryonic kidney (HEK) cells and human embryonic retinoblasts (HER), respectively.
5) After transfection of HER cells with construct pIG.E1A.E1B (FIG. 4), seven independent cell lines could be established. These cell lines were designated PER.C1, PER.C3, PER.C4, PER.C5, PER.C6, PER.C8 and PER.C9. PER denotes PGK-E1-Retinoblasts. These cell lines express. E1A and E1B proteins, are stable (e.g. PER.C6 for more than 57 passages) and complement E1 -defective adenovirus vectors. Yields of recombinant adenovirus obtained on PER cells are a little higher than obtained on 293 cells. One of these cell lines (PER.C6) has been deposited at the ECACC under number 96022940.

6) New adenovirus vectors with extended E1 deletions (deletion nt. 459–3510). Those viral vectors lack sequences homologous to E1 sequences in said packaging cell lines. These adenoviral vectors contain pIX promoter sequences and the pIX gene, as pIX (from its natural promoter sequences) can only be expressed from the vector and not by packaging cells (Matsui et al, (1986) *Mol. Cell Biol.* 6:4149–4154, Hoeben and Fallaux, pers. comm.; Imler et al, (1996) *Gene Ther.* 3:75–84).

7) E2A expressing packaging cell lines preferably based on either E1A expressing established cell lines or E1A+E1B expressing diploid cells (see under 2–4). E2A expression is either under the control of an inducible promoter or the E2A ts125 mutant is driven by either an inducible or a constitutive promoter.

8) Recombinant adenovirus vectors as described before (see 6) but carrying an additional deletion of E2A sequences.

9) Adenovirus packaging cells from monkey origin that are able to transcomplement E1-defective recombinant adenoviruses. They are preferably co-transfected with pIG.E1AE1B and pIG.NEO, and selected for NEO resistance. Such cells expressing E1A and E1B are able to transcomplement E1 defective recombinant human adenoviruses, but will do so inefficiently because of a block of the synthesis of late adenovirus proteins in cells of monkey origin (Klessig et al, (1979) *Cell* 17:957–966). To overcome this problem, we generate recombinant adenoviruses that harbor a host-range mutation in the E2A gene, allowing human adenoviruses to replicate monkey cells. Such viruses are generated as described in FIG. 12, except DNA from a hr-mutant is used for homologous recombination.

10) Adenovirus packaging cells from monkey origin as described under 9, except that they will also be co-transfected with E2A sequences harboring the hr mutation. This allows replication of human adenoviruses lacking E1 and E2A (see under 8). E2A in these cell lines is either under the control of an inducible promoter or the tsE2A mutant is used. In the latter case, the E2A gene will thus carry both the ts mutation and the hr mutation (derived from ts400). Replication competent human adenoviruses have been described that harbor both mutations (Brough et al, *J. Virol.* 55:206–212; Rice et al, (1985) *J. Virol.* 56:767–778).

Furthermore, the present invention provides new cosmid and plasmid vectors containing large fragments of the adenovirus genome and an improved method for the generation of recombinant adenoviral vectors by making use of these cloned adenovirus sequences.

Accordingly, the present invention provides a new system to generate recombinant adenoviruses that is fast, highly flexible, reliable and only requires standard cloning technology. In combination with the packaging cells of the invention it ensures RCA-free generation and propagation of recombinant adenoviruses. The above listed problems associated with current methods to generate recombinant adenoviruses are solved by using a functional combination of cloned adenovirus sequences and an intra-cellular homologous recombination in suitable packaging cells.

Accordingly, the present invention provides methods and means to efficiently generate and produce vectors that are able to harbor very large fragments of (genomic) DNA. These vectors can be safely produced to very high titers and are able to transduce mammalian cells, including human cells, with high efficiency, thereby favoring homologous recombination with (genomic) DNA molecules present in said mammalian cells, due to the high numbers of introduced DNA molecules and their large homologous overlap with the target DNA molecules for recombination. The vectors according to the invention are based on adenoviral vectors derived from an adenoviral genome, from which as much as possible of the adenoviral genome is deleted except for the ITR sequences and the sequences needed in cis for packaging (minimal adenovirus vectors). Such vectors can accommodate up to 38 kb of foreign (genomic) DNA.

Minimal adenoviral vectors with large genomic sequences functioning as gene replacement vectors can be generated efficiently using the plasmid-based intracellular PCR system disclosed infra, thereby avoiding the need of contaminating helper viruses. In addition, we disclose an alternative way of producing minimal adenoviral vectors without the need for helper viruses. Replication and packaging of the minimal adenoviral vectors with large inserts can also be achieved by using them in combination with a complementing molecule containing all parts of the adenovirus genome that are required for replication and packaging except for the packaging signal and E1 sequences. Such a complementing molecule need not necessarily replicate by the virtue of the adenoviral replication machinery. It may, for example, be cloned on a plasmid that also contains the SV40 origin of replication. Transfection of this DNA together with the minimal adenoviral vector in a E1-containing packaging cell that also (inducibly) expresses the SV40 Large T protein will lead to replication of the adenovirus molecule and expression of adenoviral proteins. The latter will then initiate replication and packaging of the minimal adenoviral vectors.

A further aspect of the invention provides otherwise improved adenovirus vectors, as well as novel strategies for generation and application of such vectors and a method for the intracellular amplification of linear DNA fragments in mammalian cells.

The so-called "minimal" adenovirus vectors according to the present invention retain at least a portion of the viral genome that is required for encapsidation of the genome into virus particles (the encapsidation signal), as well as at least one copy of at least a functional part or a derivative of the Inverted Terminal Repeat (ITR). That is, DNA sequences derived from the termini of the linear adenovirus genome. The vectors according to the present invention will also contain a transgene linked to a promoter sequence to govern expression of the transgene. Packaging of the so-called minimal adenovirus vector can then be achieved by co-infection with a helper virus or, alternatively, with a packaging deficient replicating helper system as described below.

Figure 13:
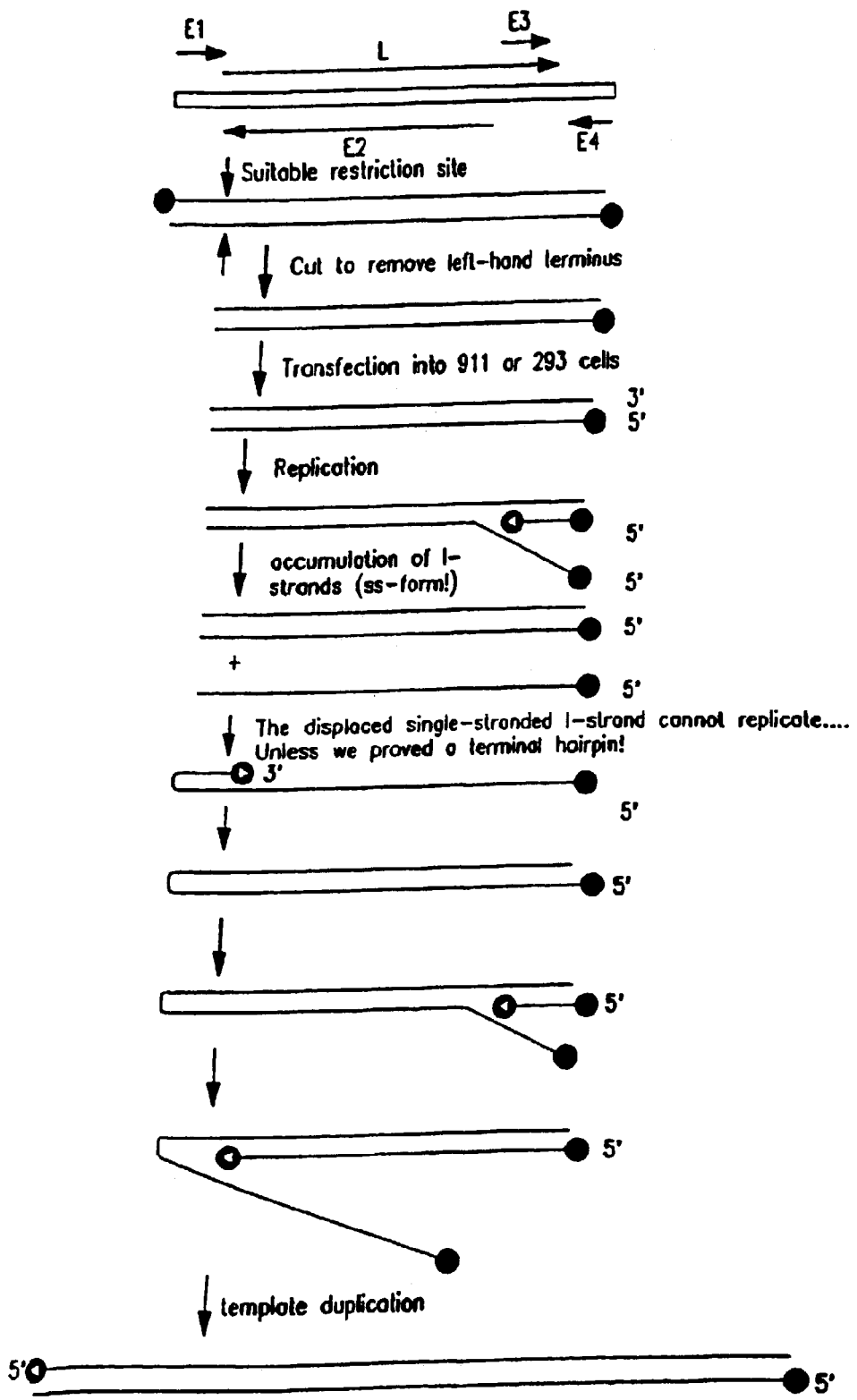
FIG. 13 illustrates the rationale for the design of adenovirus-derived recombinant DNA molecules that duplicate and replicate in cells expressing adenovirus replication proteins. A diagram of the adenovirus double-stranded DNA genome indicating the approximate locations of E1, E2, E3, E4, and L regions is shown. The terminal polypeptide (TP) attached to the 5'-termini is indicated by closed circles. The right arm of the adenovirus genome can be purified by removal of the left arm by restriction enzyme digestion. Following transfection of the right arm into 293 or 911 cells, adenoviral DNA polymerase (white arrow) encoded on the right arm, will produce only single-stranded forms. Neither the double-stranded nor single-stranded DNA can replicate because they lack an ITR at one termini. Providing the single-stranded DNA with a sequence to that can form a hairpin structure at the 3'-terminus that can serve as a substrate for DNA polymerase will extend the hairpin structure along the entire length of the molecule. This molecule can also serve as a substrate for a DNA polymerase but the product is a duplicated molecule with ITRs at both termini that can replicate in the presence of adenoviral proteins.
Figure 14:
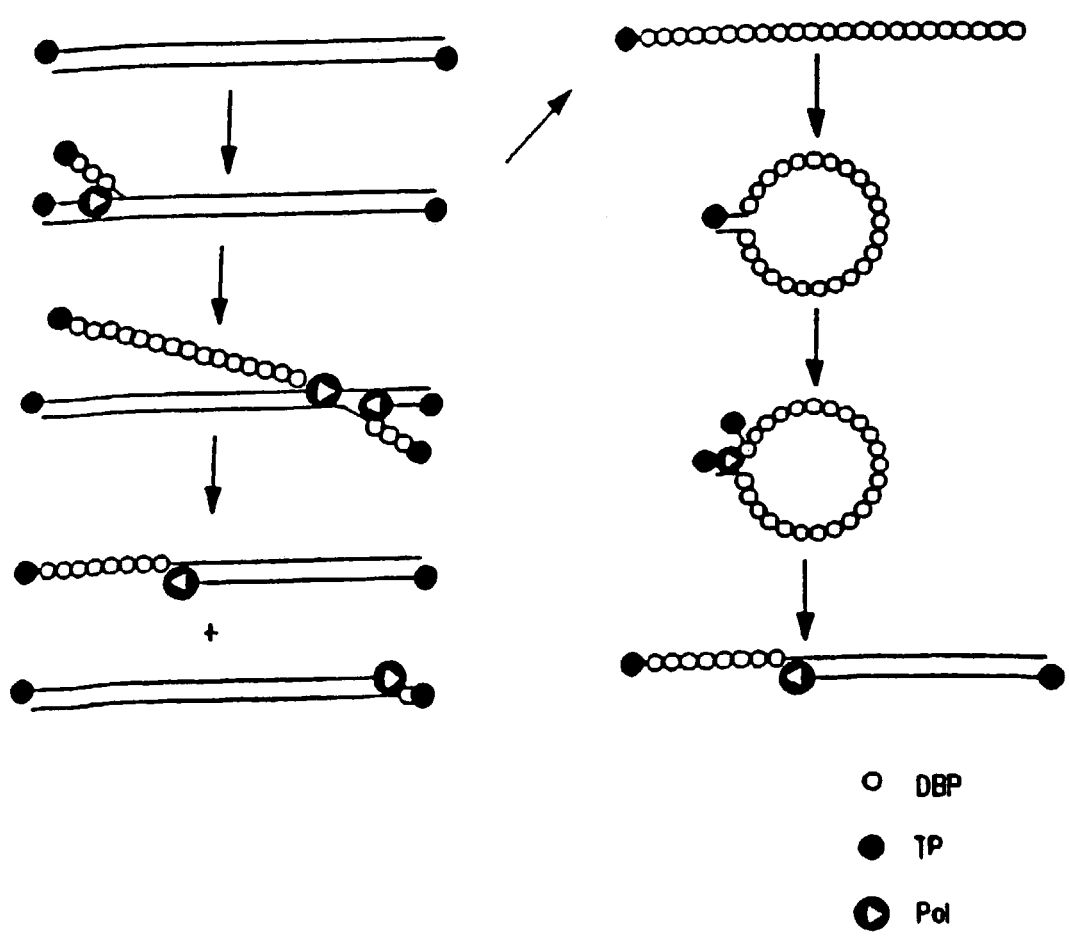
FIG. 14 depicts adenovirus genome replication. The adenovirus genome is shown in the top left. The origins or replication are located within the left and right ITRs at the genome ends. DNA replication occurs in two stages. Replication proceeds from one ITR generating a daughter duplex and a displaced parental single-strand which is coated with adenovirus DNA binding protein (DBP, open circles) and can form a panhandle structure by annealing of the ITR sequences at both termini. The panhandle is a substrate for DNA polymerase (Pol: white arrows) to produce double-stranded genomic DNA. Alternatively, replication proceeds from both ITRs, generating two daughter molecules, thereby, obviating the requirement for a panhandle structure.

Adenovirus-derived DNA fragments that can replicate in suitable cell lines and that may serve as a packaging deficient replicating helper system are generated as follows. These DNA fragments retain at least a portion of the transcribed region of the "late" transcription unit of the adenovirus genome and carry deletions in at least a portion of the E1 region and deletions in at least a portion of the encapsidation signal. In addition, these DNA fragments contain at least one copy of an inverted terminal repeat (IRT). At one terminus of the transfected DNA molecule an ITR is located. The other end may contain an ITR, or alternatively, a DNA sequence that is complementary to a portion of the same strand of the DNA molecule other than the ITR. If, in the latter case, the two complementary sequences anneal, the free 3'-hydroxyl group of the 3' terminal nucleotide of the hairpin structure can serve as a primer for DNA synthesis by cellular and or adenovirus-encoded DNA polymerases, resulting in conversion into a double-stranded form of at least a portion of the DNA molecule. Further replication initiating at the ITR will result in a linear double-stranded DNA molecule, that is flanked by two ITR's, and is larger than the original transfected DNA molecule (see FIG. 13). This molecule can replicate itself in the transfected cell by virtue of the adenovirus proteins encoded by the DNA molecule and the adenoviral and cellular proteins encoded by genes in the host cell genome. This DNA molecule cannot be encapsidated due to its large size (greater than 39,000 base pairs) or due to the absence of a functional encapsidation signal. This DNA molecule is intended to serve as a helper for the production of defective adenovirus vectors in suitable cell lines.

The invention also comprises a method for the amplification of linear DNA fragments of variable size in suitable mammalian cells. These DNA fragments contain at least one copy of the ITR at one of the termini of the fragment. As described above, the other end may contain an ITR, or alternatively, a DNA sequence that is complementary to a portion of the same strand of the DNA molecule other than the ITR. If, in the latter case, the two complementary sequences anneal, the free 3'-hydroxyl group of the 3' terminal nucleotide of the hairpin-structure can serve as a primer for DNA synthesis. This is accomplished by cellular and or adenovirus-encoded DNA polymerases, resulting in conversion of the displaced strand into a doublestranded form of at least a portion of the DNA molecule. Further replication initiation at the ITR will result in a linear double-stranded DNA molecule, that is flanked by two ITR's, which is larger than the original transfected DNA molecule. A DNA molecule that contains ITR sequences at both ends can replicate itself in transfected cells by virtue of the presence of at least the adenovirus E2 proteins (namely the DNA-binding protein (DBP), the adenovirus DNA polymerase (Ad-pol), and the preterminal protein (pTP)). The required proteins may be expressed from adenovirus genes on the DNA molecule itself, from adenovirus E2 genes integrated in the host-cell genome, or from a replicating helper fragment as described above.

Several groups have shown that the presence of ITR sequences at the end of DNA molecules are sufficient to generate adenovirus minichromosomes that can replicate, if the adenovirus-proteins required for replication are provided in trans e.g. by infection with a helper virus (Hu et al, (1992) Gene 110:145–150); (Wang et al, (1985) in vivo. Nucl. Acids Res. 13:5173–5187); Hay et al, (1984) J. Mol. Biol. 174: 493–510). Hu et al, ((1992) Gene 110:145–150), observed the presence and replication of symmetrical adenovirus minichromosome-dimers after transfection of plasmids containing a single ITR. The authors were able to demonstrate that these dimeric minichromosomes arise after tail-to-tail ligation of the single ITR DNA molecules. In DNA extracted from defective adenovirus type 2 particles, dimeric molecules of various sizes have also been observed using electron-microscopy (Daniell (1976) J. Virol. 19:685–708). It was suggested that the incomplete genomes were formed by illegitimate recombination between different molecules and that variations in the position of the sequence at which the illegitimate base pairing occurred were responsible for the heterogeneous nature of the incomplete genomes. Based on this mechanism it was speculated that, in theory, defective molecules with a total length of up to two times the normal genome could be generated. Such molecules could contain duplicated sequences from either end of the genome. However, no DNA molecules larger than the full-length virus were found packaged in the defective particles (Daniell (1976) J. Virol. 19:685–708). This can be explained by the size-limitations that apply to the packaging. In addition, it was observed that in the virus particles DNA-molecules with a duplicated left-end predominated over those containing the right-end terminus (Daniell (1976) J. Virol. 19:685–708). This is fully explained by the presence of the encapsidation signal near that left-end of the genome (Grable et al, (1990) J. Virol. 64:2047–2056; Gräble et al, (1992) J. Virol. 66:723–731; Hearing et al, (1987). J. Virol. 61:2555–2558).

The major problems associated with the current adenovirus-derived vectors are:
a) The strong immunogenicity of the virus particle.
b) The expression of adenovirus genes that reside in the adenoviral vectors, resulting in a Cytotoxic T-cell response against the transduced cells.
c) The low amount of heterologous sequences that can be accommodated in the current vectors (up to maximally approx. 8000 bp. of heterologous DNA).

Ad A) The strong immunogenicity of the adenovirus particle results in an immunological response of the host, even after a single administration of the adenoviral vector. As a result of the development of neutralizing antibodies, a subsequent administration of the virus will be less effective or even completely ineffective. However, a prolonged or persistent expression of the transferred genes will reduce the number of administrations required and may bypass the problem.

Ad B) Experiments performed by Wilson and collaborators have demonstrated that after adenovirus-mediated gene transfer into immunocompetent animals, the expression of the transgene gradually decreases and disappears approximately 2–4 weeks post-infection (Yang et al, (1994a) Proc Natl Acad Sci USA 91:4407–11; Yang et al, (1994b) Nat Genet. 7:362–369). This is caused by the development of a cytotoxic T-cell (CTL) response against the transduced cells. The CTLs were directed against adenovirus proteins expressed by the viral vectors. In the transduced cells synthesis of the adenovirus DNA-binding protein (the E2A-gene product), penton and fiber proteins (late-gene products) could be established. These adenovirus proteins, encoded by the viral vector, were expressed despite deletion of the E1 region. This demonstrates that deletion of the E1 region is not sufficient to completely prevent expression of the viral genes (Engelhardt et al, (1994a) Human Gene Ther. 5:1217–1229).

Ad C) Studies by Graham and collaborators have demonstrated that adenoviruses are capable of encapsidating DNA of up to 105% of the normal genome size (Bett et al, (1993) J. Virol. 67:5911–5921). Larger genomes tend to be instable resulting in loss of DNA sequences during propagation of the virus. Combining deletions in the E1 and E3 regions of the viral genomes increases the maximum size of the foreign that can be encapsidated to approx. 8.3 kb. In addition, some sequences of the E4 region appear to be dispensable for virus growth (adding another 1.8 kb to the maximum encapsidation capacity). Also, the E2A region can be deleted from the vector, when the E2A gene product is provided in trans in the encapsidation cell line, adding another 1.6 kb. However, it is unlikely that the maximum capacity of foreign DNA can be significantly increased further than 12 kb.

We developed a new strategy for the generation and production of helperfree-stocks of recombinant adenovirus vectors that can accommodate up to 38 kb of foreign DNA. Only two functional ITR sequences, and sequences that can function as an encapsidation signal need to be part of the vector genome. Such vectors are called minimal adenovectors. The helper functions for the minimal adenovectors are provided in trans by encapsidation defective-replication competent DNA molecules that contain all the viral genes encoding the required gene products, with the exception of those genes that are present in the host-cell genome, or genes that reside in the vector genome.

The applications of the disclosed inventions are outlined below and are illustrated as follows.

Use of the IG Packaging Constructs Diploid Cells

The constructs, in particular pIG.E1A.E1B, will be used to transfect diploid human cells, such as Human Embryonic Retinoblasts (HER), Human Embryonic Kidney cells (HEK), and Human Embryonic Lung cells (HEL). Transfected cells will be selected for transformed phenotype (focus formation) and tested for their ability to support propagation of E1-deleted recombinant adenovirus, such as IG.Ad.MLPI.TK. Such cell lines will be used for the generation and (large-scale) production of E1-deleted recombinant adenoviruses. Such cells, infected with recombinant adenovirus are also intended to be used in vivo as a local producer of recombinant adenovirus, e.g. for the treatment of solid tumors. 911 cells are used for the titration, generation and production of recombinant adenovirus vectors (Fallaux et al, (1996) *Hum. Gene Ther.* 7:215–222).

HER cells transfected with pIG.E1A.E1B has resulted in 7 independent clones (called PER cells). These clones are used for the production of E1 deleted (including non-overlapping adenovirus vectors) or E1 defective recombinant adenovirus vectors and provide the basis for introduction of e.g. E2B or E2A constructs (e.g. ts125E2A, see below), E4 etc., that will allow propagation of adenovirus vectors that have mutations in e.g. E2A or E4. In addition, diploid cells of other species that are permissive for human adenovirus, such as the cotton rat (*Sigmodon hispidus*) (Pacini et al, (1984) *J. Infect. Dis.* 150:92–97), Syrian hamster (Morin et al, (1987) *Proc. Natl. Acad. Sci. USA* 84:4626–4630) or chimpanzee (Levrero et al, (1991) *Gene* 101:195–202) will be immortalized with these constructs. Such cells, infected with recombinant adenovirus, are also intended to be used in vivo for the local production of recombinant adenovirus, e.g. for the treatment of solid tumors.

Established Cells

The constructs, in particular pIG.E1A.NEO, can be used to transfect established cells, e.g. A549 (human bronchial carcinoma), KB (oral carcinoma), MRC-5 (human diploid lung cell line) or GLC cell lines (small cell lung cancer) de Leij et al, (1985) *Cancer Res.* 45:6024–6033; Postmus et al, (1988) *Eur. J. Clin. Oncol.* 24:753–763) and selected for NEO resistance. Individual colonies of resistant cells are isolated and tested for their capacity to support propagation of E1-deleted recombinant adenovirus, such as IG.Ad.ML-PI.TK. When propagation of E1 deleted viruses on E1A containing cells is possible, such cells can be used for the generation and production of E1-deleted recombinant adenovirus. They are also used for the propagation of E1A deleted/E1B retained recombinant adenovirus.

Established cells can also be co-transfected with pIG.E1A.E1B and pIG.NEO. (or another NEO containing expression vector). Clones resistant to G418 are tested for their ability to support propagation of E1 deleted recombinant adenovirus, such as IG.Ad.MLPI.TK and used for the generation and production of E1 deleted recombinant adenovirus and will be applied in vivo for local production of recombinant virus, as described for the diploid cells (see above).

All cell lines, including transformed diploid cell lines or NEO-resistant established lines, can be used as the basis for the generation of "next generation" packaging cell lines, that support propagation of E1-defective recombinant adenoviruses, that also carry deletions in other genes, such as E2A and E4. Moreover, they will provide the basis for the generation of minimal adenovirus vectors as disclosed herein.

E2 Expressing Cell Lines

Packaging cells expressing E2A sequences are and will be used for the generation and (large scale) production of E2A-deleted recombinant adenovirus. The newly generated human adenovirus packaging cell lines or cell lines derived from species permissive for human adenovirus (E2A or ts125E2A; E1A+E2A; E1A+E1B+E2A; E1A+E2A/ts125; E1A+E1B+E2A/ts125) or non-permissive cell lines such as monkey cells (hrE2A or hr+ts125E2A; E1A+hrE2A; E1A+ E1B+ hrE2A; E1A+hrE2A/ts125; E1A+E1B+hrE2A/ ts125), are and will be used for the generation and (large scale) production of E2A deleted recombinant adenovirus vectors. In addition, they will be applied in vivo for local production of recombinant virus, as described for the diploid cells (see above).

Novel Adenovirus Vectors

The newly developed adenovirus vectors harboring an E1 deletion of nt. 459–3510 will be used for gene transfer purposes. These vectors are also the basis for the development of further deleted adenovirus vectors that are mutated for e.g. E2A, E2B or E4. Such vectors will be generated e.g. on the newly developed packaging cell lines described above (see 1–3).

Minimal Adenovirus Packaging System

We disclose adenovirus packaging constructs (to be used for the packaging of minimal adenovirus vectors) may have the following characteristics:
 a) the packaging construct replicates;
 b) the packaging construct cannot be packaged because the packaging signal is deleted;
 c) the packaging construct contains an internal hairpin-forming sequence (see section "Experimental; suggested hairpin" see FIG. 15);
 d) because of the internal hairpin structure, the packaging construct is duplicated, that is the DNA of the packaging construct becomes twice as long as it was before transfection into the packaging cell (in our sample it duplicates from 35 kb to 70 kb). This duplication also prevents packaging. Note that this duplicated DNA molecule has ITR's at both termini (see e.g. FIG. 13);
 e) this duplicated packaging molecule is able to replicate like a "normal adenovirus" DNA molecule;
 f) the duplication of the genome is a prerequisite for the production of sufficient levels of adenovirus proteins, required to package the minimal adenovirus vector; and/or g) the packaging construct has no overlapping sequences with the minimal vector or cellular sequences that may lead to generation of RCA by homologous recombination.

This packaging system will be used to produce minimal adenovirus vectors. The advantages of minimal adenovirus vectors, e.g. for gene therapy of vaccination purposes, are well, known (accommodation of up to 38 kb; gutting of all potentially toxic and immunogenic adenovirus genes).

Adenovirus vectors containing mutations in essential genes (including minimal adenovirus vectors) can also be propagated using this system.

Use of Intracellular E2-expressing Vectors

Minimal adenovirus vectors are generated using the helper functions provided in trans by packaging-deficient replicating helper molecules. The adenovirus-derived ITR sequences serve as origins of DNA replication in the presence of at least the E2-gene products. When the E2 gene products are expressed from genes in the vector genome (N.B. the gene(s) must be driven by an E1-independent promoter), the vector genome can replicate in the target cells. This will allow a significantly increased number of template molecules in the target cells, and, as a result an increased expression of the genes of interest encoded by the vector. This is of particular interest for approaches of gene therapy in cancer.

Applications of Intracellular Amplification of Linear DNA Fragments

A similar approach could also be taken amplification of linear DNA fragments is desired. DNA fragments of known or unknown sequence could be amplified in cells containing the E2-gene products if at least one ITR sequence is located near or at its terminus. There are no apparent constraints on the size of the fragment. Even fragments much larger than the adenovirus genome (36 kb) should be amplified using this approach. It is thus possible to clone large fragments in mammalian cells without either shuttling the fragment into bacteria (such as *E. coli*) or using the polymerase chain reaction (P.C.R.). At the end stage of a productive adenovirus infection a single cell can contain over 100,000 copies of the viral genome. In the optimal situation, the linear DNA fragments can be amplified to similar levels. Thus, one should be able to extract more than 5 µg of DNA fragment per 10 million cells (for a 35-kbp fragment). This system can be used to express heterologous proteins (equivalent to the Simian Virus 40-based COS-cell system) for research or for therapeutic purposes. In addition, the system can be used to identify genes in large fragments of DNA. Random DNA fragments may be amplified (after addition of ITRs) and expressed during intracellular amplification. Election or selection of those cells with the desired phenotype can be used to enrich the fragment of interest and to isolate the gene.

Gene Correction Vectors

Gene therapy procedures may be divided into two different concepts, i.e., gene addition and gene replacement. Gene addition aims at introducing a therapeutic nucleic acid molecule into somatic cells of a patient, whereby expression of said therapeutic nucleic acid molecule is often under the control of a heterologous promoter and transcription termination signal. For example, when a patient suffers from an inherited disease, a functional copy of the defective nucleic acid molecule responsible for the disease phenotype is introduced into cells of the patient and, upon expression of said therapeutic nucleic acid molecule, the disease phenotype is corrected. Gene addition is, obviously, also used to accomplish expression of otherwise not expressed genes, such as, e.g., cytokine or suicide genes like HSV-TK to treat tumors. The gene replacement procedure aims at repairing at least one copy of a defective gene responsible for a disease phenotype. This can be achieved by introducing a functional version of a gene, or part thereof comprising the mutant site of that gene, in such a way that homologous recombination between said functional version and said defective gene occurs. Consequently, the defective gene or its mutant site is replaced by the functional version of that gene or part thereof. In this way, no nucleic acid material that is foreign to the species of which the patient is a member is expressed in the treated cells but at least one allele of the mutant gene is repaired. For the majority of the inherited diseases it is known that heterozygous carriers are not affected, or at least are affected to a lesser extent than a homozygous patient. Thus, gene replacement may be used for correction of inherited disorders. It is to be understood that this also includes the repair of defective tumor suppressor genes.

For gene therapy purposes, it is preferable to retain the E3 region. E3 containing vectors will be superior to their E3 deleted counterparts because they are able to prevent or reduce host cells responses such as CTL lysis of adenovirus infected cells and cell lysis by TNF.

It will be understood that it may not be necessary to retain the whole E3 region in the vectors according to the invention, as long as the part retained still has the function of reducing the response of the host against infected cells. For example, expression of E3-14.7 kD alone may be sufficient to reduce early responses mediated by TNF (see Ginsberg, H. S. (1989) *Proc. Natl. Acad. Sci, USA* 86:3823–3827; Ginsberg, H. S. (1991) *Proc. Natl. Acad. Sci. USA* 88:1651–1655). These vectors are useful for gene therapy of inherited diseases such as cystic fibrosis, Duchenne molecular dystrophy, Hypercholesterolemia, blood clotting disorders (hemophilia) and the like. They also are useful in the therapy of acquired diseases, such as tumors, hepatitis, (auto) immune diseases, restenosis, rheumatoid and the like.

Advantages of gene replacement over gene addition include (1) expression regulation of the replacing gene is identical to the endogenous expression pattern, and (2) the procedure is safe, because no risk exists of insertion mutagenesis due to random integration.

The following examples are presented as illustrations, not limitations.

EXAMPLES

Example 1

Generation of Cell Lines Able to Transcomplement E1 Defective Recombinants Adenovirus Vectors 1. 911 Cell Line A cell line that harbors E1 sequences of adenovirus type 5, able to trans-complement E1 deleted recombinant adenovirus has been generated, (Fallaux et al, (1996) *Hum. Gene Ther.* 7:215–222). This cell line was obtained by transfection of human diploid human embryonic retinoblasts (HER) with pAd5XhoIC, that contains nt. 80–5788 of Ad5; one of the resulting transformants was designated 911. This cell line has been shown to be useful in the propagation of E1 defective recombinant adenovirus. It was found to be superior to the 293 cells. Unlike 293 cells, 911 cells lack a fully transformed phenotype, which most likely is the cause of performing better as adenovirus packaging line. For example, plaque assays can be performed faster (4–5 days instead of 8–14 days on 293) monolayers of 911 cells survive better under agar overlay as required for plaque assays higher amplification of E1 -deleted vectors. In addition, unlike 293 cells that were transfected with sheared adenoviral DNA, 911 cells were transfected using a defined construct. Transfection efficiencies of 911 cells are comparable to those of 293.

New Packaging Constructs

1. Source of Adenovirus Sequences

Adenovirus sequences are derived either from pAd5.SalB, containing nt.80–9460 of human adenovirus type 5 (Bernards et al, (1983) *Virology* 127:45–53) or from wild-type Ad5 DNA. PAd5.SalB was digested with SalI and XhoI and the large fragment was religated and this new clone was named pAd5.X/S. The pTN construct (constructed by Dr. R. Vogels, IntroGene, The Netherlands) was used as a source for the human PGK promoter and the NEO gene.

2. Human PGK Promoter and $NEO^R$ Gene

Transcription of E1A sequences in the new packaging constructs is driven by the human PGK promoter (Michelson et al, (1983) *Proc. Natl. Acad. Sci. USA* 80:472–476); Singer-Sam et al, (1984) *Gene* 32:409–417), derived from plasmid pTN (gift of R. Vogels), which uses pUC119 (Vieira et al, (1987) pp. 3–11: *Methods in Enzymology*, Acad. Press Inc.) as a backbone. This plasmid was also used as a source for the NEO gene fused to the Hepatitis B Virus (HBV) poly-adenylation signal.

3. Fusion of PGK Promoter to E1 Genes (FIG. 1)

In order to replace the E1 sequences of Ad5 (ITR, origin of replication and packaging signal) by heterologous sequences we have amplified E1 sequences (nt.459 to nt.960) of Ad5 by PCR, using primers Ea1 and Ea2 (see Table I). The resulting PCR product was digested with ClaI and ligated into Bluescript (Stratagene), predigested with ClaI and EcoRV, resulting in construct pBS.PCRI.

Vector pTN was digested with restriction enzymes EcoRI (partially) and ScaI, and the DNA fragment containing the PGK promoter sequences was ligated into PBS.PCRI digested with ScaI and EcoRI. The resulting construct PBS.PGK.PCRI contains the human PGK promoter operatively linked to Ad5 E1 sequences from nt.459 to nt.916.

Figure 2:
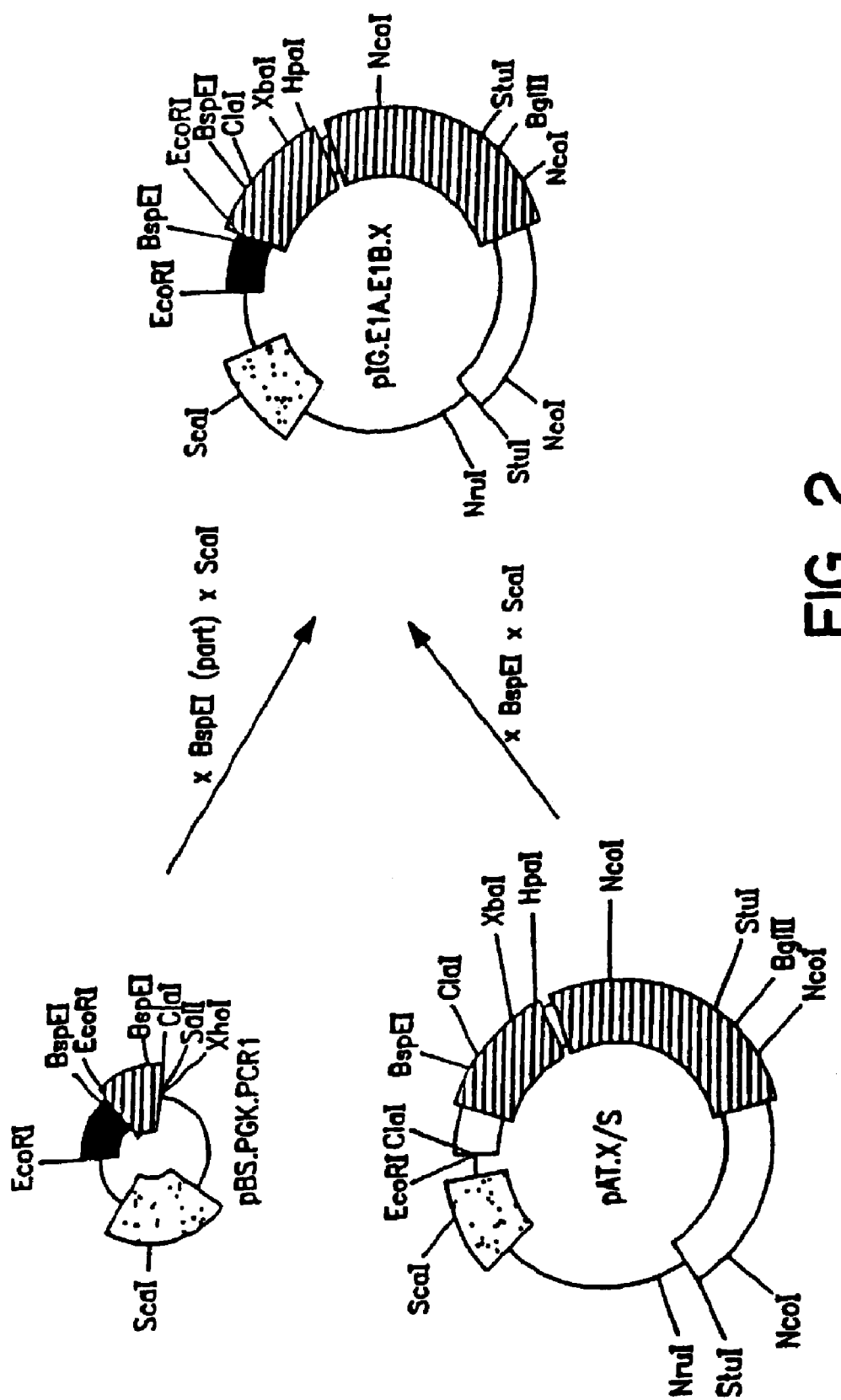
FIG. 2 depicts construction of pIG.E1A.E1B.X. pIG.E1A.E1B.X encodes Ad5 nucleotides 459–5788 (E1A and E1B regions) operatively linked to the human PGK promoter. pIG.E1A.E1B.X also encodes Ad5 pIX protein. pIG.E1A.E1B.X was constructed by replacing the Sca I-BspE I fragment of pAT-X/S with the corresponding fragment of pBS.PGK.PCRI.

4. Construction of pIG.E1A.E1B (FIG. 2)

PIG.E1A.E1B.X contains the E1A and E1B coding sequences under the direction of the PGK promoter. As Ad5 sequences from nt.459 to nt.5788 are present in this construct, also pIX protein of adenovirus is encoded by this plasmid. pIG.E1A.E1B.X was made by replacing the ScaI-BspE1 fragment of pAT-X/S by the corresponding fragment from PBS.PGK.PCRI (containing the PGK promoter linked to E1A sequences).

5. Construction of PIG.E1A.NEO (FIG. 3)

In order to introduce the complete E1B promoter and to fuse this promoter in such a way that the AUG codon of E1B 21 kD exactly functions as the AUG codon of $NEO^R$, the E1B promoter was amplified using primers Ea3 and Ep2, where primer Ep2 introduces a NcoI site in the PCR fragment. The resulting PCR fragment, named PCRII, was digested with HpaI and NcoI and ligated into pAT-X/S, which was predigested with HpaI and with Nco. The resulting plasmid was designated pAT-X/S-PCR2. The NcoI-StuI fragment of pTN, containing the NEO gene and part of the Hepatitis B Virus (HBV) poly-adenylation signal, was cloned into pAT-X/S-PCR2 which had been digested with NcoI and NruI. The resulting construct was, pAT-PCR2-NEO. The poly-adenylation signal was completed by replacing the ScaI-SalI fragment of pAT-PCR2.NEO with the corresponding fragment of pTN, resulting in pAT.PCR2.NEO.p (A). The ScaI-XbaI of pAT.PCR2.NEO.p (A) was replaced with the corresponding fragment of pIG.E1A.E1B-X, containing the PGK promoter linked to E1A genes. The resulting construct was named pIG.E1A.NEO, and thus contains Ad5 E1 sequences (nt.459 to nt.1713) under the control of the human PGK promoter.

Figure 4:
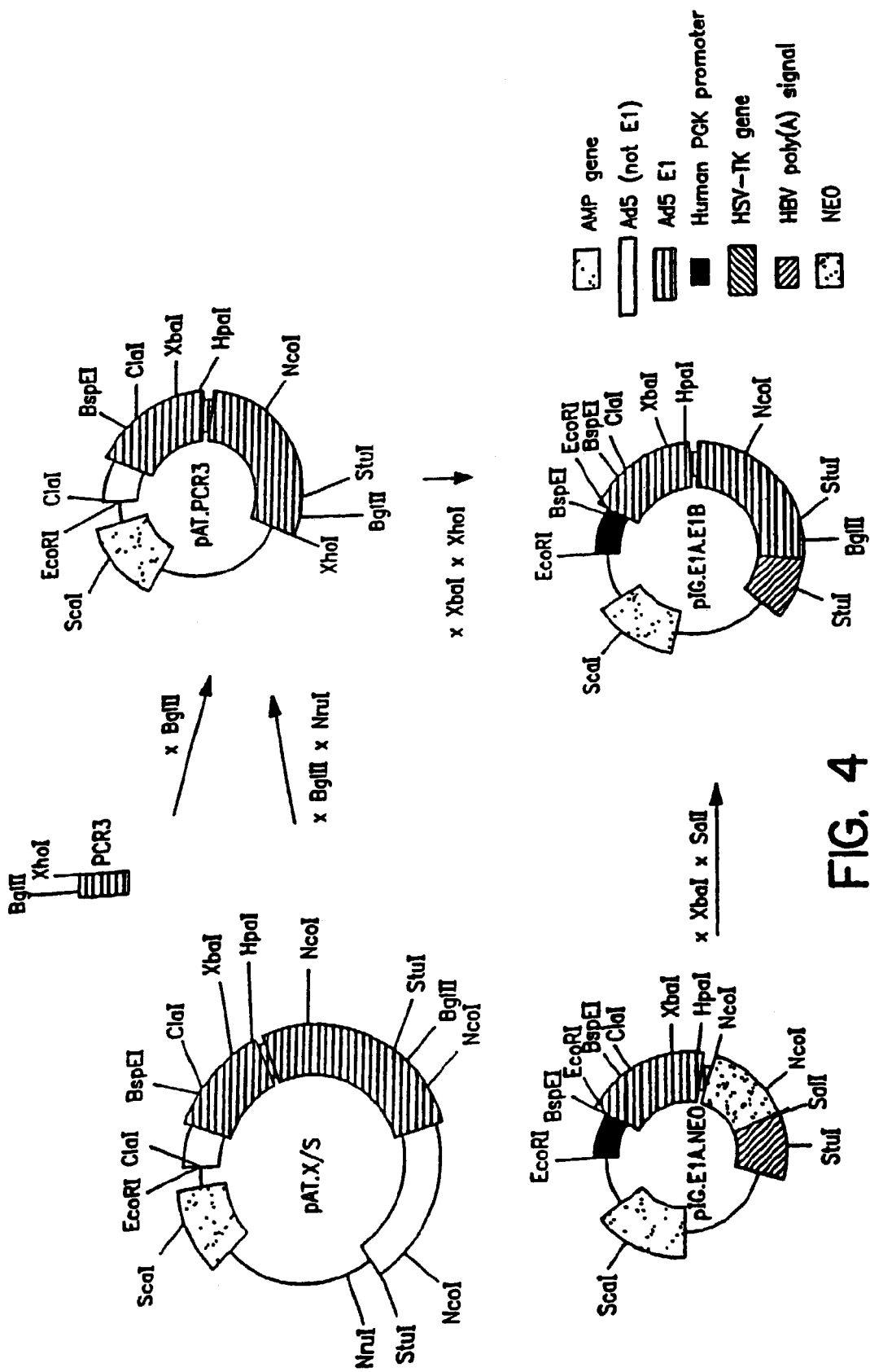
FIG. 4 depicts construction of pIG.E1A.E1B. pIG.E1A.E1B contains the Ad5 nucleotides 459–3510 (E1A and E1B proteins) operatively linked to the PGK promoter and HBV poly(A) signal. This plasmid was constructed by PCR amplification of the N-terminal amino acids of the E1B 55 kD protein with primers Eb-1 and Eb-2, which introduces an Xho I site, digested with Bgl II and cloned into the Bgl II-Nru I sites of pAT-X S, producing pAT-PCR3. The Xba I-Xho I fragment of pAT-PCR3 was replaced with the Xba I-Sal I fragment (containing the HBV poly(A) site) of pIG.E1A.NEO to produce pIG.E1A.E1B.

6. Construction of pIG.E1A.E1B (FIG. 4)

pIG.E1A.E1B contains nt.459 to nt.3510 of Ad5, that encode the E1A and E1B proteins. The E1B sequences are terminated at the splice acceptor at nt.3511. No pIX sequences are present in this construct.

pIG.E1A.E1B was made as follows: The sequences encoding the N-terminal amino acids of E1B 55 kd were amplified using primers Eb1 and Eb2 which introduces a XhoI site. The resulting PCR fragment was digested with BglII and cloned into BlII/NruI of pAT-X/S, thereby obtaining pAT-PCR3. The HBV poly (A) sequences of pIG.E1A.NEO were introduced downstream of the E1B sequences of pAT-PCR3 by exchange of the Xba-SalI fragment of pIG.E1A.NEO and the XbaI XhoI fragment of pAT.PCR3.

TABLE I

Primers used for PCR amplification of DNA fragments used for generation of constructs described in this patent application.

| | | | |
|---|---|---|---|
| Ea-1 | CGTGTAGTGTATTTATACCCG | (SEQ ID NO:27) | PCR amplification Ad5 nt.459 -> |
| Ea-2 | TCGTCACTGGGTGGAAAGCCA | (SEQ ID NO:28) | PCR amplification Ad5 nt.960 <- |
| Ea-3 | TACCCGCCGTCCTAAAATGGC | (SEQ ID NO:29) | nt.1284-1304 of Ad5 genome |
| Ea-5 | TGGACTTGAGCTGTAAACGC | (SEQ ID NO:30) | nt.1514-1533 of Ad5 genome |
| Ep-2 | GCCTCCATGGAGGTCAGATGT | (SEQ ID NO:31) | nt.1721-1702 of Ad5; introduction of NcoI site |
| Eb-1 | GCTTGAGCCCGAGACATGTC | (SEQ ID NO:32) | 34 nt.3269-3289 of Ad5 genome |

TABLE I-continued

Primers used for PCR amplification of DNA fragments used for
generation of constructs described in this patent application.

| | | | |
|---|---|---|---|
| Eb-2 | CCCCTCGAGCTCAATCTGTATCTT | (SEQ ID NO:33) | nt.3508-3496 of Ad5 genome; introduction of XhoI site |
| SV40-1 | GGGGGATCCGAACTTGTTTATTGCAGC | (SEQ ID NO:34) | introduction BamHI site (nt.2182-2199 of pMLP.TK) adaption of recombinant adenoviruses |
| SV40-2 | GGGAGATCTAGACATGATAAGATAC | (SEQ ID NO:35) | introduction BglII site (nt.2312-2297 of pMLP.TK) |
| Ad5-1 | GGGAGATCTGTACTGAAATGTGTGGGC | (SEQ ID NO:36) | introduction BglII site (nt.2496-2514 of pMLP.TK) |
| Ad5-2 | GGAGGCTGCAGTCTCCAACGGCGT | (SEQ ID NO:37) | nt.2779-2756 of pMLP.TK |
| ITR1 | GGGGGATCCTCAAATCGTCACTTCCGT | (SEQ ID NO:38) | nt.35737-35757 of Ad5 (introduction of BamHI site |
| ITR2 | GGGGTCTAGACATCATCAATAATATAC | (SEQ ID NO:39) | nt.35935-35919 of Ad5 (introduction of XbaI site) |

PCR primer sets to be used to create the SalI and Asp718 sites juxtaposed to the ITR sequences.

PCR/MLP1 GGCGAATTCGTCGACATCATCAATAATATACC (SEQ ID NO:40)
    (Ad5. nt. 10-18)

PCR/MLP2 GGCGAATTCGGTACCATCATCAATAATATACC (SEQ. ID NO:41)
    (Ad5 nt.10-18)

PCR/MLP3 CTGTGTACACCGGCGCA (SEQ ID NO:42)
    (Ad5 nt.200-184)

Synthetic oligonucleotide pair used to generate a synthetic hairpin, recreates an Asp718 site at one
of the termini if inserted in Asp718 site:

HP/asp1 5'-GTACACTGACCTAGTGCCGCCCGGGAAAGCCCGGGCGGCACTAGGTCAG    (SEQ ID NO:43)

HP/asp2 5'-GTACCTGACCTAGTGCCGCCCGGGCTTTGCCCGGGCGGCACTAGGTCAGT    (SEQ ID NO:44)

Synthetic oligonucleotide pair used to generate a synthetic hairpin, contains the ClaI recognition
site to be used for hairpin formation.

HP/cla1 5'-GTACATTGACCTAGTGCCGCCCGGGCAAAGCCCGGGCGGCACTAGGTCAATCGAT   (SEQ ID NO:45)

HP/cla2 5'-GTACATCGATTGACCTAGTGCCGCCCGGGTTTGCCCGGGCGGCACTAGGTCAAT    (SEQ ID NO:46)

Figure 5:
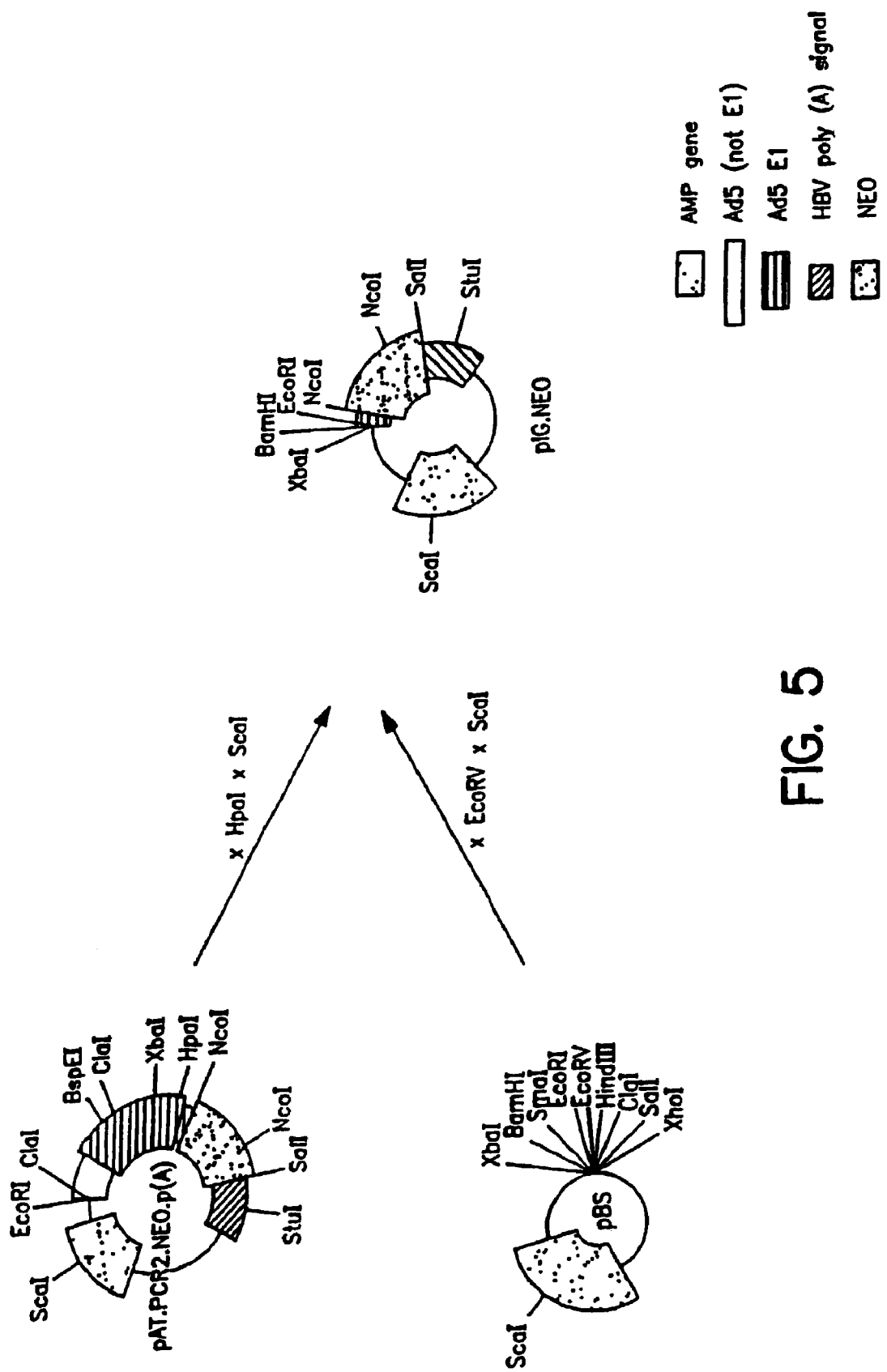
FIG. 5 depicts construction of pIG.NEO. pIG.NEO contains the Neo$^R$ operatively linked to the E1B promoter. pIG.NEO was constructed by ligating the Hpa I-Sca I fragment of pIG.E1A.NEO which contains the E1B promoter and Neo$^R$ into the EcoR V-Sca I sites of pBS.

7. Construction of pIG.NEO (FIG. 5)

This construct is of use when established cells are transfected with E1A.E1B constructs and NEO selection is required. Because NEO expression is directed by the E1B promoter, NEO resistant cells are expected to co-express. E1A, which also is advantageous for maintaining high levels of expression of E1A during long-term culture of the cells. pIG.NEO was generated by cloning the HpaI-ScaI fragment of pIG.E1A.NEO, containing the NEO gene under the control of the Ad5 E1B promoter, into pBS digested with EcoRV and ScaI.

Testing of Constructs

The integrity of the constructs pIG.E1A.NEO, pIG.E1A.E1B.X and pIG.E1A.E1B was assessed by restriction enzyme mapping; furthermore, parts of the constructs that were obtained by PCR analysis were confirmed by sequence analysis. No changes in the nucleotide sequence were found.

The constructs were transfected into primary BRK (Baby Rat Kidney) cells and tested for their ability to immortalize (pIG.E1A.NEO) or fully transform (pAd5.XhoIC, pIG.E1A.E1B.X and pIG.E1A.E1B) these cells. Kidneys of 6-day old WAG-Rij rats were isolated, homogenized and trypsinized. Subconfluent dishes (diameter 5 cm) of the BRK cell cultures were transfected with 1 or 5 µg of pIG.NEO, pIG.E1A.NEO, pIG.E1A.E1B, pIG/E1A.E1B.X, pAd5XhiIC, or with pIG.E1A.NEO together with PDC26 (Elsen et al, (1983) *Virology* 128:377–390), carrying the Ad5.E1B gene under control of the SV40 early promoter. Three weeks post-transfection, when foci were visible, the dishes were fixed, Giemsa stained, and the foci counted.

Figure 6:
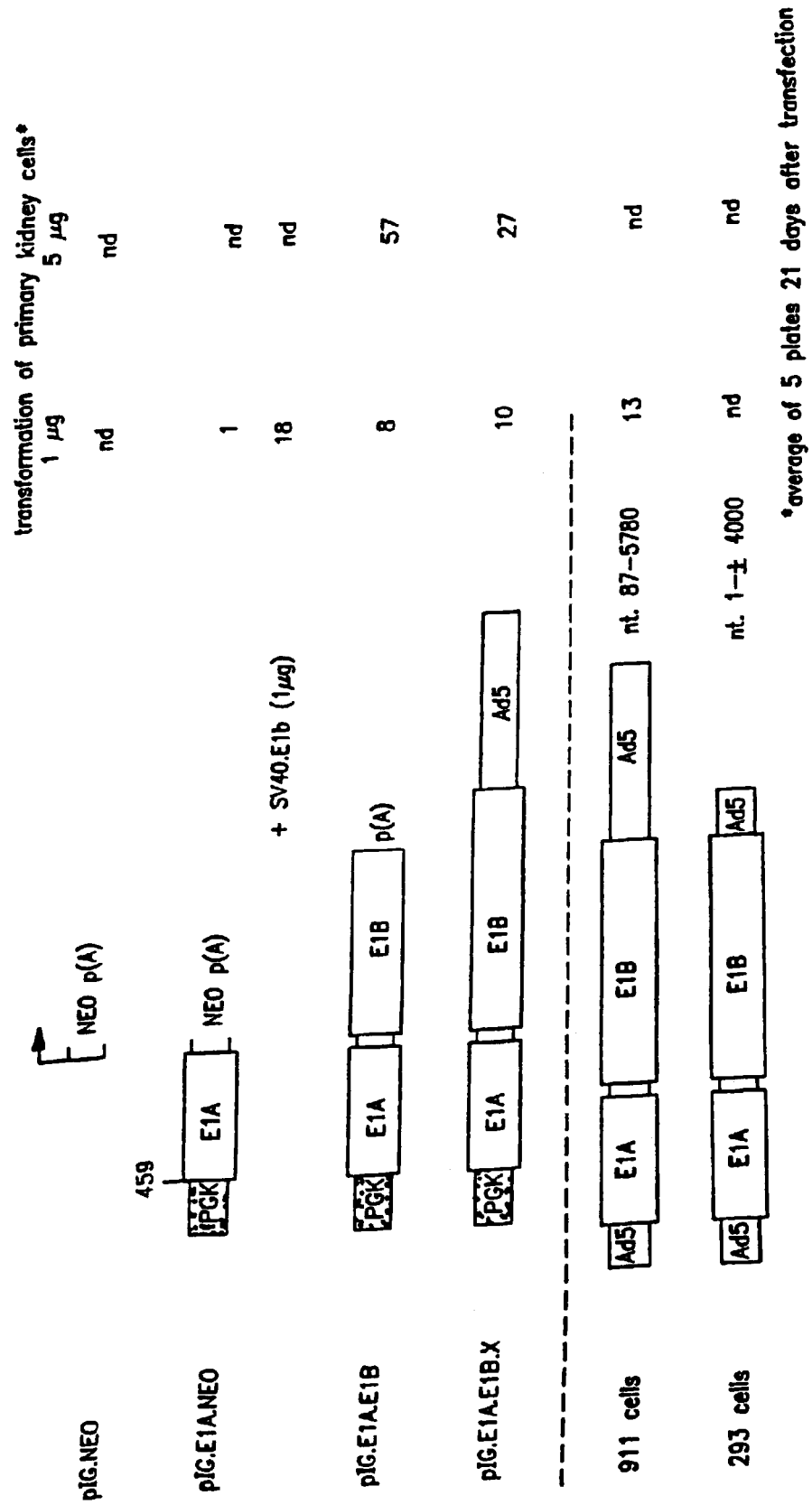
FIG. 6 graphically portrays transformation of primary baby rat kidney (BRK) cells by adenovirus packaging constructs. Subconfluent dishes of BRK cells were transfected with 1 or 5 µg of with either pIG.NEO, pIG.E1A.NEO, pIG.E1A.E1B, pIG.E1A.E1B.X, pAd5XhoIC, or pIG.E1A.NEO plus pDC26, which expresses the Ad5 E1B gene under control of the SV40 early promoter. Three weeks post-transfection, foci were visible, cells were fixed, Giemsa stained and the foci counted. The results shown are the average number of foci per 5 replicate dishes.

An overview of the generated adenovirus packaging constructs, and their ability to transform BRK, is presented in FIG. 6. The results indicate that the constructs pIG.E1A.E1B and pIG.E1A.E1B.X are able to transform BRK cells in a dose-dependent manner. The efficiency of transformation is similar for both constructs and is comparable to what was found with the construct that was used to make 911 cells, namely pAd5.XhoIC.

As expected, pIG.E1A.NEO was hardly able to immortalize BRK. However, co-transfection of an E1B expression construct (PDC26) did result in a significant increase of the number of transformants (18 versus 1), indicating that the E1A encoded by pIG.E1A.NEO is functional. We conclude therefore, that the newly generated packaging constructs are suitable for the generation of new adenovirus packaging lines.

Generation of Cell Lines with New Packaging Constructs Cell Lines and Cell Culture Human A549 bronchial carcinoma cells (Shapiro et al, (1978) *Biochem. Biophys. Acta* 530:197–207), human embryonic retinoblasts (HER), Ad5-E1-transformed human embryonic kidney (HEK) cells (293; Graham et al, (1977) *J. Gen. Virol.* 36:59–72) and Ad5-transformed HER cells (911; Fallaux et al, (1996) *Hum. Gene Ther.* 7:215–222) and PER cells were grown, in Dulbecco's Modified Eagle Medium (DMEM) supplemented with 10% Fetal Calf Serum (FCS) and antibiotics in a 5% CO2 atmosphere at 37° C. Cell culture media, reagents and sera were purchased from Gibco Laboratories (Grand Island, N.Y.). Culture plastics were purchased from Greiner (Nürtingen, Germany) and Corning (Corning, N.Y.).

Viruses and Virus Techniques

The construction of recombinant adenoviral vectors IG.Ad.MLP.nls.lacZ, IG.Ad.MLP.luc, IG.Ad.MLP.TK and IG.Ad.CMV.TK is described in detail in patent application EP 95202213. The recombinant adenoviral vector IG.Ad.MLP.nls.lacZ contains the *E. coli* lacZ gene, encoding β-galactosidase, under control of the Ad2 major late promoter (MLP), IG.Ad.MLP.luc contains the firefly luciferase gene drive by the Ad2 MLP, and adenoviral vectors IG.Ad.MLP.TK and IG.Ad.CMV.TK contain the Herpes Simplex Virus thymidine kinase (TK) gene under the control of the Ad2 MLP and the Cytomegalovirus (CMV) enhancer/promoter, respectively.

Transfections

All transfections were performed by calcium-phosphate precipitation DNA (Graham et al, (1973) *Virology* 52:456–467) with the GIBCO Calcium Phosphate Transfection System (GIBCO BRL Life Technologies, Inc., Gaithersburg, USA), according to the manufacturer's protocol.

Western Blotting

Subconfluent cultures of exponentially growing 293, 911 and Ad5-E1-transformed A549 and PER cells were washed with PBS and scraped in Fos-RIPA buffer (10 mM Tris (pH 7,5),150 mM NaCl, 1% NP40,01 % sodium dodecyl sulfate (SDS), 1% NA-DOC, 0.5 mM phenyl methyl sulfonyl fluoride (PMSF), 0.5 mM trypsin inhibitor,50 mM NaF and 1 mM sodium vanadate). After 10 min. at room temperature, lysates were cleared by centrifugation. Protein concentrations were measured with the BioRad protein assay kit, and 25 µg total cellular protein was loaded on a 12.5% SDS-PAA gel. After electrophoresis, proteins were transferred to nitrocellulose (1 h at 300 mA). Prestained standards (Sigma, USA) were run in parallel. Filters were blocked with 1% bovine serum albumin (BSA) in TBST (10 mM Tris, pH 8, 15 mM NaCl, and 0.05% Tween-20) for 1 hour. First antibodies were the mouse monoclonal anti-Ad5-E1B-55-kDA antibody A1C6 (Zantema et al, unpublished) and the rat monoclonal anti-Ad5-E1B-221-kDa antibody C1G11I (Zantema et al, (1985) *Virology* 142:44–58). The second antibody was a horseradish peroxidase-labeled goat anti-mouse antibody (Promega). Signals were visualized by enhanced chemoluminescence (Amersham Corp. UK).

Southern Blot Analysis

High molecular weight DNA was isolated and 10 µg were digested to completion and fractionated on a 0.7% agarose gel. Southern blot transfer to Hybond N+(Amersham, UK) was performed with a 0.4 M NAOH, 0.6 M NaCl transfer solution (Church and Gilbert, 1984). Hybridization was performed with a 2463-nt SspI-HindIII fragment from pAd5.SalB (Bernards et al, (1983) *Virology* 127:45–53). This fragment consists of Ad5 bp. 342–2805. The fragment was radiolabeled with $\alpha^{-32P}$=dCTP with the use of random hexanucleotide primers and Kelnow DNA polymerase. The Southern blots were exposed to a Kodak XAR-5 film at −80° C. and to a Phospho-Imager screen which was analyzed by B&L systems Molecular Dynamics Software.

A549

Ad5-E1 -transformed A549 human bronchial carcinoma cell lines were generated by transfection with pIG.E1A.NEO and selection for G418 resistance. Thirty-one G418 resistant clones were established. Co-transfection of pIG.E1A.E1B with pIG.NEO yielded seven G418 resistant cell lines.

PER

Ad5-E1-transformed human embryonic retina (HER) cells, were generated by transfection of primary HER cells with plasmid pIG.E1A.E1B. Transformed cell lines were established from well-separated foci. We were able to establish seven clonal cell lines, which we called PER.C1, PER.C3, PER.C4, PER.C5, PER.C6, PER.C8 and PER.C9. One of the PER clones, namely PER.C6, has been deposited at the ECACC under number 96022940.

Expression of Ad5 E1A and E1B Genes in Transformed A549 and PER Cells

Figure 7:
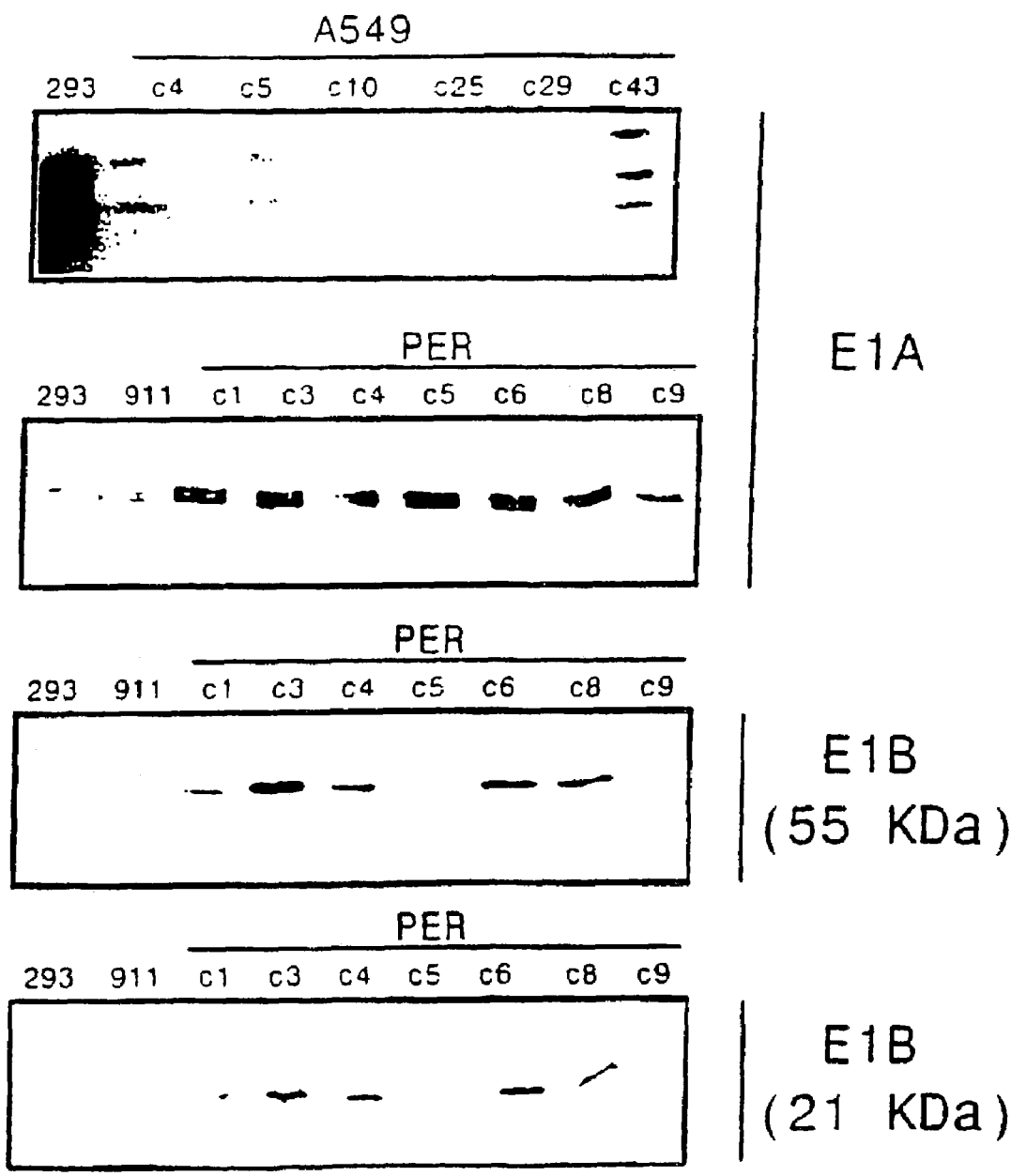
FIG. 7 is a Western blot analysis of A549 clones transfected with pIG.E1A.NEO and human embryonic retinoblasts (HER cells) transfected with pIG.E1A.E1B (PER clones). Expression of Ad5 E1A and E1B 55 kD and 21 kD proteins in transfected A549 cells and PER cells was determined by Western blot with mouse monoclonal antibodies (Mab) M73 which recognizes E1A gene products and Mabs AIC6 and C1G11, which recognize the E1B 55 kDa and 21 kDa proteins, respectively. Mab binding was visualized using horseradish peroxidase-labeled goat anti-mouse antibody and enhanced chemiluminesence. 293 and 911 cells served as controls.

Expression of the Ad5 E1A and the 55-kDa and 21 kDa E1B proteins in the established A549 and PER cells was studied by means of Western blotting, with the use of monoclonal antibodies (mAb). mAb M73 recognizes the E1A products, whereas Mabs A1C6 and, CIGll are directed against the 55-kDa and 21 kDa E1B proteins, respectively. The antibodies did not recognize proteins in extracts from the parental A549 or the primary HER cells (data not shown). None of the A549 clones that were generated by co-transfection of pIG.NEO and pIG.E1A.E1B expressed detectable levels of E1A or E1B proteins (not shown). Some of the A549 clones that were generated by transfection with PIG.E1A.NEO expressed the Ad5 E1A proteins (FIG. 7), but the levels were much lower than those detected in protein lysates from 293 cells. The steady state E1A levels detected in protein extracts from PER cells were much higher than those detected in extracts from A549-derived cells. All PER cell lines expressed similar levels of E1A proteins (FIG. 7). The expression of the E1B proteins, particularly in the case of E1B 55 kDa, was more variable. Compared to 911 and 293, the majority of the PER clones express high levels of E1B 55 kDa and 2 kDa. The steady state level of E1B 21 kDa was the highest in PER.C3. None of the PER clones lost expression of the Ad5 E1 genes upon serial passage of the cells (not shown). We found that the level of E1 expression in PER cells remained stable for at least 100 population doublings. We decided to characterize the PER clones in more detail.

Southern Analysis of PER Clones

To study the arrangement of the Ad5-E1 encoding sequences in the PER clones we performed Southern analyses. Cellular DNA was extracted from all PER clones, and from 293 and 911 cells. The DNA was digested with HindIII, which cuts once in the Ad5 E1 region. Southern hybridization on HindIII-digested DNA, using a radiolabeled Ad5-

Figure 8:
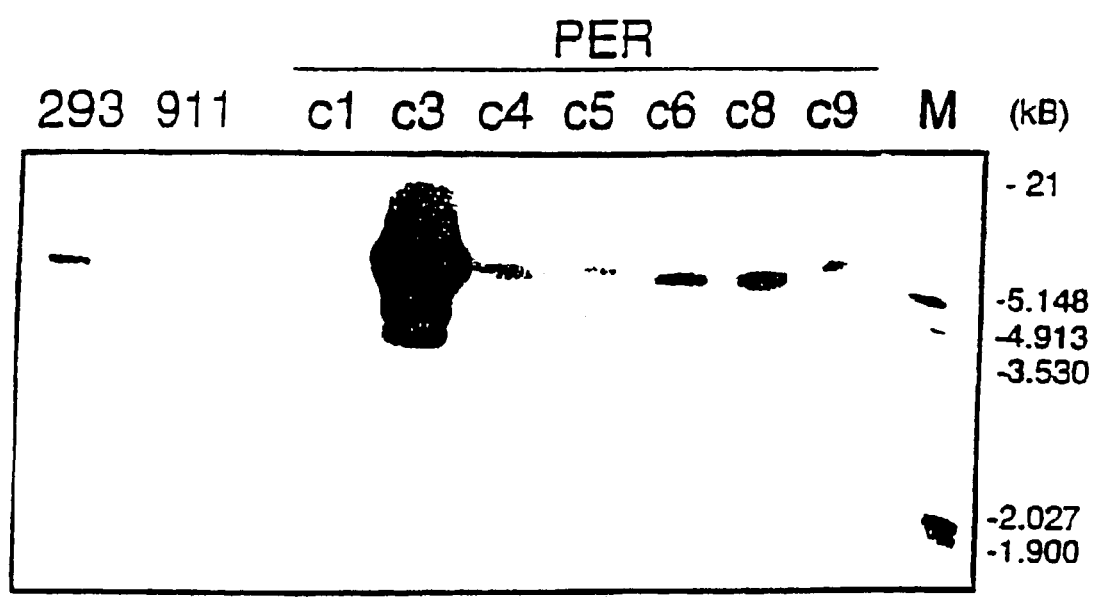
FIG. 8 is a Southern blot analysis of 293, 911 and PER cell lines. Cellular DNA was extracted, Hind III digested, electrophoresed and transferred to Hybond N+ membranes (Amersham). Membranes were hybridized to radiolabeled probes generated by random priming of the Ssp I-Hind in fragment of pAd5.SalB (Ad5 nucleotides 342–2805).

E1-specific probe, revealed the presence of several integrated copies of pIG.E1A.E1B in the genome of the PER clones. FIG. 8 shows the distribution pattern of E1 sequences in the high molecular weight DNA of the different PER cell lines. The copies are concentrated in a single band, which suggests that they are integrated as tandem repeats. In the case of PER.C3, C5, C6 and C9,we found additional hybridizing bands of low molecular weight that indicate the presence of truncated copies of pIG.E1A.E1B. The number of copies was determined with the use of a Phospho-Imager. We estimated that PER.C1, C3, C4, C5, C6, C8 and C9 contain 2, 88, 5, 4, 5, 5, and 3 copies of the Ad5 E1 coding region, respectively, and that 911 and 293 cells contain 1 and 4 copies of the Ad5 E1 sequences, respectively.

Transfection Efficiency

Figure 9:
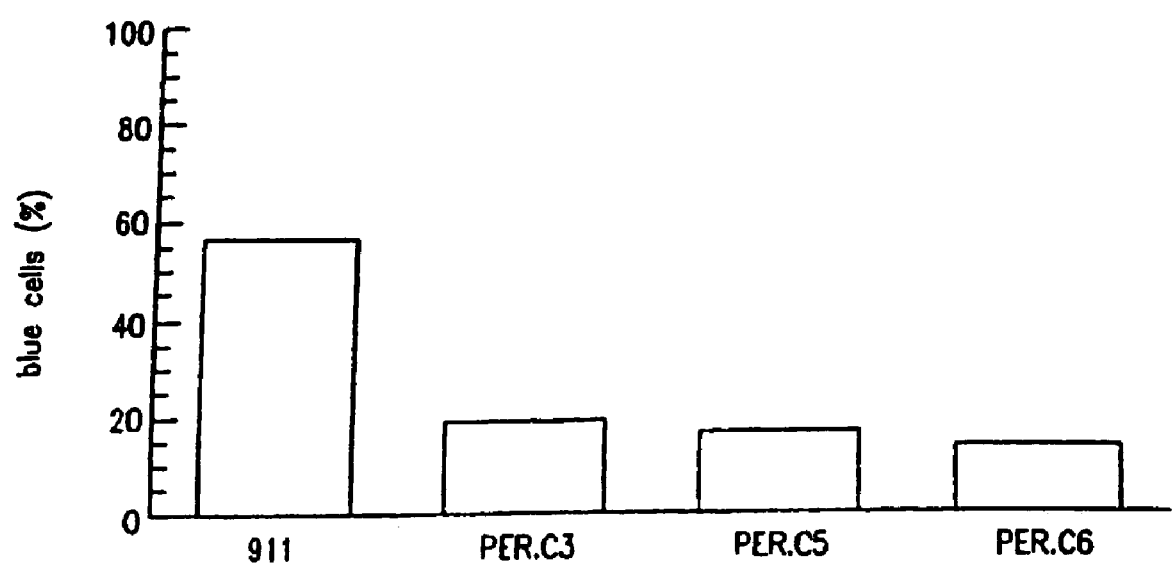
FIG. 9 illustrates the transfection efficiency of PER.C3, PER.C5, PER.C6 and 911 cells. Cells were cultured in 6-well plates and transfected in duplicate with 5 µg pRSV-.lacZ by calcium-phosphate co-precipitation. Forty-eight hours post-transfection, cells were stained with X-Gal and blue cells were counted. Results shown are the mean percentage of blue cells per well.

Recombinant adenovectors are generated by co-transfection of adaptor plasmids and the large ClaI fragment of Ad5 into 293 cells (EP application-95202213). The recombinant virus DNA is formed by homologous recombination between the homologous viral sequences that are present in the plasmid and the adenovirus DNA. The efficacy of this method, as well as that of alternative strategies, is highly dependent on the transfectability of the helper cells. Therefore, we compared the transfection efficiencies of some of the PER clones with 911 cells, using the E. coli β-galactosidase-encoding lacZ gene as a reporter (FIG. 9).

Production of Recombinant Adenovirus

Yields of recombinant adenovirus obtained after inoculation of 293, 911 ,PER.C3, PER.C5 and PER.C6 with different adenovirus vectors are presented in Table II.

The results indicate that the recombinant adenovirus vector yields obtained with PER cells are at least as high as those obtained with the existing celllines. In addition, the yields of the novel adenovirus vector IG.Ad.MLPI.TK are similar or higher than the yields obtained for the other viral vectors on all cell lines tested.

Figure 10:
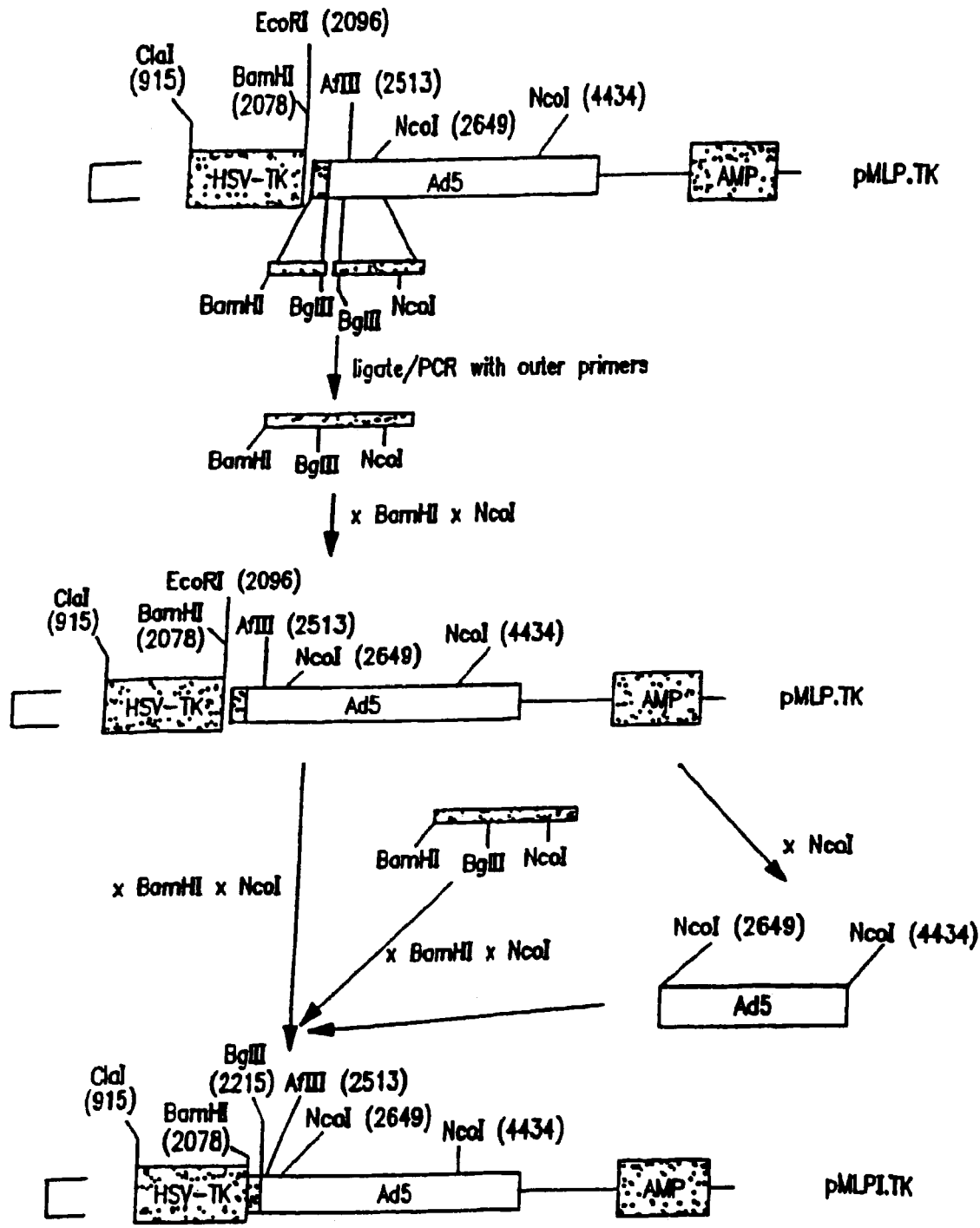
FIG. 10 depicts the construction of adenovirus vector, pMLPI.TK. pMLPI.TK was designed to have no sequence overlap with the packaging construct pIG.E1A.E IB. pMLPI.TK was derived from pMLP.TK by deletion of the region of sequence overlap with pIG.E1A.E1B and deletion of non-coding sequences derived from lacZ. SV40 poly(A) sequences of pMLP.TK were PCR amplified with primers SV40-1, which introduces a BamH I site and SV40-2, which introduces a Bgl II site. pMLP.TK Ad5 sequences 2496 to 2779 were PCR amplified with primers Ad5-1, which introduces a Bgl.II site and Ad5-2. Both PCR products were Bgl II digested, ligated, and PCR amplified with primers SV40-1 and Ad5-2. This third PCR product was BamH I and Afl III digested and ligated into the corresponding sites of pMLP.TK, producing pMLPI.TK.

Generation of New Adenovirus Vectors (FIG. 10)

The recombinant adenovirus vectors used (see patent application EP 95202213) are deleted for E1 sequences from 459 to nt. 3328.As construct pE1A.E1B contains Ad5 sequences 459 to nt.3510 there is a sequence overlap of 183 nt. between E1B sequences in the packaging construct pIG.E1A.E1B and recombinant adenoviruses, such as IG.Ad.MLP.TK. The overlapping sequences were deleted from the new adenovirus vectors. In addition, non-coding sequences derived from lacZ, that are present in the original constructs, were deleted as well. This was achieved (see FIG. 10) by PCR amplification of the SV40 poly (A) sequences from pMLP.TK using primers SV40-1 (introduces a BamHI site) and SV40-2 (introduces a BglII site). In addition, Ad5 sequences present in this construct were amplified from nt. 2496 (Ad5, introduces a BglII site) to nt: 2779 (Ad5-2). Both PCR fragments were digested with BglII and were ligated. The ligation product was PCR amplified using primers SV40-1 and Ad5-2. The PCR product obtained was cut with BamHI and AflII and was ligated into pMLP.TK predigested with the same enzymes. The resulting construct, named pMLPI.TK, contains a deletion in adenovirus E1 sequences from nt.459 to nt. 3510.

Packaging System

Figure 11A:
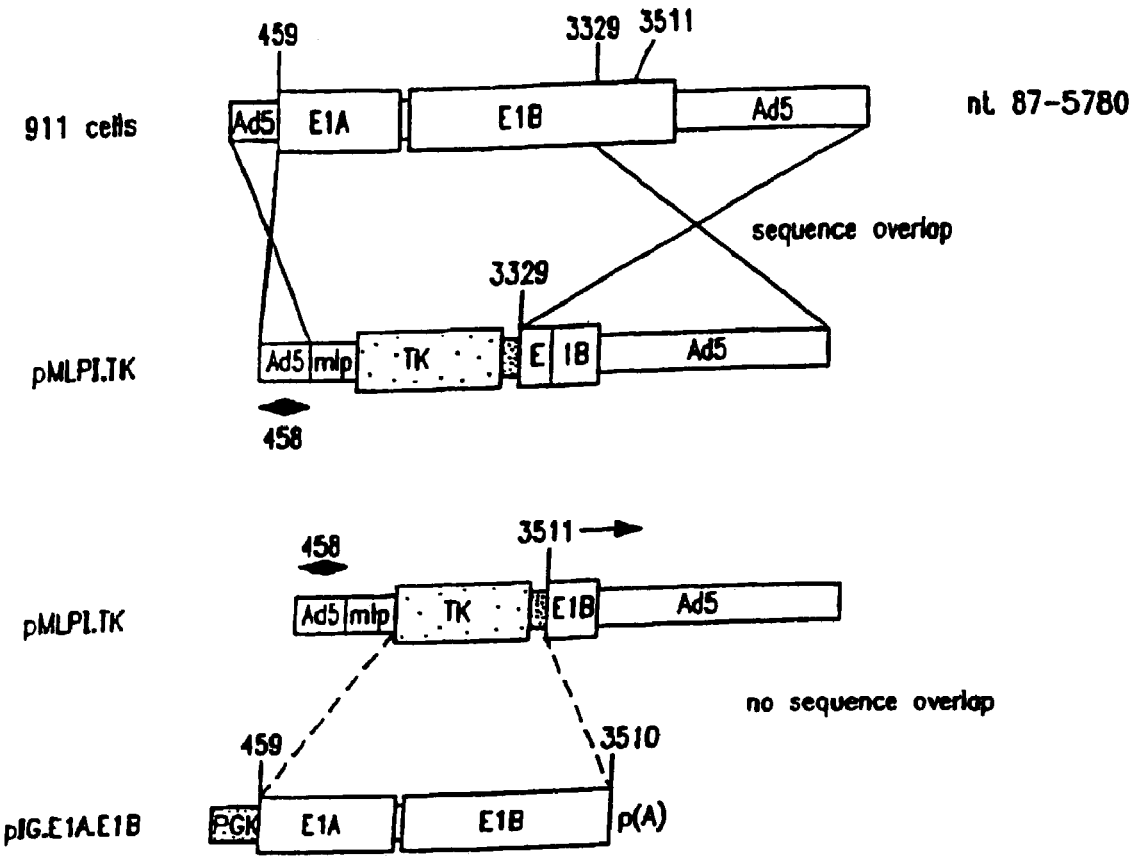
FIGS. 11A–B show that new adenovirus packaging constructs do not have sequence overlap with new adenovirus vectors. Regions of sequence overlap between the packaging construct, pAd5XhoIC expressed in 911 cells and adenovirus vector, pMLP.TK, that can result in homologous recombination and the formation of replication competent adenovirus are shown (Panel A). In contrast, there are no regions of sequence overlap between the new packaging construct, pIG.E1A.E1B, expressed in PER.C6 cells, and the new adenovirus vector, pMLPI.TK, (Panel A) or between the new packaging construct, pIG.E1A.NEO and the new adenovirus vector pMLPI.TK (Panel B) that can result in homologous recombination and the formation of replication competent adenovirus.

The combination of the new packaging construct pIG.E1A.E1B and the recombinant adenovirus pMLPI.TK, which do not have any sequence overlap, are presented in FIG. 11. In this figure, also the original situation is presented, where the sequence overlap is indicated. The absence of overlapping sequences between pIG.E1A.E1B and pMLPI.TK (FIG. 11a) excludes the possibility of homologous recombination between the packaging construct and the recombinant virus, and is therefore a significant improvement for production of recombinant adenovirus as compared to the original situation.

Figure 11B:
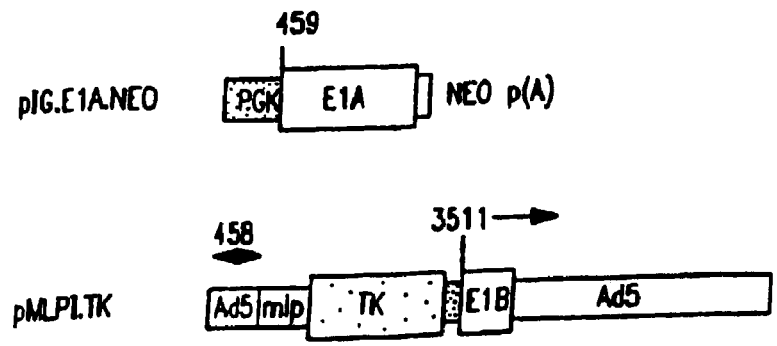

In FIG. 11b the situation is depicted for pIG.E1A.NEO and IG.Ad.MLPI.TK. pIG.E1A.NEO when transfected into established cells, is. expected to be sufficient to support propagation of E1-deleted recombinant adenovirus. This combination does not have any sequence overlap, preventing generation of RCA by homologous recombination. In addition, this convenient packaging system allows the propagation of recombinant adenoviruses that are deleted just for E1A sequences and not for E1B sequences.

Recombinant adenoviruses expressing E1B in the absence of E1A are attractive, as the E1B protein, in particular E1B 19 kD, is able to prevent infected human cells from lysis by Tumor Necrosis Factor (TNF) (Gooding et al, (1991) *J. Virol.* 65:3083–3094).

Generation of Recombinant Adenovirus Derived From pMLPI.TK

Figure 12:
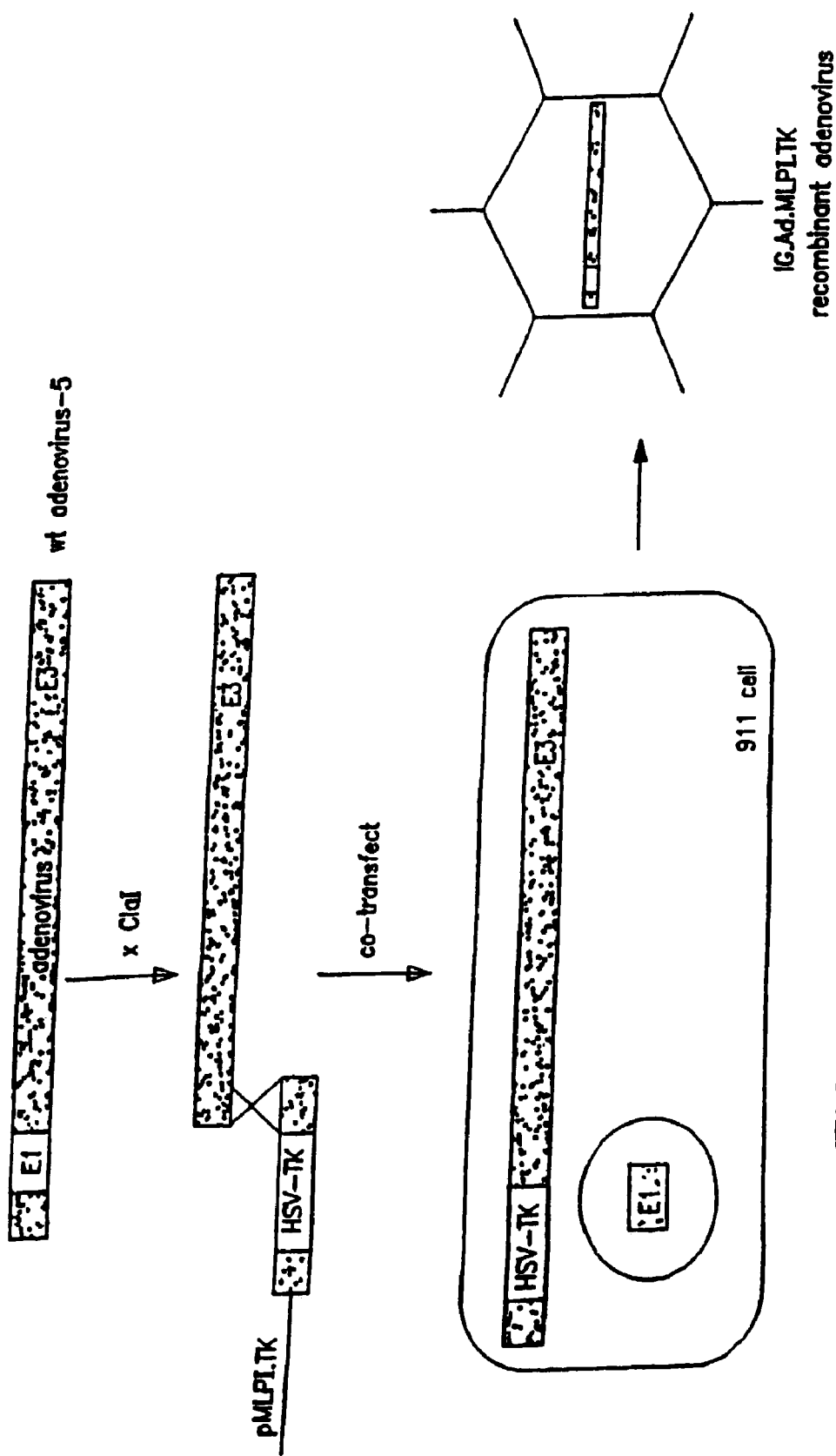
FIG. 12 illustrates the generation of recombinant adenovirus, IG.Ad.MLPI.TK. Recombinant adenovirus, IG.Ad.MLPI.TK, was generated by co-transfection of 293 cells, with SalI linearized pMLPI.TK and the right arm of Cla I digested, wild-type Ad5 DNA. Homologous recombination between linearized pMLPI.TK and wild-type Ad5 DNA produces IG.Ad.MLPI.TK DNA, which contains an E1 deletion of nucleotides 459–3510. 293 cells transcomplement the deleted Ad5 genome, thereby, permitting replication of the IG.Ad.MLPI.TK DNA and its packaging into virus particles.

Recombinant adenovirus was generated by co-transfection of 293 cells with SalI linearized pMLPI.TK DNA and ClaI linearized Ad5 wt DNA. The procedure is schematically represented in FIG. 12.

TABLE II

Production of recombinant adenoviral vector or different packages, cell lines.

| Cell | Passage No. | Yields × $10^{-8}$ pfu/T175 flask.[1] | | | | Producer Mean |
|---|---|---|---|---|---|---|
| | | IG.Ad.CMV.lacZ | IG.Ad.CMV.TK | IG.Ad.MLPI.TK | d1313 | |
| 293 | | 6.0 | 5.8 | 24 | 34 | 17.5 |
| 911 | | 8 | 14 | 34 | 180 | 59.5 |
| PER.C3 | 17 | 8 | 11 | 44 | 40 | 25.8 |

TABLE II-continued

Production of recombinant adenoviral vector or different packages, cell lines.

| Cell | Passage No. | Yields × 10⁻⁸ pfu/T175 flask.[1] | | | Producer | |
| --- | --- | --- | --- | --- | --- | --- |
| | | IG.Ad.CMV.lacZ | IG.Ad.CMV.TK | IG.Ad.MLPI.TK | d1313 | Mean |
| PER.C5 | 15 | 6 | 17 | 36 | 200 | 64.7 |
| PER.C6 | 36 | 10 | 22 | 58 | 320 | 102 |

The yields are the mean of two different experiments. IG.Ad.CMV.lacZ and IG.Ad.CMV.TK are described in patent application EP 95 20 2213. The construction of IG.Ad.MLPI.TK is described in this patent application. Yields of virus per T80 flask were determined by plaque assay on 911 cells, as described in Fallaux et al (1996) Hum. Gene Ther. 7: 215–222). #1493).

Example 2

Plasmid-based System for Rapid RCA-free Generation of Recombinant Adenoviral Vectors A. Construction of Adenovirus Clones pBr/Ad.Bam-rITR (ECACC Deposit P97082122)

In order to facilitate blunt end cloning of the ITR sequences, wild-type human adenovirus type 5 (Ad5) DNA was treated with Klenow enzyme in the presence of excess dNTPs. After inactivation of the Klenow enzyme and purification by phenol/chloroform extraction followed by ethanol precipitation, the DNA was digested with BamHI. This DNA preparation was used without further purification in a ligation reaction with pBr322 derived vector DNA prepared as follows: pBr322 DNA was digested with EcoRV and BamHI, dephosphorylated by treatment with TSAP enzyme (Life Technologies) and purified on LMP agarose gel (SeaPlaque GTG). After transformation into competent E. coli DH5α (Life Techn.) and analysis of ampicillin resistant colonies, one clone was selected that showed a digestion pattern as expected for an insert extending from the BamHI site in Ad5 to the right ITR. Sequence analysis of the cloning border at the right ITR revealed that the most 3' G residue of the ITR was missing, the remainder of the ITR was found to be correct. Said missing G residue is complemented by the other ITR during replication.

pBr/Ad.Sal-rITR (ECACC Deposit P97082119)

pBr/Ad.Bam-rITR was digested with BamHI and SalI. The vector fragment including the adenovirus insert was isolated in LMP agarose (SeaPlaque GTG) and ligated to a 4.8 kb SalI-BamHI fragment obtained from wt Ad5 DNA and purified with the Geneclean II kit (Bio 101, to Inc.). One clone was chosen and the integrity of the Ad5 sequences was determined by restriction enzyme analysis. Clone pBr/Ad.Sal-rITR contains adeno type 5 sequences from the SalI site at bp 16746 up to and including the rITR (missing the most 3' G residue).

pBr/Ad.Cla-Bam (ECACC Deposit P97082117)

wt Adeno type 5 DNA was digested with ClaI and BamHI, and the 20.6 kb fragment was isolated from gel by electro-elution. pBr322 was digested with the same enzymes and purified from agarose gel by Geneclean. Both fragments were ligated and transformed into competent DH5α. The resulting clone pBr/Ad.Cla-Bam was analyzed by restriction enzyme digestion and shown to contain an insert with adenovirus sequences from bp 919 to 21,566.

uBr/Ad.AflII-Bam (ECACC Deposit P97082114)

Clone pBr/Ad.Cla-Bam was linearized with EcoRI (in pBr322) and partially digested with AflII. After heat inactivation of AflII for 20 minutes at 65° C., the fragment ends were filled in with Klenow enzyme. The DNA was then ligated to a blunt double stranded oligo linker containing a PacI site (5'-AATTGTC<u>TTAATTAA</u>CCGCTTAA-3') (SEQ ID NO:1). This linker was made by annealing the following two oligonucleotides: 5'-AATTGTCTTAATTAACCGC-3' (SEQ ID NO:2) and 5'-AATTGCGGTTAATTAAGAC-3' (SEQ ID NO:3), followed by blunting with Klenow enzyme. After precipitation of the ligated DNA to change buffer, the ligations were digested with an excess PacI enzyme to remove concatameres of the oligo. The 22,016 bp partial fragment containing Ad5 sequences from bp 3,534 up to 21,566 and the vector sequences, were isolated in LMP agarose (SeaPlaque GTG), religated and transformed into competent DH5α. One clone that was found to contain the PacI site and that had retained the large adeno fragment was selected and sequenced at the 5' end to verify correct insertion of the PacI linker in the (lost) AflII site.

pBr/Ad.Bam-rITRpac#2 (ECACC Deposit P97082120) and pBr/Ad.Bam-rITR#8 (ECACC Deposit P97082121)

To allow insertion of a PacI site near the ITR of Ad5 in clone pBr/Ad.Bam-rITR about 190 nucleotides were removed between the ClaI site in the pBr322 backbone and the start of the ITR sequences. This was done as follows: pBr/Ad.Bam-rITR was digested with ClaI and treated with nuclease Bal31 for varying lengths of time (2', 5', 10' and 15'). The extent of nucleotide removal was followed by separate reactions on pBr322 DNA (also digested at the ClaI site), using identical buffers and conditions. Bal31 enzyme was inactivated by incubation at 75° C. for 10 minutes, the DNA was precipitated and resuspended in a smaller volume TE buffer. To ensure blunt ends, DNAs were further treated with T4 DNA polymerase in the presence of excess dNTPs. After digestion of the (control) pBr322 DNA with SalI, satisfactory degradation (~150 bp) was observed in the samples treated for 10 minutes or 15 minutes. The 10 minutes or 15 minutes treated pBr/Ad.Bam-rITR samples were then ligated to the above described blunted PacI linkers (see pBr/Ad.AflII-Bam). Ligations were purified by precipitation, digested with excess PacI and separated from the linkers on an LMP agarose gel. After relegation, DNAs were transformed into competent DH5α and colonies analyzed. Ten clones were selected that showed a deletion of approximately the desired length, and these were further, analyzed by T-track sequencing. (T7 sequencing kit, Pharmacia Biotech). Two clones were found with the Pace linker inserted just downstream of the rITR. After digestion with PacI, clone #2 has 28 bp and clone #8 has 27 bp attached to the ITR.

pWE/Ad.AflII-rITR (ECACC Deposit P97082116)

Cosmid vector pWE15(Clontech) was used to clone larger Ad5 inserts. First, a linker containing a unique PacI site was inserted in the EcoRI sites of pWE15 creating pWE.pac. To this end, the double stranded PacI oligo as described for pBr/Ad.AflII-BamHI was used but now with its EcoRI protruding ends. The following fragments were then isolated by electro-elution from agarose gel: pWE.pac digested with PacI, pBr/AflII-Bam digested with Pact and BamHI and pBr/Ad.Bam-rITR#2 digested with BamHI and PacI. These fragments were ligated together and packaged using λ phage packaging extracts (Stratagene) according to the manufacturer's protocol. After infection into host bacteria, colonies were grown on plates and analyzed for presence of the complete insert. pWE/Ad.AflII-rITR contains all adenovirus type 5 sequences from bp 3534 (AflII site) up to and including the right ITR (missing the most 3' G residue).

pBr/Ad.lITR-Sal(9.4) (ECACC Deposit P97082115)

Adeno 5 wt DNA was treated with Klenow enzyme in the presence of excess dNTPs and subsequently digested with SalI. Two of the resulting fragments, designated left ITR-Sal(9.4) and Sal(16.7)-right ITR, respectively, were isolated in LMP agarose (Seaplaque GTG). pBr322 DNA was digested with EcoRV and SalI and treated with phosphatase (Life Technologies). The vector fragment was isolated using the Geneclean method (BIO 101, Inc.) and ligated to the Ad5 SalI fragments. Only the ligation with the 9.4 kb fragment gave colonies with an insert. After analysis and sequencing of the cloning border a clone was chosen that contained the full ITR sequence and extended to the SalI site at bp 9,462.

pBr/Ad.lITR-Sal(16.7) (ECACC Deposit P97082118)

pBr/Ad.lITR-Sal(9.4) is digested with SalI and then dephosphorylated (TSAP, Life Technologies). To extend this clone up to the third SalI site in Ad5, pBr/Ad.Cla-Bam was linearized with. BamHI and partially digested with SalI. A 7.3 kb SalI fragment containing adenovirus sequences from 9462–16746 was isolated in LMP agarose gel and ligated to the SalI-digested pBr/Ad.lITR-Sal(9.4) vector fragment.

pWE/Ad.AflII-EcoRI pWE.pac was digested with ClaI and the 5' protruding ends were filled in using Klenow enzyme. The DNA was then digested with PacI and isolated from agarose gel. pWE/AflII-rITR was digested with EcoRI and after treatment with Klenow enzyme digested with PacI. The large 24 kb fragment containing the adenoviral sequences was isolated from agarose gel and ligated to the ClaI-digested and blunted pWE.pac vector using the Ligation Express™ kit from Clontech. After transformation of Ultracompetent XL10-Gold cells from Stratagene, clones were identified that contained the expected insert. pWE/AflII-EcoRI contains Ad5 sequences from bp 3534–27336.

B. Construction of New Adapter Plasmids

The absence of sequence overlap between the recombinant adenovirus and E1 sequences in the packaging cell line is essential for safe, RCA-free generation and propagation of new recombinant viruses. The adapter plasmid pMLPI.TK (FIG. 10) is an example of an adapter plasmid designed for use according to the invention in combination with the improved packaging cell lines of the invention. This plasmid was used as the starting material to make a new vector in which nucleic acid molecules comprising specific promoter and gene sequences can be easily exchanged.

First, a PCR fragment was generated from pZipΔMo+ PyF101(N⁻) template DNA (described in PCT/NL96/00195) with the following primers: LTR-1: 5'-CTG TAC GTA CCA GTG CAC TGG CCT AGG CAT GGA AAA ATA CAT AAC TG-3' (SEQ ID NO:4) and LTR-2: 5'-GCG GAT CCT TCG AAC CAT GGT AAG CTT GGT ACC GCT AGC GTT AAC CGG GCG ACT CAG TCA ATC G-3' (SEQ ID NO:5). Pwo DNA polymerase (Boehringer Mannheim) was used according to the manufacturer's protocol with the following temperature cycles: once 5 minutes at 95° C.; 3 minutes at 55° C.; and 1 minute at 72° C., and 30 cycles of 1 minute at 95° C., 1 minute at 60° C., 1 minute at 72° C,. followed by once 10 minutes at 72° C. The PCR product was then digested with BamHI and ligated into a pMLP10 (Levrero et al, (1991) Gene 101:195–202) vector digested with PvuII and BamHI, thereby generating vector pLTR10. This vector contains adenoviral sequences from bp 1 up to bp 454 followed by a promoter which includes part of the Mo-MuLV LTR in which the wildtype enhancer sequences are replaced by the enhancer from a mutant polyoma virus (PyF101). The promoter fragment was designated L420.

Next, the coding region of the murine HSA gene was inserted. pLTR10 was digested with BstBI followed by Klenow treatment and digestion with NcoI. The HSA gene was obtained by PCR amplification on pUC18-HSA (Kay et al, (1990) J. Immunol. 145:1952–1959) using the following primers: HSA1, 5'-GCG CCA CCA TGG GCA GAG CGA TGG TGG C-3' (SEQ ID NO:6) and HSA2, 5'-GTT AGA TCT AAG CTT GTC GAC ATC GAT CTA CTA ACA GTA GAG ATG TAG AA-3' (SEQ ID NO:7). The 269 bp amplified fragment was subcloned in a shuttle vector using the NcoI and BglII sites. Sequencing confirmed incorporation of the correct coding sequence of the HSA gene, but with an extra TAG insertion directly following the TAG stop codon. The coding region of the HSA gene, including the TAG duplication was then excised as a NcoI(sticky)-SalI(blunt) fragment and cloned into the 3.5 kb NcoI(sticky)/BstBI (blunt) fragment from pLTR10, resulting in pLTR-HSA 10.

Finally, pLTR-HSA10 was digested with EcoRI and BamHI after which the fragment containing the left ITR, packaging signal, L420 promoter and HSA gene was inserted into vector pMLPI.TK digested with the same enzymes, thereby replacing the promoter and the gene sequences. This resulted in the new adapter plasmid pAd/L420-HSA (FIG. 19) that contains convenient recognition sites for various restriction enzymes around the promoter and gene sequences. SnaBI and AvrII can be combined with HpaI, NheI, KpnI, HindIII to exchange promoter sequences, while the latter sites can be combined with the ClaI or BamHI sites 3' from the HSA coding region to replace genes in this construct.

Figure 20:
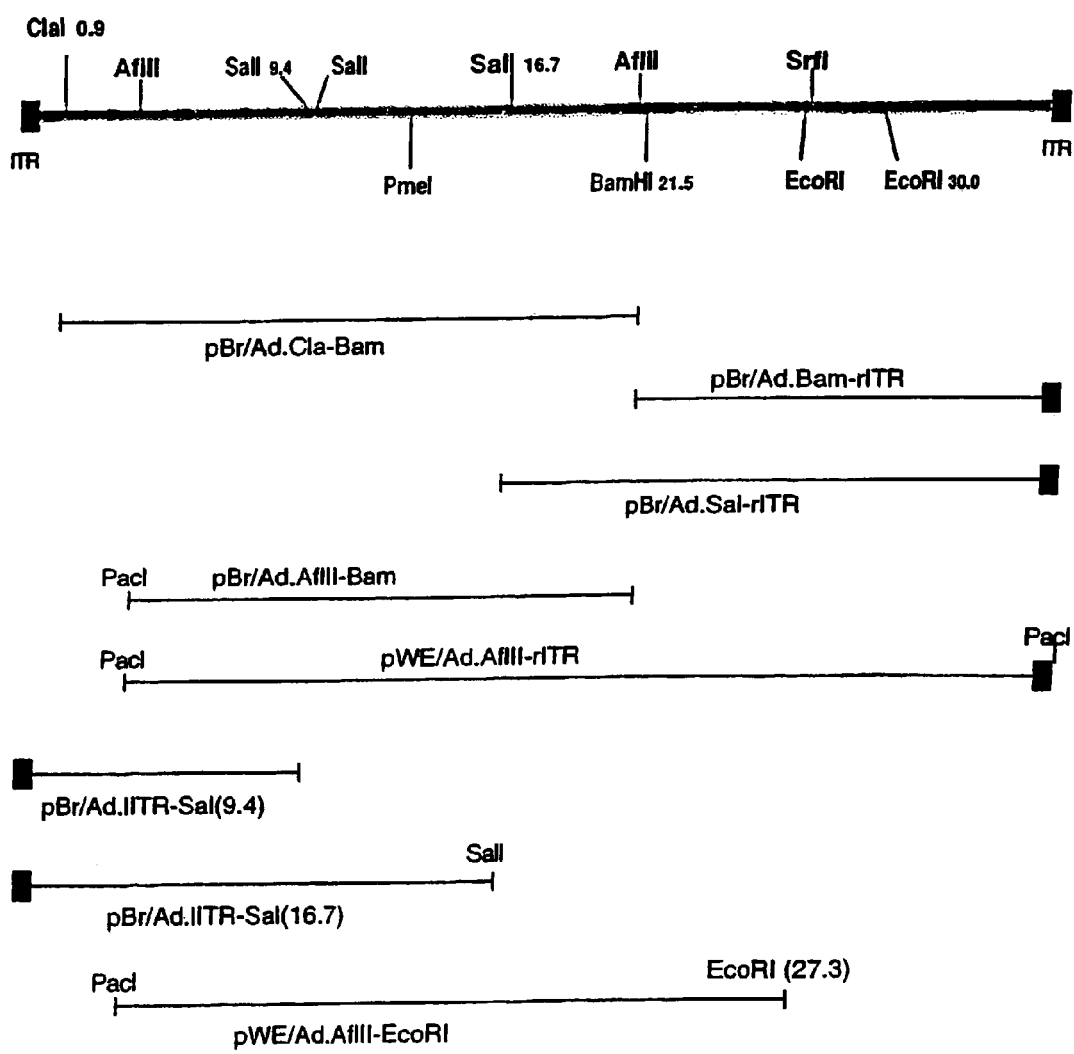
FIG. 20 shows a schematic overview of the adenovirus fragments cloned in pBr322 (plasmid) or pWE15 (cosmid) derived vectors. The top line depicts the complete adenovirus genome flanked by its ITRs (filled rectangles) and with some restriction sites indicated. Numbers following restriction sites indicate approximate digestion sites (in kb) in the Ad5 genome.

Another adapter plasmid that was designed to allow easy exchange of nucleic acid molecules was made by replacing the promoter, gene and poly A sequences in pAd/L420-HSA with the CMV promoter, a multiple cloning site, an intron and a poly-A signal. For this purpose, pAd L420-HSA was digested with AvrII and BglII, followed by treatment with Klenow to obtain blunt ends. The 5.1 kb fragment with pBr322 vector and adenoviral sequences was isolated and ligated to a blunt 1570 bp fragment from pcDNA1/amp (Invitrogen) obtained by digestion with HhaI and AvrII followed by treatment with T4 DNA polymerase. This adapter plasmid was named pCLIP (FIG. 20).

C. Generation of Recombinant Adenoviruses

E1-deleted Recombinant Adenoviruses with wt E3 Sequences

To generate E1 deleted recombinant adenoviruses with the new plasmid-based system, the following constructs were prepared: an adapter construct containing the expression cassette with the gene of interest linearized with a restriction enzyme that cuts at the 3' side of the overlapping adenoviral genome fragment, preferably not containing any pBr322 vector sequences; and a complementing adenoviral genome construct pWE/Ad.AflII-rITR digested with PacI.

Figure 21:
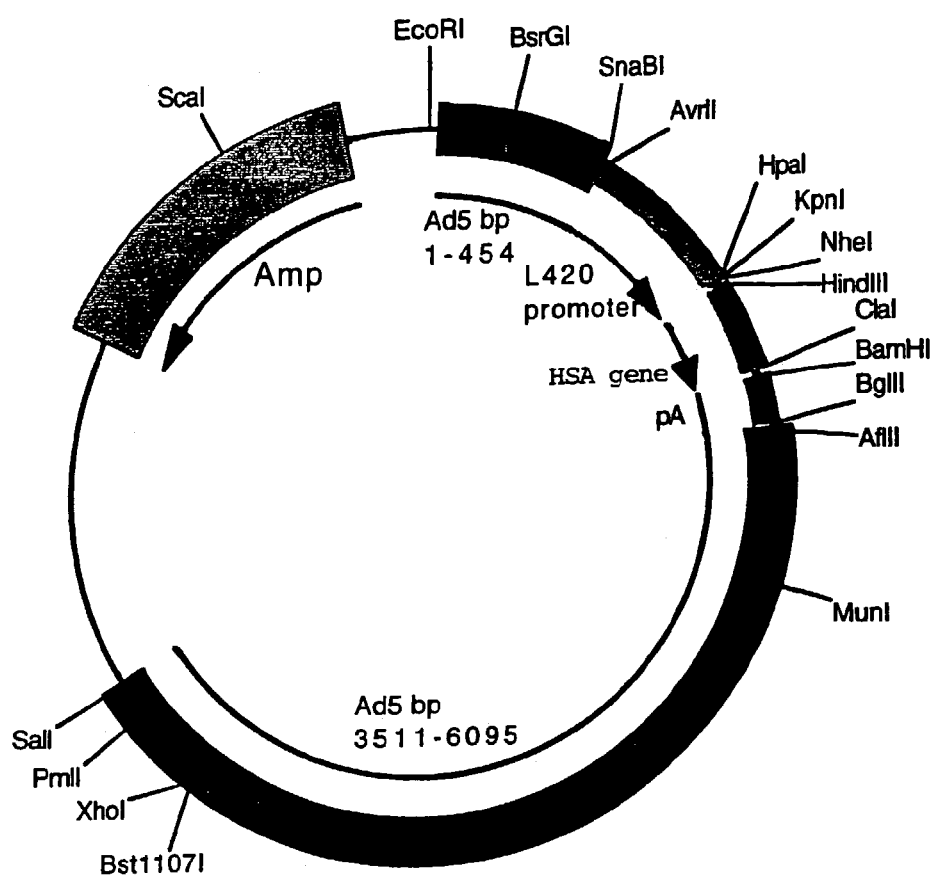
FIG. 21 is a drawing of adapter plasmid pAd/L420-HSA
Figure 22:
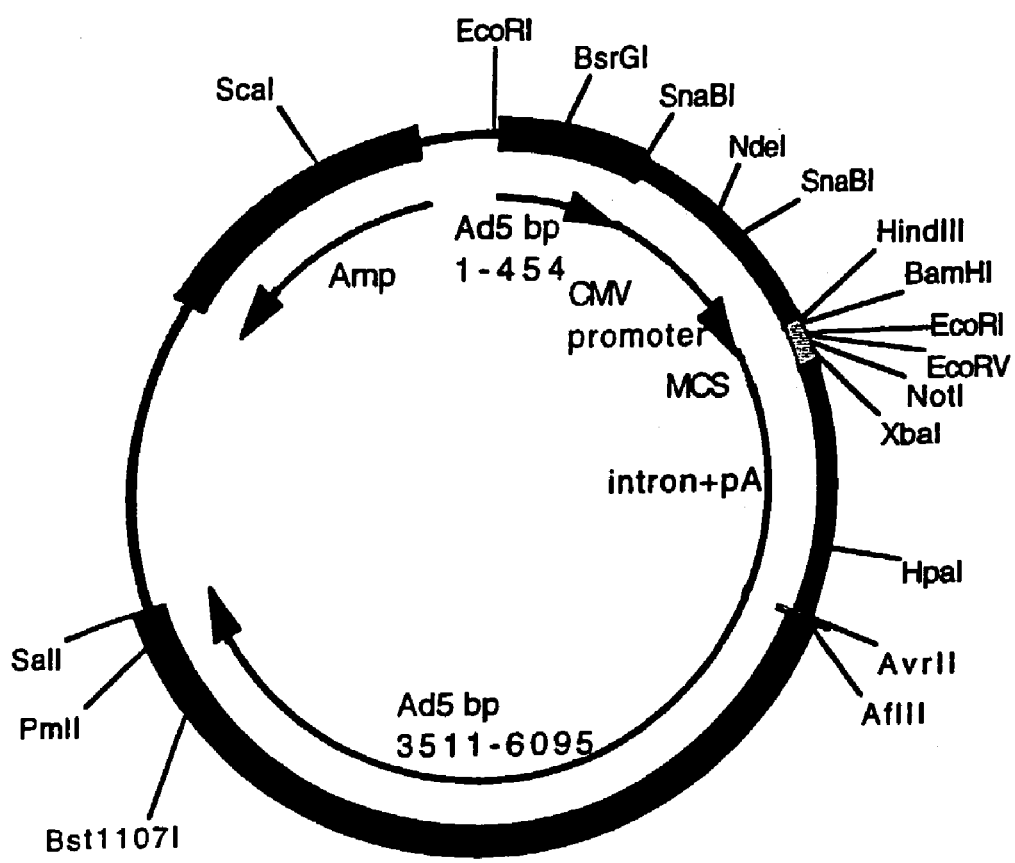
FIG. 22 is a drawing of adapter plasmid pAd/Clip

These two DNA molecules are further purified by phenol/chloroform extraction and EtOH precipitation. Co-transfection of these plasmids into an adenovirus packaging cell line, preferably a cell line according to the invention, generates recombinant replication deficient adenoviruses by a one-step homologous recombination between the adapter and the complementing construct (FIG. 21). Alternatively, instead of pWE/Ad.AflII-rITR other fragments can be used, e.g., pBr/Ad.Cla-Bam digested with EcoRI and BamHI or pBr/Ad.AflIII-BamHI digested with PacI and BamHI can be combined with pBr/Ad.Sal-rITR digested with SalI. In this case, three plasmids are combined and two homologous recombinations are needed to obtain a recombinant adenovirus (FIG. 22). It is to be understood that those skilled in the art may use other combinations of adapter and complementing plasmids without departing from the present invention.

A general protocol as outlined below and meant as a non-limiting example of the present invention has been performed to produce several recombinant adenoviruses using various adapter plasmids and the Ad.AflII-rITR fragment. Adenovirus packaging cells (PER.C6) were seeded in 25 cm$^2$ flasks and the next day when they were at ~80% confluency, were transfected with a mixture of DNA and lipofectamine agent (Life Techn.) as described by the manufacturer. Routinely, 40 µl lipofectamine, 4 µg adapter plasmid and 4 µg of the complementing adenovirus. genome fragment AflII-rITR (or 2 µg of all three plasmids for the double homologous recombination) were used. Under these conditions transient transfection efficiencies of 50% (48 hrs post transfection) were obtained as determined with control transfections using a pAd/CMV-LacZ adapter. Two days later, cells were passaged to 80 cm$^2$ flasks and further cultured. Approximately five (for the single homologous recombination) to eleven days (for the double homologous recombination) later, a cytopathic effect (CPE) was seen, indicating that functional adenovirus has formed. Cells and medium are harvested upon full CPE and recombinant virus is released by freeze-thawing. An extra amplification step in a 80 cm$^2$ flask was routinely performed to increase the yield since at the initial stage the titers was found to be variable despite the occurrence of full CPE. After amplification, viruses were harvested and plaque purified on PER.C6 cells. Individual plaques were tested for viruses with active transgenes.

Four different recombinant adenoviruses, containing the human interleukin-3 gene (see FIG. 1, WO88/04691), the human endothelial nitric oxide gene (Janssens et al,) *J. Biol. Chem.* 267:14519–14522), the TclA transposase gene (Vos et al, (1993) *Genes Dev.* 7:1244–1253), or the bacterial LacZ gene (Kalderon et al, (1984) *Cell* 39:499–509, have been produced using this protocol. In all cases, functional adenovirus was formed and all isolated plaques contained viruses with an active transgene.

E1-deleted Recombinant Adenoviruses with Modifications in the E3 or E4 Regions

Besides replacements in the E1 region it is possible to delete the E3 region or replace part of the E3 region in the adenovirus because E3 functions are not necessary for the replication, packaging and infection of a recombinant virus. This creates the opportunity to use a larger insert or to insert more than one gene without exceeding the maximum packagable size (approximately 105% of wt genome length). This can be done, for example, by deleting part of the E3 region in the pBr/Ad.Bam-rITR clone by digestion with XbaI and religation. This removes Ad5 wt sequences 28592–30470 including all known E3 coding regions. Another example is the precise replacement of the coding region of gp19K in the E3 region with a polylinker allowing insertion of new sequences. This leaves all other coding regions intact, obviates the need for a heterologous promoter, since the transgene is driven by the E3 promoter and pA sequences leaving more space for coding sequences, and results in very high transgene expression, at least as good as in a control E1-replacement vector.

To this end, the 2.7 kb EcoRI fragment from wt Ad5 containing the 5' part of the E3 region was cloned into the EcoRI site of pBluescript (KS) (Stratagene). Next, the HindIII site in the polylinker was removed by digestion with EcoRV and HincII and subsequent religation. The resulting clone pBS.Eco-Eco/ad5ΔHIII was used to delete the gp19K coding region. Primers 1 (5'-GGG TAT TAG GCC AA AGG CGC A-3') (SEQ ID NO:8) and 2 (5'-GAT CCC ATG GAA GCT TGG GTG.GCG-ACC CCA GCG-3') (SEQ ID NO:9) were used to amplify a sequence from pBS.Eco-Eco/ad5ΔHIII corresponding to sequences 28511 to 28734 in wt Ad5 DNA. Primers 3 (5'-GAT CCC ATG GGG ATC CTT TAC TAA GTT ACA AAG CTA-3') (SEQ ID NO:10) and 4 (5'-GTC GCT GTA GTT GGA CTG G-3') (SEQ ID NO:11) were used on the same DNA to amplify Ad5 sequences from 29217 to 29476. The two resulting PCR fragments were ligated together by virtue of the newly introduced NcoI site and subsequently digested with XbaI and MunI. This fragment was then ligated into a pBS.Eco-Eco/ad5ΔHIII vector that had been partially digested with XbaI and MunI, generating pBS.Eco-Eco/ad5ΔHIII.Δgp19K.

To allow insertion of foreign genes into the HindIII and BamHI site, an XbaI deletion was made in pBS.Eco-Eco/ad5ΔHIII.Δgp19K to remove the BamHI sites in the Bluescript polylinker. The resulting plasmid pBS.Eco-Eco/ad5ΔHIIIΔgp19KΔXbaI, contains unique HindIII and BamHI sites corresponding to sequences 28733 (HindIII) and 29218(BamHI) in Ad5.After introduction of a foreign gene into these sites, either the deleted XbaI fragment is re-introduced, or the insert is recloned into pBS.Eco-7Eco/ad5ΔHIII.Δgg19K using HindIII and, for example MunI. Using this procedure, we have generated plasmids expressing HSV-TK (McKnight (1980) *Nucl. Acid. Res.* 8:5949–5964 and Vincent et al (1996) *Hum. Gene Ther.* 7:197–205), hIL-1α (Esandi et al, (1998) *Gene Therapy* 5:xxx-yyy), rat IL-3β (Esandi et al, (1998) *Gene* 11242:xxx-yyy), luciferase (DeWit et al, (1987) *Mol. Cell Biol.* 7:725–737) or LacZ. The unique SrfI and NotI sites in the pBS.Eco-Eco/ad5ΔHIII.Δgp19K plasmid (with or without an inserted gene of interest) are used to transfer the region containing the gene of interest into the corresponding region of pBr/Ad.Bam-rITR, yielding construct pBr/Ad.Bam-rITRΔgp19K (with or without an inserted gene of interest). This construct is used as described supra, to produce recombinant adenoviruses. In the viral context, expression of inserted genes is driven by the adenovirus E3 promoter.

Recombinant viruses that are both E1 and E3 deleted are generated by a double homologous recombination procedure as described above for E1-replacement vectors using a plasmid-based system which includes: an adapter plasmid for E1 replacement according to the invention, with or without insertion of a first gene of interest, the pWE/

Ad.AflII-EcoRI fragment, and the pBr/Ad.Bam-rITRΔgp19K plasmid with or without insertion of a second gene of interest.

In a non-limiting example we describe the generation and functionality of a recombinant adenovirus containing the murine HSA gene in the E1 region and the firefly luciferase gene in the gp19K region. The luciferase gene was excised from pAd/MLP-Luc (described in EP 0707071) as a HindIII-BamHI construct and cloned into the HindIII-BamHI sites of pBS.Eco-Eco/ad5ΔHIIIΔgp19KΔXbaI. Then the MscI-MunI fragment containing the luciferse gene was cloned into the corresponding sites of pBS.Eco-Eco/ad5Δgp19K generating pBS.Eco-Eco/ad5Δgp19K.luc. This restores the Eco-Eco fragment, but now with the luciferase gene in the place of gp19K.

To simplify further manipulation, the internal EcoRI sites in the luciferase insert were mutated without making changes to the amino acid sequence of the luciferase gene. One EcoRI site flanked the HindIII site in the 5' non-coding region of the luciferase insert and the other one was located 588 bp 3' from the starting ATG. A 695 bp PCR product was generated with the following primers: 5'-CGA TAA GCT TAA TTC CTT TGT GTT T-3' (SEQ ID NO:12) and 5'-CTT AGG TAA CCC AGT AGA TCC AGA GGA GTT CAT-3' (SEQ ID NO: 13) and digested with HindIII and BstEII. This fragment was then ligated to HindIII-BstEII digested pBS.Eco-Eco/ad5Δgp19K.luc, replacing the corresponding insert in this vector. The resulting construct is named pBS.Eco-Eco/ad5Δgp19K.luc². The luciferase gene and part of the E3 region were then excised from this clone with SrfI and NotI and introduced in the corresponding sites in pBr/Ad.Bam-rITR generating clone pBr/Ad.Bam-rITRΔgp19K/luc².

The adapter plasmid pAd5/S1800HSA used for the replacement of E1 in the double insert virus contains the murine HSA gene driven by a retrovirus LTR-based promoter. This adapter plasmid was generated from the pAd5/L420-HSA construct described infra by replacement of the promoter sequence. First a PCR product was generated on a retroviral vector based on the MFG-S vector described in WO 95/34669 using the same primers as for the amplification of the L420 promoter fragment (described infra). This PCR amplifies the sequences corresponding to bp 453–877 in the MFG-S vector. The L420-promoter in pAd5/L420-HSA (FIG. 21) was then exchanged for the PCR fragment using the unique AvrII and HindII sites. The resulting construct, pAd5/S430-HSA, was then digested with NheI and ScaI and the 4504 bp fragment containing the HSA gene, pA sequences, Ad5 sequences and vector sequences to the ScaI site in the ampicillin gene was isolated.

The construct pAd5/S430-HSA also was digested with XbaI and ScaI and the 1,252 bp fragment (containing the remainder of the ampicillin gene, the left ITR and packaging signal from adenovirus and the 5' part of the S430 promoter) was isolated. A third fragment of 1,576 bp was isolated from the MFG-S-based retroviral vector following an XbaI digestion and contains MFG-S sequences corresponding to bp 695–2271.

The adapter plasmid pAd5/S1800-HSA was constructed by ligating the three isolated fragments. The double insert virus Ad5/S1800-HSA.E3luc was generated (as described above) by transfection of the following DNA fragments, into PER.C6 cells: pAd5/S1800-HSA digested with EcoRI and SalI (2,μg). At occurrence of CPE, the virus was harvested and amplified by serial passages on PER.C6 cells. The activity of this HSA-luc virus was compared to single insert ΔE1 viruses containing either the S1800-HSA or the CMV-luc transcription units in the E1 region. A549 cells were seeded at $2 \times 10^5$ cells/well and infected 5 hrs later with different amounts of the virus. Two days later transgene expression was measured. Luciferase activity was measured using a luciferase assay system (Promega) and expression of the murine HSA gene was measured with an α-HSA antibody (M1/69, Pharmingen). The results are listed in Table III.

This experiment shows that using the plasmid-based recombination system, double insert viruses can be made and that both inserts are functional. Furthermore, the luciferase activity of the double insert viruses is comparable to the CMV-driven luciferase activity of the control virus. Therefore, we conclude that the E3 promoter is highly active in A549 cells, even in the absence of E1A proteins.

In addition to manipulations in the E3 region, changes of (parts of) the E4 region, can be accomplished easily in pBr/Ad.Bam-rITR. Generation and propagation of such a virus, however, in some cases demands complementation in trans.

Example 3

Demonstration of the Competence of a Synthetic DNA Sequence, that is Capable of Forming a Hairpin Structure, to Serve as a Primer for Reverse Strand Synthesis for the Generation of Double-stranded DNA Molecules in Cells that Contain and Express Adenovirus Genes Name Convention of the Plasmids Used:
p plasmid.
I ITR (Adenovirus Inverted Terminal Repeat)
C Cytomegalovirus (CMV) Enhancer/Promoter Combination
L Firefly Luciferase Coding Sequence
hac, haw Potential hairpin that can be formed after digestion with restriction endonuclease Asp718 in both the correct and in the reverse orientation, respectively (FIG. 15).

FIG. 15 shows the potential hairpin conformation of a single-stranded DNA molecule that contains the HP/asp sequences used in these studies. Restriction with the restriction endonuclease Asp718I of plasmid pICLha containing the annealed oligonucletide pair HP/asp1 and HP/asp2 will yield a linear double stranded DNA fragment. In cells in which the required adenovirus genes are present, replication can initiate at the terminus that contains the ITR sequence. During the chain elongation, one of the strands will be displaced. The terminus of the single-stranded displaced strand molecule can adopt the conformation depicted above. In this conformation, the free 3' terminus can serve as a primer for the cellular and/or adenovirus DNA polymerase, resulting in conversion of the displaced strand in a double-stranded form.

The naming convention is exemplified as follows. pICLhaw is a plasmid that contains the adenovirus ITR followed by the CMV-driven. luciferase gene and the Asp718 hairpin in the reverse (non-functional) orientation. Plasmids pICLhac, pICLhaw, pICLI and pICL were generated using standard techniques. The schematic representation of these plasmids is shown in FIGS. 16–19.

Plasmid pICL is derived from the following plasmids:

(1) nt.1      457   pMLP10 (Levrero et al, (1991) Gene 101: 195–202)
(2) nt.458    1218  pCMVβ (Clontech, EMBL Bank No. U02451)
(3) nt.1219   3016  pMLP.luc (IntroGene, unpublished)

TABLE III-continued (4) nt.3017    5620  pBLCAT5 (Stein et al, (1989) Mol. Cell Biol. 9:4531–4).

TABLE III

Double insert viruses with different transgenes replacing the E1 and E3/gp19K regions express both transgenes in human A549 cells.

| Virus[2] | Amount | % of cells with HSA expression | luciferase activity (light units) |
|---|---|---|---|
| IGAd/CMV-luc | $5 \times 10^7$ i.u. | ND | 25,726,074 |
|  | $2.5 \times 10^7$ i.u. | ND | 7,996,542 |
| IGAd/S1800-HSA | 100 µl ccl | 88% | ND |
|  | 50 µl ccl | 82% | ND |
| IGAd/S1800-HSA.E3luc | $1.2 \times 10^7$ i.u. | 97% | 32,451,300 |
|  | $6 \times 10^7$ i.u. | 97% | 24,716,586 |
|  | $1.2 \times 10^8$ i.u. | 100% | 13,294,321 |

Note:
All virus preps were clarified crude cell lysates (ccl). A clarified cell lysate was made by harvesting cells with medium at full CPE followed by three freeze/thaw cycles. pAd/S1800-HSA was not titrated.

The plasmid has been constructed as follows:

The tet gene of plasmid pMLP10 has been inactivated by deletion of the BamHI-SalI fragment, to generate pBLP10ΔSB. Using primer set PCR/MLP1 and PCR/MLP3 a 210 bp fragment containing the Ad5-ITR, flanked by a synthetic SalI restriction site was amplified using pMLP10 DNA as the template. The PCR product was digested with the enzymes EcoRI and sgrAI to generate a 196 bp fragment. Plasmid pMLP10ΔSB was digested with EcoRI and SgrAI to remove the ITR. This fragment was replaced by the EcoRI-SgrAI-treated PCR fragment to generate pMLP/SAL.

Figure 19:
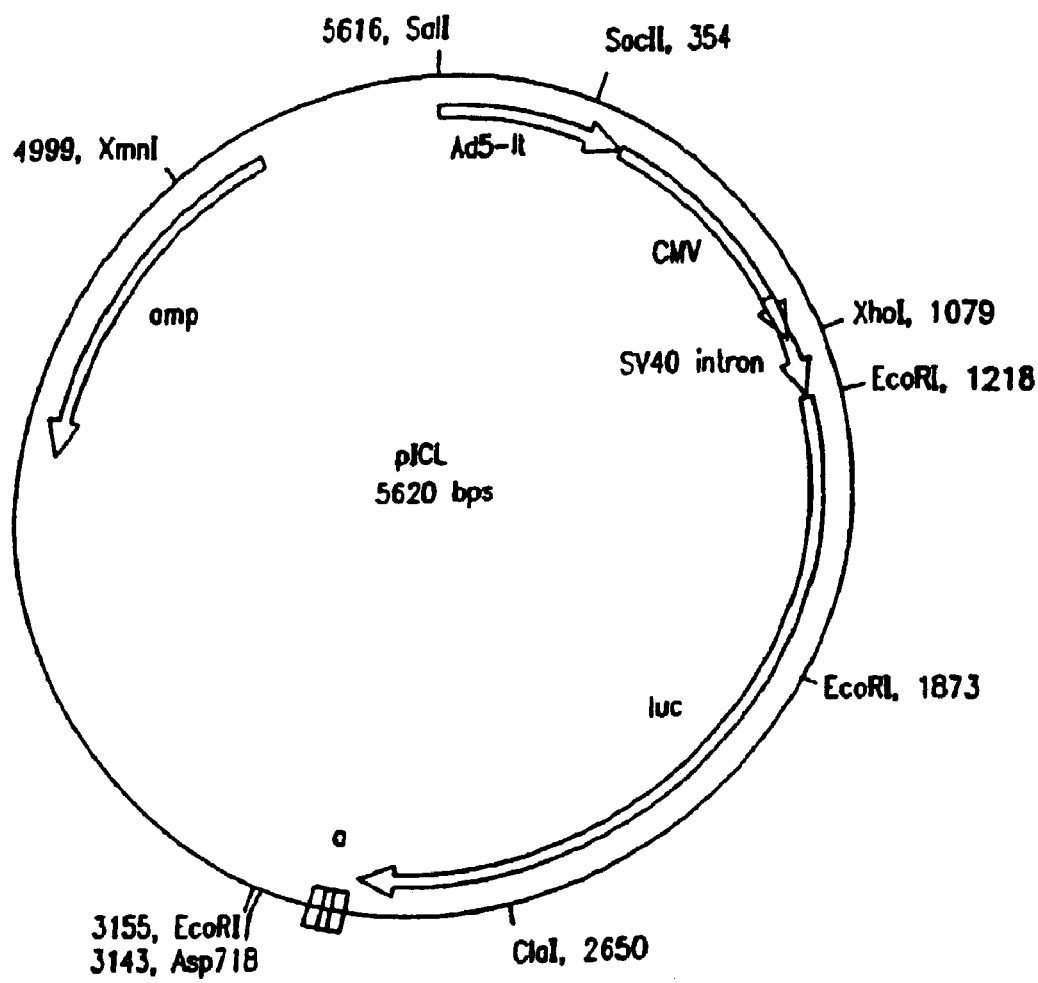
FIG. 19 is a diagram of pICL. pICL is derived from the following: (i) nucleotides 1–457, Ad5 nucleotides 1–457 including the left ITR, (ii) nucleotides 458–969, human CMV enhancer and immediate early promoter, (iii) nucleotides 970–1204, SV40 19S exon and truncated 16/19S intron, (iv) nucleotides 1218–2987, firefly luciferase gene, (v) nucleotides 3018–3131, SV40 tandem polyadenylation signals from the late transcript, (vi) nucleotides 3132–5620, pUC12 sequences including an Asp718 site, and (vii) ampicillin resistance gene in reverse orientation.

Plasmid pCMV-Luc was digested with PvuII to completion and recirculated to remove the SV40-derived polyadenylation signal and Ad5 sequences with exception of the Ad5 left-terminus. In the resulting plasmid, pCMV-lucΔAd, the Ad5 ITR was replaced by the Sal-site-flanked ITR from plasmid pMLP/SAL by exchanging the XmnI-SacII fragments. The resulting plasmid, pCMV-lucΔAd/SAL, the Ad5 left terminus and the CMV-driven luciferase gene were isolated as a SalI-SmaI fragment and inserted in the SalI and HpaI digested plasmid pBLCATS, to form plasmid pICL. Plasmid pICL is represented in FIG. 19; its sequence is presented in FIG. 20.

Plasmid pICL contains the following features:

| nt.1–457 | Ad5 left terminus (Sequence 1–457 of human adenivorus type 5) |
|---|---|
| nt.458–969 | Human cytomegalovirus enhancer and immediate early promoter (Boshart et al, (1985) Cell 41: 521–530) (from plasmid pCMVβ, Clontech, Palo Alto, USA) |
| nt.970–1204 | SV40 19S exon and truncated 16/19S intron (from plasmid pCMVβ) |
| nt.1218–2987 | Firefly luciferase gene (from pMLP.luc) |
| nt.3018–3131 | SV40 tandem poly-adenylation signals from late transcript, derived from plasmid pBLCAT5) |
| nt.3132–5620 | pUC12 backbone (derived from plasmid pBLCAT5) |
| nt.4337–5191 | β-lactamase gene (Amp-resistance gene, reverse orientation) |

Plasmids pICLhac and pICLhaw

Plasmids pICLhac and pICLhaw were derived from plasmid pICL by digestion of pICL with the restriction enzyme Asp718. The linearized plasmid was treated with Calf-Intestine Alkaline Phosphatase to remove the 51 phosphate groups. The partially complementary synthetic single-stranded oligonucleotides Hp/asp1 and Hp/asp2 were annealed and phosphorylated on their 5' ends using T4-polynucleotide kinase.

Figure 16:
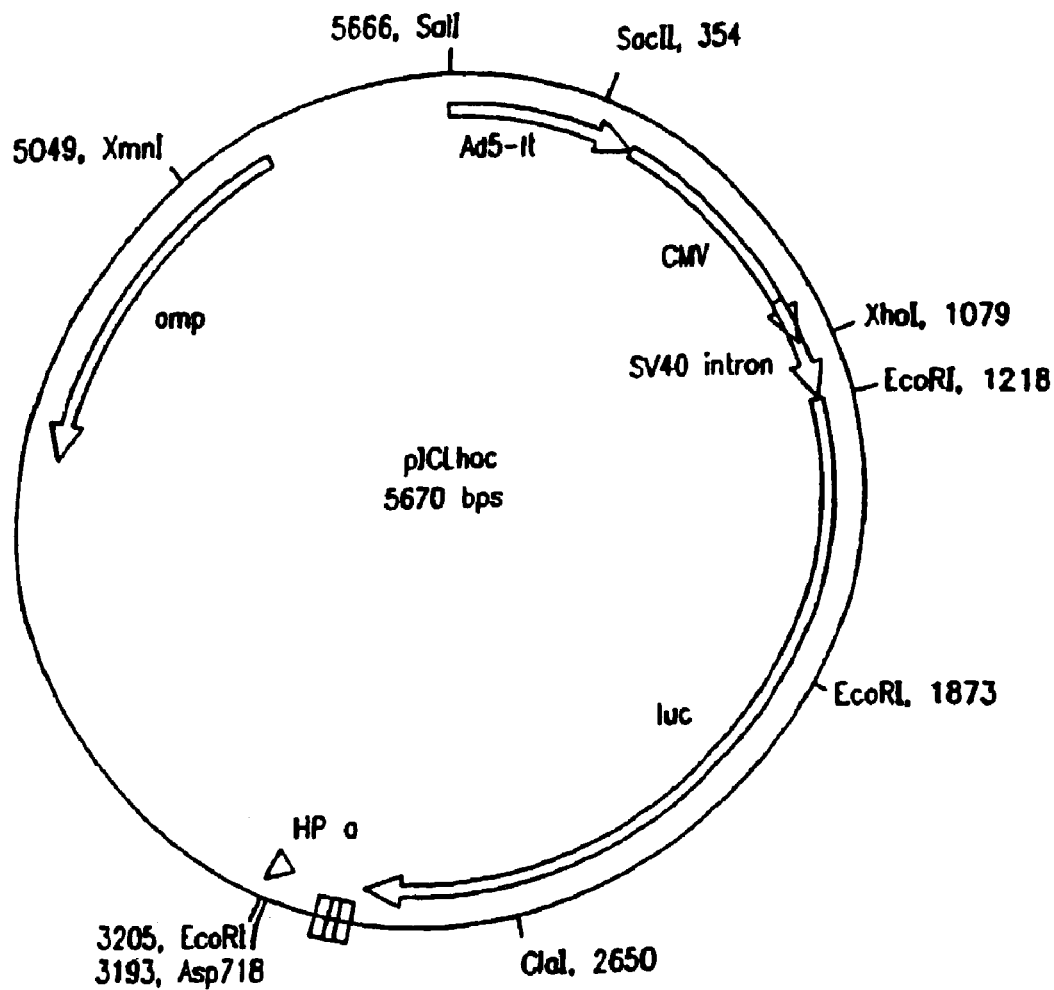
FIG. 16 is a diagram of pICLhac. pICLhac contains all the elements of pICL (FIG. 19) but also contains in the Asp718 site, the HP/asp sequence in an orientation that will produce the hairpin structure shown in FIG. 15, following linearization by Asp718 digestion and transfection into cells expressing adenovirus E2 proteins.
Figure 17:
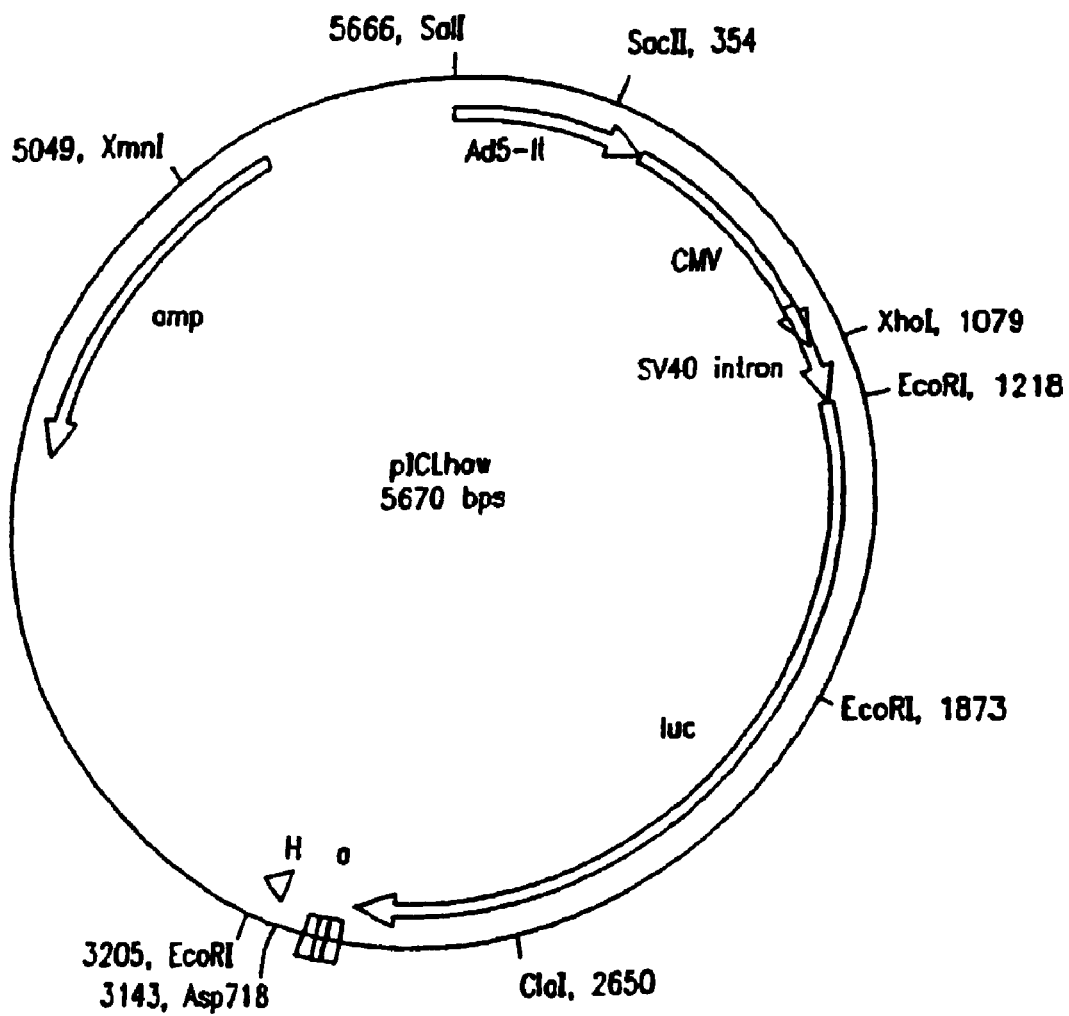
FIG. 17 is a diagram of pICLhaw. pICLhaw is identical to pICLhac (FIG. 16) with the exception that the inserted HP/asp sequence is in the opposite orientation.

The phosphorylated double-stranded oligomers were mixed with the dephosphorylated pICL fragment and ligated. Clones containing a single copy of the synthetic oligonucleotide inserted into the plasmid were isolated and characterized using restriction enzyme digests. Insertion of the oligonucleotide into the Asp718 site will at one junction recreate an Asp718 recognition site, whereas at the other junction the recognition site will be disrupted. The orientation and the integrity of the inserted oligonucleotide was verified in selected clones by sequence analyses. A clone containing the oligonucleotide in the correct orientation (the Asp718 site close to the 3205 EcoRI site) was denoted pICLhac. A clone with the oligonucleotide in the reverse orientation (the Asp718 site close to the SV40 derived poly signal) was designated pICLhaw. Plasmids pICLhac and pICLhaw are represented in FIGS. 16 and 17.

Figure 18:
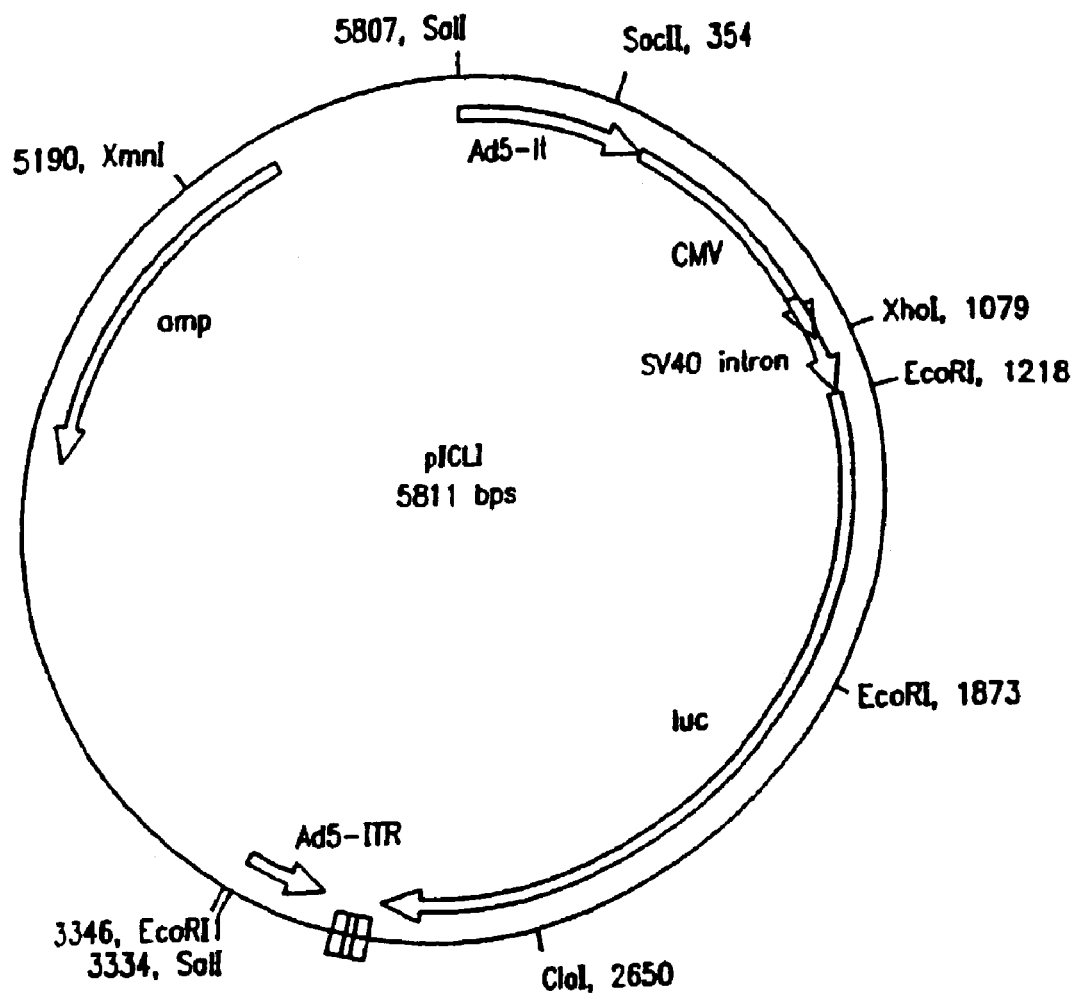
FIG. 18 shows a schematic representation of pICLI. pICLI contains all the elements of pICL (FIG. 19) but also contains in the Asp718 site, an Ad5 ITR.

Plasmid pICLI was created from plasmid pICL by insertion of the SalI-SgrAI fragment from pICL, containing the Ad5-ITR into the Asp718 site of pICL. The 194 bp SalI-SgrAI fragment was isolated from pICL, and the cohesive ends were converted to blunt ends using E. coli DNA polymerase I (Klenow fragment) and dNTP's. The Asp718 cohesive ends were converted to blunt ends by treatment with mungbean nuclease. By ligation clones were generated that contain the ITR in the Asp718 site of plasmid pICL. A clone that contained the ITR fragment in the correct orientation was designated pICLI (FIG. 18).

Generation of adenovirus Ad-CMV-hcTK. Recombinant adenovirus was constructed according to the method described in EP Patent application 95202213. Two components are required to generate a recombinant adenovirus. The first is an adaptor-plasmid containing the left terminus of the adenovirus genome containing the ITR and the packaging signal, an expression cassette with the gene of interest, and a portion of the adenovirus genome which can be used for homologous recombination. In addition, adenovirus DNA is needed for recombination with the aforementioned adaptor plasmid. In the case of Ad-CMV-hcTK, the plasmid PCMV.TK was used as a basis. This plasmid contains nt. 1–455 of the adenovirus type 5 genome, nt.456–1,204 derived from pCMVβ (Clontech, the PstI-StuI fragment that contains the CMV enhancer promoter and, the 16S/19S intron from simian Virus 40), the Herpes Simplex Virus thymidine kinase gene (described in EP patent application 95202213.5), the SV40-derivedpolyadenylation signal (nt.2533–2668 of the SV40 sequence), and followed by the BglII-ScaI fragment of Ad5 (nt. 3328–6092 of the Ad5 sequence). These fragments are present in a pMLP10-derived (Levrero et al, (1991) Gene 101:195–202) backbone. To generate plasmid PAD-CMVhc-TK, plasmid pCMV.TK was digested with ClaI (the unique ClaI-site is located just upstream of the TK open reading frame) and dephosphorylated with Calf-Intestine Alkaline Phosphate. To generate a hairpin-structure, the synthetic oligonucleotides HP/cla2 and HP/cla2 were annealed and phosphorylated on their 5'-OH groups with T4-polynucleotide kinase and ATP. The double-stranded oligonucleotide was ligated with the linearized vector fragment and used to transform E. coli strain, "Sure". Insertion of the oligonucleotide into the ClaI site will disrupt the ClaI recognition sites. The oligonucleotide contains a new ClaI site near one of its termini. In selected clones, the orientation and the integrity of the inserted oligonucleotide was verified by sequence analyses. A clone containing the oligonucleotide in the correct orientation (the, ClaI site at the ITR side) was denoted pAd-CMV-hcTK. This plasmid was co-transfected with ClaI-digested wild-type adenovirus-type5 DNA into 911 cells. A recombinant adenovirus in which the CMV-hcTK expression cassette replaces the E1 sequences was isolated and propagated using standard procedures.

To study whether the hairpin can be used as a primer for reverse strand synthesis on the displaced strand after replication has started at the ITR, the plasmid pICLhac was introduced into 911 cells, i.e. human embryonic retinoblasts transformed with the adenovirus E1 region. The plasmid pICLhaw served as a control it contains the oligonucleotide pair HP/asp 1 and 2 in the reverse orientation but is otherwise completely identical to plasmid pICLhac. Also included in these studies were plasmids pICLI and pICL. In the plasmid pICLI the hairpin is replaced by an adenovirus ITR. Plasmid pICL contains neither a hairpin nor an ITR sequence. These plasmids served as controls to determine the efficiency of replication by virtue of the terminal hairpin structure. To provide the viral products other than the E1 proteins (these are produced by the 911 cells) required for DNA replication the cultures were infected with the virus IG.Ad.MLPI.TK after transfection. Several parameters were being studied to demonstrate proper replication of the transfected DNA molecules. First, DNA extracted from the cell cultures transfected with the aforementioned plasmids and infected with IG.Ad.MLPI.TK virus was analyzed by Southern blotting for the presence of the expected replication intermediates, as well as for the presence of the duplicated genomes. Furthermore, from the transfected and IG.Ad.MLPI.TK infected cell populations, virus was isolated that can transfer a luciferase marker gene into luciferase negative cells and express it.

Plasmid DNA of plasmids pICLhac, pCLhaw, pICLI and pICL were digested with restriction endonuclease SalI and treated with mungbean nuclease to remove the 4 nucleotide single-stranded extension of the resulting DNA fragment. In this manner a natural adenovirus 5'ITR terminus on the DNA fragment was created. Subsequently, both the pICLhac and pICLhaw plasmids were digested with restriction endonuclease Asp718 to generate the terminus capable of forming a hairpin structure. The digested plasmids were introduced into 911 cells, using the standard calcium phosphate co-precipitation technique, four dishes for each plasmid. During the transfection, for each plasmid two of the cultures were infected with the IG.Ad.MLPI.TK virus using 5 infectious IG.Ad.MLPI.TK particles per cell. At twenty-hours post transfection and forty hours post-transfection one Ad.tk-virus-infected and one uninfected culture were used to isolate low molecular-weight DNA using the procedure devised by Hirt (as described in Einerhand et al, (1995) *Gene Therapy* 2:336–343). Aliquots of isolated DNA were used for Southern analysis. After digestion of the samples with restriction endonuclease EcoRI using the luciferase gene as a probe a hybridizing fragment of approx. 2.6 kb were detected in only the samples from the adenovirus-infected cells transfected with plasmid pICLhac. The size of this fragment was consistent with the anticipated duplication of the luciferase marker gene. This supports the conclusion that the inserted hairpin is capable of serving as a primer for reverse strand synthesis. The hybridizing fragment was absent if the IG.Ad.MLPI.TK virus was omitted, or if the hairpin oligonucleotide was inserted in the reverse orientation.

The restriction endoculease DpnI recognizes the tetra-nucleotide sequence 5'-GATC-3', but cleaves only methylated DNA, (that is, only plasmid DNA propagated in, and derived, from *E. coli*, not DNA that has been replicated in mammalian cells). The restriction endonuclease MboI recognizes the same sequences, but cleaves only unmethylated DNA. (namely, DNA propagated in mammalian cells). DNA samples isolated from the transfected cells are incubated with MboI and DpnI and analyzed with Southern blots. These results demonstrate that only in the cells transfected with the pICLhac and the pICLI plasmids large DpnI-resistant fragments were present, that were absent in the MboI treated samples. This data demonstrates that only after transfection of plasmids pICLI and pICLhac, replication and duplication of the fragments occur. This data also demonstrates that in adenovirus-infected cells linear DNA fragments that have on one terminus an adenovirus-derived inverted terminal repeat (ITR) and at the other terminus a nucleotide sequence that can anneal to sequences on the same strand, when present in single-stranded form thereby generate a hairpin structure, and will be converted to structures that have inverted terminal repeat sequences on both ends. The resulting DNA molecules will replicate by the same mechanism as the wild-type adenovirus genomes.

Example 4

Demonstration that the DNA Molecules that Contain a Luciferase Marker Gene, a Single Copy of the ITR, the Encapsidation Signal and a Synthetic DNA Sequence, that is Capable of Forming a Hairpin Structure, are Sufficient to Generate DNA Molecules that can be Encapsidated into Virions To demonstrate that the DNA molecules, generated in Example 3, containing two copies of the CMV-luc marker gene, can be encapsidated into virions, virus was harvested from the remaining two cultures via three cycles of freeze-thaw crushing and was used to infect murine ficroblasts. Forty-eight hours after infection the infected cells are assayed for luciferase activity. To exclude the possibility that the luciferase activity has been induced by transfer of free DNA, rather than via virus particles, virus stocks were treated with DNaseI to remove DNA contaminants. Furthermore, as an additional control, aliquots of the virus stocks were incubated for 60 minutes at 56° C. The heat treatment does not affect the contaminating DNA, but does inactivate the viruses. Significant luciferase activity was only found in the cells after infection with the virus stocks derived from IG.Ad.MLPI.TK-infected cells transfected with the pICLhc and pICLI plasmids. Neither in the non-infected cells, nor in the infected cells transfected with the pICLhw. and pICL was significant luciferase activity demonstrated. Heat inactivation, but not DNaseI treatment, completely eliminated, luciferase expression, demonstrating that adenovirus particles, and not free (contaminating) DNA. fragments were responsible for transfer of the luciferase reporter gene.

These results demonstrate that these small viral genomes can be encapsidated into adenovirus particles and suggest that the ITR and the encapsidation signal are sufficient for encapsidation of linear DNA fragments into adenovirus particles. These adenovirus particles can be used for efficient gene transfer. When introduced into cells that contain and express at least some of the adenovirus genes (namely E1, E2, E4, and L, and VA), recombinant DNA molecules that include at least one ITR, at least part of the encapsidation signal as well as a synthetic DNA sequence, that is capable of forming a hairpin structure, have the intrinsic capacity to autonomously generate recombinant genomes which can be encapsidated into virions. Such genomes and vector system can be used for gene transfer.

Example 5

Demonstration that DNA Molecules which Contain Nucleotides 3510–35953 (Namely 9.7–100 map Units) of the Adenovirus Type 5 Genome (Thus Lack the E1 Protein-coding Regions, the Right-hand ITR and the Encapsidation Sequences) and a Terminal DNA Sequence that is Complementary to a Portion of the Same Strand of the DNA Molecule when Present in Single-stranded Form Other than the ITR, and as a Result is Capable of Forming a Hairpin Structure, can Replicate in 911 Cells In order to develop a replicating DNA molecule that can provide the adenovirus products required to allow the above-mentioned ICLhac vector genome and alike minimal adenovectors to be encapsidated into adenovirus particles by helper cells, the Ad-CMV-hcTK adenoviral vector was developed. Between the CMV enhancer/promoter region and the thymidine kinase gene, the annealed oligonucleotide pair (Table I) HP/cla 1 and 2 was inserted. The vector Ad-CMV-hcTK was propagated and produced in 911 cell using standard procedures. This vector was grown and propagated exclusively as a source of DNA used for transfection. DNA of the adenovirus Ad-CMV-hcTK was isolated from virus particles that had been purified using CsCl density-gradient centrifugation by standard techniques. The virus DNA was digested with restriction endonuclease ClaI. The digested DNA was size-fractionated on an 0.7% agarose gel and the large fragment was isolated and used for further experiments. Cultures of 911 cells were transfected with the large ClaI-fragment of the Ad-CMV-hcTK DNA using standard calcium phosphate co-precipitation techniques. Much like in the previous experiments with plasmid pICLhac, the Ad-CMV-hc replicates starting at the right-hand ITR. Once the 1-strand is displaced, a hairpin can be formed at the left-hand terminus of the fragment. This facilitates DNA polymerase elongation of the chain towards the right-hand side. The process proceeds until the displaced strand is completely converted to its double-stranded form. Finally, the right-hand ITR is recreated, and in this location, normal adenovirus replication-initiation and elongation occur. The polymerase reads through the hairpin, thereby duplicating the molecule. The input DNA molecule of 33,250 bp, that had on one side an adenovirus ITR sequence, and at the other side a DNA sequence that had the capacity to form a hairpin structure, is duplicated so that both ends contain an ITR sequence. The resulting DNA molecule consists of a palindromic structure of approximately 66,500 bp.

This structure is detected in low-molecular weight DNA extracted from transfected cells using Southern analysis. The palindromic nature of the DNA fragment can be demonstrated by digestion of the low-molecular weight DNA with suitable restriction endonucleases and Southern blotting with the HSV-TK gene as the probe. This molecule can replicate itself in the transfected cells by virtue of the adenovirus gene products that are present in the cells. In part, the adenovirus genes are expressed from templates that are integrated in the genome of the target cells (namely, the E1 gene products), the other genes reside in the replicating DNA fragment itself. This linear DNA fragment cannot be encapsidated into virions. Not only does it lack all the DNA sequences required for encapsidation, but its size also is much too large to be encapsidated Example 6

Demonstration that DNA Molecules which Contain Nucleotides 3503–35953 (viz. 9.7–100 map Units) of the Adenovirus Type 5 Genome (thus lack the E1 Protein-coding Regions, the Right-hand ITR and the Encapsidation Sequences) and a Terminal DNA Sequence that is Complementary to a Portion the Same Strand of the DNA Molecule Other than the ITR, and as a Result is Capable of Forming a Hairpin Structure, can Replicate in 911 Cells and can Provide the Helper Functions Required to Encapsidate the pICLI and pICLhac Derived DNA Fragments The purpose of the next series of experiments is to demonstrate that the DNA molecule described in Example 5 can be used to encapsidate the minimal adenovectors described in Examples 3 and 4.

The large fragment isolated after endonuclease ClaI-digestion of Ad-CMV-hcTK DNA was introduced into 911 cells (as described in Example 5) together with endonuclease SalI mungbean nuclease, endonuclease Asp718-treated plasmid pICLhac, or as a control similarly treated plasmid pICLhaw. After 48 hours, virus was isolated by freeze-thaw crushing of the transfected cell population. The virus preparation was treated with DNaseI to remove contaminating free DNA. The virus was used subsequently to infect Rat2 fibroblasts., Forty-eight hours post infection the cells were assayed for luciferase activity. Only in the cells infected with virus isolated from the cells transfected with the pICLhac plasmid, and not with the pICLhaw plasmid, was significant luciferase activity demonstrated. Heat inactivation of the virus prior, to infection completely abolished the luciferase activity, indicating that the luciferase gene was transferred by a viral particle. Infection of 911 cell with the virus stock did not result in any cytopathological effects, demonstrating that pICLhac was produced without any infectious helper virus being propagated on 911 cells. These results demonstrate that the proposed method can be used to produce stocks of minimal-adenoviral vectors, that are completely devoid of infectious helper viruses that are able, to replicate autonomously on adenovirus-transformed human cells or on non-adenovirus transformed human cells.

Example 7

Construction of Plasmids for the Generation and Production of Minimal Adenoviral Vectors A minimal adenovirus vector contains as operably linked components, the adenovirus-derived cis elements necessary for replication and packaging, with or without foreign nucleic acid molecules to be transferred. Recently, the lower limit for efficient packaging of adenoviral vectors has been determined at 75% of the genome length (Parks and Graham, 1997). To allow flexible incorporation of various lengths of stuffer fragments, a multiple, cloning site (MCS) was introduced into a minimal adenoviral vector. To obtain a minimal adenoviral vector according to the invention, the following constructs were made: pAd/L420-HSA (FIG. 19) was digested with BglII and SalI and the vector-containing fragment was isolated. This fragment contains the left ITR and packaging signal from Ad5 and the murine HSA gene driven by a modified retroviral LTR. The right ITR of adenovirus was amplified by PCR on pBr/Ad.BamHI-rITR template DNA using the following primers: PolyL-ITR: 5'-AAC-TGC-AGA-TCT-ATC-GAT-ACT-AGT-CAA-TTG-CTC-GAG-TCT-AGA-CTA-CGT-CAC-CCG-CCC-CGT-TCC-3' (SEQ ID. NO:14) and ITR-BSN: 5'-CGG-GAT-CCG-TCG- ACG-CGG-CCG-CAT-CAT-CAA-TAA-TAT-ACC-3' (SEQ ID NO:15). The amplified fragment was digested with PstI and BamHI and cloned into pUC 119 digested with the same enzymes. After sequence confirmation of correct amplification of the ITR and the MCS, a BglII-SalI fragment was isolated and cloned into the BglII-SalI-digested pAd/L420-HSA fragment described above. The resulting clone was named pAd/L420-HSA.ITR.

Figure 24:
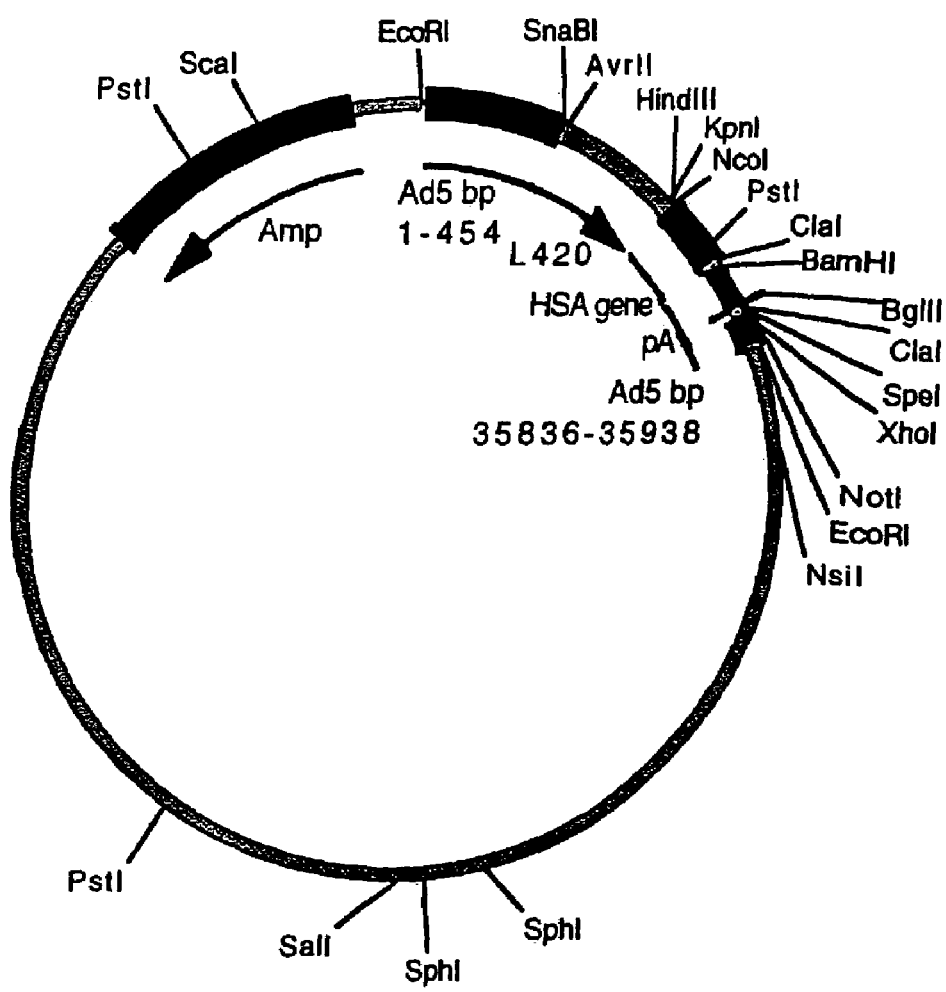
FIG. 24 is a drawing of minimal adenoviral vector pMV/L420H
Figure 25:
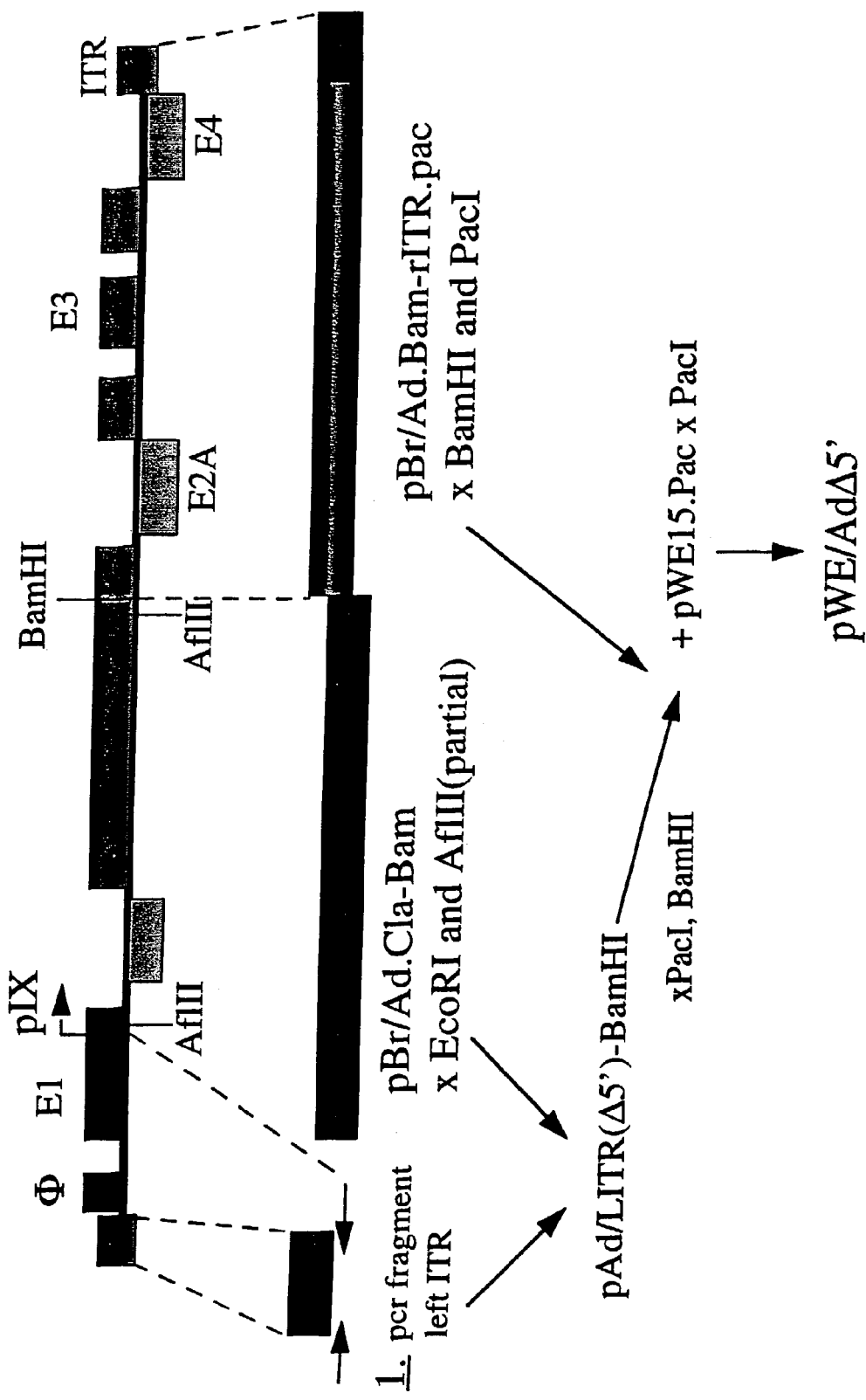
FIG. 25 is a schematic presentation of the cloning steps for the generation of the helper construct pWE/AdΔ5'.

To be able to manipulate constructs of lengths exceeding 30 kb, the minimal adenoviral vector pAd L420-HSA.ITR was subcloned in a cosmid vector background. To this end, the cosmid vector pWE15 was modified to remove restriction sites in the backbone. pWE15 was digested with PstI and fragments of 4 kb and 236 kb were isolated from agarose gel and ligated together. The resulting clone, stripped of the SV40 ori/early promoter and neomycine resistance coding sequence, was named pWE20. Then, pWE20 was digested with ClaI and HindIII and the sticky ends were filled in with Klenow enzyme. A 6,354 bp blunt fragment was ligated to a phosphorylated NsiI linker with the following sequence: 5'-CGATGCATCG-3' (SEQ ID NO:16). The ligated DNA was phenol/chloroform extracted, precipitated with EtOH to change buffers, and digested with excess NsiI Digested DNA was separated from the linkers by electrophoresis, isolated and religated. The resulting clone was named pWE25. Correct insertion of the NsiI linker was confirmed by restriction enzyme digestion and sequencing. To construct the minimal adenoviral vector, pAd/L420-HSA.ITR was digested with ScaI and NotI and the 2 kb fragment containing part of the ampicillin gene and the adeno ITRs was cloned into pWE25 digested with ScaI and NotI. The resulting clone was named pMV/L420H (FIG. 24). This clone allows easy manipulation to exchange the promoter and/or gene, and also allows insertion of DNA fragments of lengths not easily cloned into normal plasmid backbones.

Plasmid pMV/CMV-LacZ was made by exchanging the L420-HSA fragment (SnaBI-BamHI) for a fragment from pcDNA3-nlsLacZ (NruI-BamHI) containing the CMV, promoter and LacZ coding sequences. pcDNA3-nlsLacZ was constructed by insertion of a KpnI-BamHI fragment obtained after PCR amplification of the nlsLacZ coding sequences into pcDNA3 (Invitrogen) digested with KpnI and BamHI. The PCR reaction was performed on a pMLP-.nlsLacZ, template DNA using the primers 1: 5'-GGG-GTG-GCC-AGG-GTA-CCT-CTA-GGC-TTT-TGC-AA-3' (SEQ ID NO: 17) and 2: 5'-GGG-GGG-ATC-CAT-AAA-CAA-GTT-CAG- AAT-CC-3' (SEQ ID NO:18). Correct amplification and cloning were confirmed by assaying 3-galactosidase expression in a transient transfection experiment on 911 cells.

The vector pAd/MLPnlsLacZ was made as follows: pMLP10 (Levrero et al, (1991) *Gene* 101:195–202) was digested with HindIII and BamHI and ligated, in a three-part ligation, to a 3.3 kb AvrII-BamHI fragment from L7RHβgal (Kalderon et al, ) *Cell* 499–509), and a synthetic linker with HindIII and XbaI overhang. The linker was made by annealing two oligonucleotides of sequence 5'-AGC TTG AAT TCC CGG GTA CCT-3' (SEQ ID NO:19) and 5'-CTA GAG GTA CCC GGG 20AAT TCA-3' (SEQ ID NO:20). The resulting clone was named pMLP.nlsLacZ/-Ad. Next, pMLP.nlsLacZ/-Ad was digested with BamHI and NruI and the vector containing fragment was ligated to a 2766 bp BglII-ScaI fragment from pAd5SalB (Bernards et al, (1982) *Virology* 120:422–432). This resulted in the adapter plasmid pMLP.nlsLacZ (described in EP 0 707 071).

Figure 23:
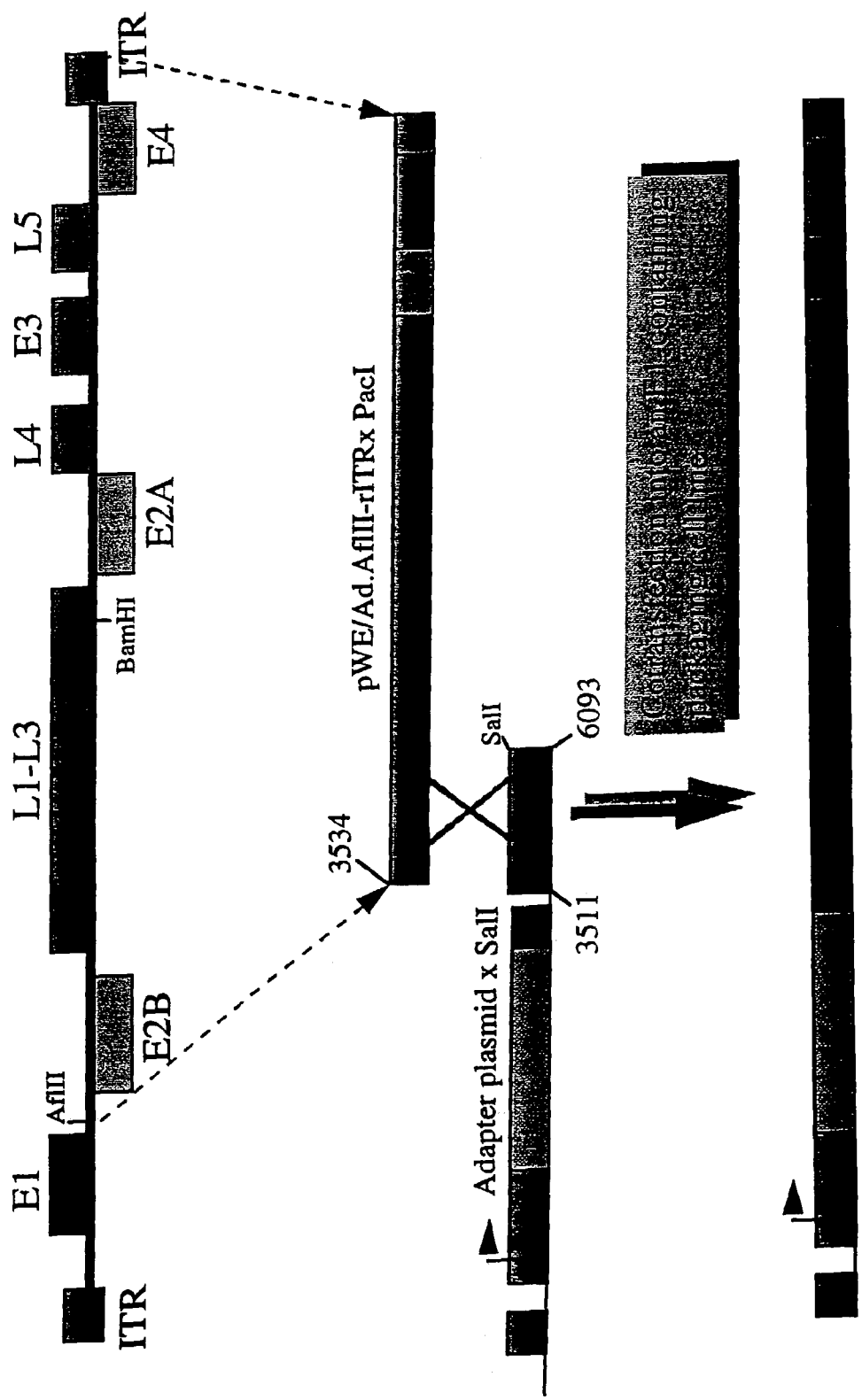
FIG. 23 shows a schematic presentation of the generation of recombinant adenoviruses using a plasmid-based system. In the top the genome organization of Ad5 is given with filled boxes representing the different early and late transcription regions, and flanking ITRs. The middle presents the two DNAs used for a single homologous recombination and, after transfection into packaging cells, leading to the recombinant virus (represented at the bottom).

Propagation of a minimal adenoviral vector can only be achieved by expression of adenovirus gene products. Expression of adenovirus gene products, at levels high enough to sustain production of large quantities of virus, requires replication of the coding nucleic acid molecule. Usually, therefore, replicating helper viruses are used to complement the minimal adenoviral vectors. The present invention, however, provides packaging systems for minimal adenoviral vectors without the use of helper viruses. One of the methods of the invention makes use of a replicating DNA molecule that contains the 5'-ITR and all adenoviral sequences between bp 3,510 and 35,938, i.e., the complete adenoviral genome except for the E1 region and the packaging signal. Construct pWE/Ad.Δ5' (FIG. 23) is an example of a replicating molecule according to the invention that contains two adenoviral ITRs. pWE/Ad.Δ5'. It has been made in a cosmid vector background from three fragments. First, the 5' ITR from Ad5 was amplified using the following primers: ITR-EPH: 5'-CGG-AAT-TCT-TAA-TTA-AGT-TAA-CAT-CAT-CAA-TAA-TA-T-ACC-3' (SEQ ID NO:21) and ITR-pIX: 5'-ACG-GCG-CGC-CTT-AAG-CCA-CGC-CCA-CAC-ATT-TCA-GTA-CGT-ACT-AGT-CTA-CGT-CAC-CCG-CCC-CGT-TCC-3' (SEQ ID NO:22). The resulting PCR fragment was digested with EcoRI and AscI and cloned into vector pNEB 193 (New England Biolabs) which was subsequently digested with the same enzymes. The resulting construct was named pNEB/ITR-pIX. Sequencing confirmed correct amplification of the Ad5 sequences in the left ITR (Ad5 sequences 1 to 103) linked to the pIX promoter (Ad5 sequences 3511 to 3538) except for a singles mismatch with the expected sequence according to GenBank (Accession no.: M73260/M29978), i.e., an extra C-residue was found just upstream of the AflII site. This ITR-pIX fragment was isolated with EcoRI and AflII and ligated to a EcoRI-AflII vector fragment containing Ad5 sequences 3539–21567. The latter fragment was obtained by digestion of pBr/Ad.Cla-Bam (supra) with EcoRI and partially with s AflII. The resulting cone was named pAd/LITR(A5')-BamHI. The final construct pWE/Ad.Δ5' was made by ligating cosmid vector pWE15.Pac (supra) digested with PacI: to pAd/LITR(A5')-BamHI digested with PacI/BamHI and pBr/Ad.Bam-rITR.pac#2 (supra) digested with PacI/BamHI (FIG. 23).

An alternative method to produce packaging systems for minimal adenoviral vectors without the use of helper viruses according to the invention is to use a replicating DNA molecule that contains the complete adenoviral genome, except for the E1 region and the packaging signal, and in which one of the ITRs is replaced by a fragment containing a DNA sequence complementary to a portion of the same strand other than the ITR. Therefore, a hairpin structure is able to form. (FIG. 10). In a non-limiting example, said DNA sequence complementary to a portion of the same strand other than the ITR is derived from the adeno-associated virus (AAV) terminal repeat. Such a replicating DNA molecule is made following the same cloning strategy as described for pWE/Ad.Δ5', but now starting with the AAV terminal repeat linked to part of the adenoviral pIX promoter. To this end, the adenoviral ITR sequences between the HpaI and SpeI sites in construct pNEB/ITR-pIX were exchanged for the AAV ITR by introducing the PvuII/XbaI fragment from psub201 (+) containing the AAV ITR (Samulski et al, (1989) *J. Virol.* 63:3822–3828). This results in construct pWE/AAV.Δ5' that replicates in an E1 complementing cell line.

Another alternative packaging system for minimal adenoviral vectors is described infra, and makes use of the replication system of SV40. A functional helper molecule according to this method contains at least the adenoviral sequences necessary to sustain packaging of a minimal construct, but not the E1 sequences and packaging signal, and preferably also lacking ITRs. This adenovirus-derived entity has to be present on a vector that contains, besides the sequences needed for propagation in bacteria, an origin of replication from SV40 virus. Transfection of such a molecule together with the minimal adenoviral vector, described supra, into a packaging cell line (e.g. PER.C6) expressing, besides the E1 proteins, SV40 derived Large T antigen proteins, resulting in Large T-dependent replication of the adenovirus-derived helper construct. This replication leads to high levels of adenoviral proteins necessary for replication of the minimal adenoviral vector and packaging into virus particles. In this way, there is no sequence overlap that leads to homologous recombination between the minimal adenoviral vector construct and the helper molecule. In addition, there is no sequence overlap that leads to homologous recombination between the helper molecule and minimal adenoviral vector on the one side and the E1 sequence in the packaging cell on the other side.

Replication of a 40 kb adenoviral construct was investigated in cells expressing SV40 Large T proteins. Hereto, $2 \times 10^6$ Cos-1 cells were transfected in a T25 flask with the following constructs complexed with lipofectamine reagent (Life techn.): the 8 kb cosmid vector pWE.pac, the 40.5 kb construct pWE/Ad.AflII-rITR and three clones (#1, #5 and #9) of the 40.6 kb construct pWE/Ad.Δ5' (described infra). Control transfections were carried out with the constructs pWE.pac and pWE/Ad.AflII-rITR digested with PacI enzyme and a CMV-LacZ expression vector without the SV40 ori sequence. Transfection efficiency was 50% as determined by a separate transfection using the CMV-LacZ vector and X-gal staining after 48 hrs. All cells were harvested 48 hrs. following transfection and DNA was extracted according to the Hirt procedure (as described in Einerhand et al, (1995) *Gene Therapy* 2:336–343). Final pellets were resuspended in 50 µl TE+RNase (20 µg/ml) and 10 µl samples were digested with MboI (35 units overnight at 37° C.). Undigested samples (5 µl) and MboI digested samples were run on a 0.8% agarose gel, transferred to a nylon filter (Amersham) and hybridized to radioactive probes according to standard procedures. One probe was derived from an 887 bp DpnI fragment from the cosmid vector pWE.pac and one was derived from a 1,864 bp BsrGI-BamHI fragment from adenoviral sequences. These probes hybridize to a 887 bp band and a 1,416 bp respectively in MboI. digested material. Input DNA from bacterial origin is methylated and therefore not digested with MboI. In this way it is possible to specifically detect DNA that is replicated in eukaryotic cells. FIG. 26A shows a schematic presentation of the construct pWE/Ad.Δ5' and the locations of the SV40 origin of replication, the pWE-derived probe and the adenovirus-derived probe. The lower part presents the autoradiograms of the Southern blots hybridized to the adenovirus probe (B) and the pWE probe (C). (See legends for explanation of sample loading). These experiments show that all lanes that contain material from Cos-1 cells that are transfected with plasmids harbouring an SV40 ori contain MboI sensitive DNA and show a specific band of the expected length. The bands specific for replication in the lanes with Cos-1 cells transfected with PacI digested material (lanes B17/18 and C 15–18) probably result from incomplete PacI digestion. From these experiments, it can be concluded that it is possible to replicate large DNA fragments with the SV40 LargeT/ori system in eukaryotic cells.

Example 8

A functional adenovirus helper molecule lacking ITR sequences was constructed starting with the clone pWE/Ad.D5' described supra. pWE/Ad.D5' was digested with Bstl 107I and the 17.5 kb vector-containing fragment was religated to give pWE/Ad.D5'-Bstl 107I. This clone was then used to amplify the 3' part of the adenovirus genome sequences without the right ITR. A 2,645 bp PCR fragment was generated using the primers Ad3' /Forw: 5'-CGG AAT TCA TCA GGA TAG GGC GGT GG-3' (SEQ ID NO:23) and Ad3'/Rev: 5'-CGG GAT CCT ATC GAT ATT TAA ATG TTT TAG GGC GGA GTA ACT TG-3' (SEQ ID NO:24). The amplified fragment was digested with EcoRI and BamHI and subcloned in pBr322 digested with the same enzymes. After confirmation of correct amplification by sequencing, the 2,558 bp SbfI-ClaI fragment of this clone was recloned in pWE/Ad.D5'-Bstl 1071 digested with the same enzymes. The resulting construct lacks the right ITR and is named pWE/ΔrI-Bstl 1071. Next, in this clone the left ITR was replaced, by a linker with a PacI and AflII overhang made up by annealing the following primers: PA-pIX1 5'-TAA GCC ACT AGT ACG TAC TGA AAT GTG TGG GCG TGG C-3' (SEQ ID NO:25) and PA-pIX 5'-TTA AGC CAC GCC CAC ACA TTT CAG TAC GTA CTA GTG GCT TAA T-3' (SEQ ID NO:26). This removed the left ITR and restored correct sequence of the pIX promoter. The clone is named pWE/ΔITR-Bstl 107I. Correct insertion of the double stranded linker was confirmed by sequencing. The deleted Bstl 107I fragment was then cloned back into pWE/ΔITR-Bstl 107I and the correct orientation was checked by restriction digestion. The resulting clone is named pWE/Ad-H. Following transfection of this DNA molecule into packaging cells that express adenoviral E1 proteins and the SV40 Large T antigen, replication of that molecule takes place resulting in high levels of adenoviral proteins encoded by the adenoviral entity on that molecule.

All publications and patent applications mentioned in this specification are indicative of the level of skill, of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

SEQUENCE LISTING

<160> NUMBER OF SEQ ID NOS: 47

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: oligo
      linker
<220> FEATURE:
<221> NAME/KEY: misc_feature
<222> LOCATION: (1)..(23)
<223> OTHER INFORMATION: /Note="linker with PacI site"

<400> SEQUENCE: 1
aattgtctta attaaccgct taa                                             23

<210> SEQ ID NO 2
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: /Note="linker with Pac site"
<220> FEATURE:
<223> OTHER INFORMATION: Description of Artificial Sequence: oligo
      linker

<400> SEQUENCE: 2
aattgtctta attaaccgc                                                  19

<210> SEQ ID NO 3
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: /Note="linker with Pac site"
<220> FEATURE:
<223> OTHER INFORMATION: Description of Artificial Sequence: oligo
      linker

<400> SEQUENCE: 3
aattgcggtt aattaagac                                                  19

<210> SEQ ID NO 4
<211> LENGTH: 47
<212> TYPE: DNA
<213> ORGANISM: Artificial Sequence
<220> FEATURE:
<221> NAME/KEY: primer_bind
<222> LOCATION: (1)..(47)
<223> OTHER INFORMATION: /Note="primer LTR-1"
<220> FEATURE:
<223> OTHER INFORMATION: Description of Artificial Sequence:primer

<400> SEQUENCE: 4
ctgtacgtac cagtgcactg gcctaggcat ggaaaaatac ataactg                   47

<210> SEQ ID NO 5
<211> LENGTH: 64
<212> TYPE: DNA
<213> ORGANISM: Artificial Sequence
<220> FEATURE:
<221> NAME/KEY: primer_bind
<222> LOCATION: (1)..(64)

<223> OTHER INFORMATION: /Note="primer LTR-2"
<220> FEATURE:
<223> OTHER INFORMATION: Description of Artificial Sequence: primer

<400> SEQUENCE: 5
gcggatcctt cgaaccatgg taagcttggt accgctagcg ttaaccgggc gactcagtca    60
atcg    64

<210> SEQ ID NO 6
<211> LENGTH: 28
<212> TYPE: DNA
<213> ORGANISM: Artificial Sequence
<220> FEATURE:
<221> NAME/KEY: primer_bind
<222> LOCATION: (1)..(28)
<223> OTHER INFORMATION: /Note="primer HSA1"
<220> FEATURE:
<223> OTHER INFORMATION: Description of Artificial Sequence: primer

<400> SEQUENCE: 6
gcgccaccat gggcagagcg atggtggc    28

<210> SEQ ID NO 7
<211> LENGTH: 50
<212> TYPE: DNA
<213> ORGANISM: Artificial Sequence
<220> FEATURE:
<221> NAME/KEY: primer_bind
<222> LOCATION: (1)..(50)
<223> OTHER INFORMATION: /Note="primer HSA2"
<220> FEATURE:
<223> OTHER INFORMATION: Description of Artificial Sequence: primer

<400> SEQUENCE: 7
gttagatcta agcttgtcga catcgatcta ctaacagtag agatgtagaa    50

<210> SEQ ID NO 8
<211> LENGTH: 21
<212> TYPE: DNA
<213> ORGANISM: Artificial Sequence
<220> FEATURE:
<221> NAME/KEY: primer_bind
<222> LOCATION: (1)..(21)
<223> OTHER INFORMATION: /Note="primer1"
<220> FEATURE:
<223> OTHER INFORMATION: Description of Artificial Sequence: primer

<400> SEQUENCE: 8
gggtattagg ccaaaggcgc a    21

<210> SEQ ID NO 9
<211> LENGTH: 33
<212> TYPE: DNA
<213> ORGANISM: Artificial Sequence
<220> FEATURE:
<221> NAME/KEY: primer_bind
<222> LOCATION: (1)..(33)
<223> OTHER INFORMATION: /Note="primer 2"
<220> FEATURE:
<223> OTHER INFORMATION: Description of Artificial Sequence: primer

<400> SEQUENCE: 9
gatcccatgg aagcttgggt ggcgacccca gcg    33

<210> SEQ ID NO 10
<211> LENGTH: 36
<212> TYPE: DNA
<213> ORGANISM: Artificial Sequence

```
<220> FEATURE:
<221> NAME/KEY: primer_bind
<222> LOCATION: (1)..(36)
<223> OTHER INFORMATION: /Note="primer 3"
<220> FEATURE:
<223> OTHER INFORMATION: Description of Artificial Sequence: primer

<400> SEQUENCE: 10
gatcccatgg ggatccttta ctaagttaca aagcta                          36

<210> SEQ ID NO 11
<211> LENGTH: 19
<212> TYPE: DNA
<213> ORGANISM: Artificial Sequence
<220> FEATURE:
<221> NAME/KEY: primer_bind
<222> LOCATION: (1)..(19)
<223> OTHER INFORMATION: /Note="primer 4"
<220> FEATURE:
<223> OTHER INFORMATION: Description of Artificial Sequence: primer

<400> SEQUENCE: 11
gtcgctgtag ttggactgg                                             19

<210> SEQ ID NO 12
<211> LENGTH: 25
<212> TYPE: DNA
<213> ORGANISM: Artificial Sequence
<220> FEATURE:
<221> NAME/KEY: primer_bind
<222> LOCATION: (1)..(25)
<223> OTHER INFORMATION: /Note="primer"
<220> FEATURE:
<223> OTHER INFORMATION: Description of Artificial Sequence: primer

<400> SEQUENCE: 12
cgataagctt aattcctttg tgttt                                      25

<210> SEQ ID NO 13
<211> LENGTH: 33
<212> TYPE: DNA
<213> ORGANISM: Artificial Sequence
<220> FEATURE:
<221> NAME/KEY: primer_bind
<222> LOCATION: (1)..(33)
<223> OTHER INFORMATION: /Note="primer"
<220> FEATURE:
<223> OTHER INFORMATION: Description of Artificial Sequence: primer

<400> SEQUENCE: 13
cttaggtaac ccagtagatc cagaggagtt cat                             33

<210> SEQ ID NO 14
<211> LENGTH: 63
<212> TYPE: DNA
<213> ORGANISM: Artificial Sequence
<220> FEATURE:
<221> NAME/KEY: primer_bind
<222> LOCATION: (1)..(63)
<223> OTHER INFORMATION: /Note="primer polyL-ITR"
<220> FEATURE:
<223> OTHER INFORMATION: Description of Artificial Sequence: primer

<400> SEQUENCE: 14
aactgcagat ctatcgatac tagtcaattg ctcgagtcta gactacgtca cccgcccccgt    60 tcc                                                              63

<210> SEQ ID NO 15
```

```
<211> LENGTH: 39
<212> TYPE: DNA
<213> ORGANISM: Artificial Sequence
<220> FEATURE:
<221> NAME/KEY: primer_bind
<222> LOCATION: (1)..(39)
<223> OTHER INFORMATION: /Note="primer ITR-BSN"
<220> FEATURE:
<223> OTHER INFORMATION: Description of Artificial Sequence: primer

<400> SEQUENCE: 15
cgggatccgt cgacgcggcc gcatcatcaa taatatacc                              39

<210> SEQ ID NO 16
<211> LENGTH: 10
<212> TYPE: DNA
<213> ORGANISM: Artificial Sequence
<220> FEATURE:
<221> NAME/KEY: misc_feature
<222> LOCATION: (1)..(10)
<223> OTHER INFORMATION: /Note="phosphorylated NSI linker"
<220> FEATURE:
<223> OTHER INFORMATION: Description of Artificial Sequence: linker NSI

<400> SEQUENCE: 16
cgatgcatcg                                                              10

<210> SEQ ID NO 17
<211> LENGTH: 32
<212> TYPE: DNA
<213> ORGANISM: Artificial Sequence
<220> FEATURE:
<221> NAME/KEY: primer_bind
<222> LOCATION: (1)..(32)
<223> OTHER INFORMATION: /Note="primer 1"
<220> FEATURE:
<223> OTHER INFORMATION: Description of Artificial Sequence: primer

<400> SEQUENCE: 17
ggggtggcca gggtacctct aggcttttgc aa                                     32

<210> SEQ ID NO 18
<211> LENGTH: 29
<212> TYPE: DNA
<213> ORGANISM: Artificial Sequence
<220> FEATURE:
<221> NAME/KEY: primer_bind
<222> LOCATION: (1)..(29)
<223> OTHER INFORMATION: /Note="primer 2"
<220> FEATURE:
<223> OTHER INFORMATION: Description of Artificial Sequence: primer

<400> SEQUENCE: 18 gggggggatcc ataaacaagt tcagaatcc                                        29

<210> SEQ ID NO 19
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: /Note="linker"
<220> FEATURE:
<223> OTHER INFORMATION: Description of Artificial Sequence: linker

<400> SEQUENCE: 19
agcttgaatt cccgggtacc t                                                 21
```

```
<210> SEQ ID NO 20
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: /Note="linker"
<220> FEATURE:
<223> OTHER INFORMATION: Description of Artificial Sequence: linker

<400> SEQUENCE: 20
ctagaggtac ccgggaattc a                                              21

<210> SEQ ID NO 21
<211> LENGTH: 39
<212> TYPE: DNA
<213> ORGANISM: Artificial Sequence
<220> FEATURE:
<221> NAME/KEY: primer_bind
<222> LOCATION: (1)..(39)
<223> OTHER INFORMATION: /Note="primer ITR-EPH"
<220> FEATURE:
<223> OTHER INFORMATION: Description of Artificial Sequence: primer

<400> SEQUENCE: 21
cggaattctt aattaagtta acatcatcaa taatatacc                           39

<210> SEQ ID NO 22
<211> LENGTH: 66
<212> TYPE: DNA
<213> ORGANISM: Artificial Sequence
<220> FEATURE:
<221> NAME/KEY: primer_bind
<222> LOCATION: (1)..(66)
<223> OTHER INFORMATION: /Note="primer ITR-pIX"
<220> FEATURE:
<223> OTHER INFORMATION: Description of Artificial Sequence: primer

<400> SEQUENCE: 22
acggcgcgcc ttaagccacg cccacacatt tcagtacgta ctagtctacg tcacccgccc    60
cgttcc                                                               66

<210> SEQ ID NO 23
<211> LENGTH: 26
<212> TYPE: DNA
<213> ORGANISM: Artificial Sequence
<220> FEATURE:
<221> NAME/KEY: primer_bind
<222> LOCATION: (1)..(26)
<223> OTHER INFORMATION: /Note="primer Ad3'/Forw"
<220> FEATURE:
<223> OTHER INFORMATION: Description of Artificial Sequence: primer

<400> SEQUENCE: 23
cggaattcat caggataggg cggtgg                                         26

<210> SEQ ID NO 24
<211> LENGTH: 44
<212> TYPE: DNA
<213> ORGANISM: Artificial Sequence
<220> FEATURE:
<221> NAME/KEY: primer_bind
<222> LOCATION: (1)..(44)
<223> OTHER INFORMATION: /Note="primer Ad3'/Rev"
<220> FEATURE:
<223> OTHER INFORMATION: Description of Artificial Sequence: primer

<400> SEQUENCE: 24
```

```
cgggatccta tcgatattta aatgttttag ggcggagtaa cttg          44
```

```
<210> SEQ ID NO 25
<211> LENGTH: 37
<212> TYPE: DNA
<213> ORGANISM: Artificial Sequence
<220> FEATURE:
<221> NAME/KEY: primer_bind
<222> LOCATION: (1)..(37)
<223> OTHER INFORMATION: /Note="primer PA-pIX1"
<220> FEATURE:
<223> OTHER INFORMATION: Description of Artificial Sequence: primer

<400> SEQUENCE: 25
taagccacta gtacgtactg aaatgtgtgg gcgtggc                  37
```

```
<210> SEQ ID NO 26
<211> LENGTH: 43
<212> TYPE: DNA
<213> ORGANISM: Artificial Sequence
<220> FEATURE:
<221> NAME/KEY: primer_bind
<222> LOCATION: (1)..(43)
<223> OTHER INFORMATION: /Note="primer PA-pIX2"
<220> FEATURE:
<223> OTHER INFORMATION: Description of Artificial Sequence: primer

<400> SEQUENCE: 26
ttaagccacg cccacacatt tcagtacgta ctagtggctt aat           43
```

```
<210> SEQ ID NO 27
<211> LENGTH: 21
<212> TYPE: DNA
<213> ORGANISM: Artificial Sequence
<220> FEATURE:
<221> NAME/KEY: primer_bind
<222> LOCATION: (1)..(21)
<223> OTHER INFORMATION: /Note="primer Ea-1"
<220> FEATURE:
<223> OTHER INFORMATION: Description of Artificial Sequence: primer

<400> SEQUENCE: 27
cgtgtagtgt atttataccc g                                   21
```

```
<210> SEQ ID NO 28
<211> LENGTH: 21
<212> TYPE: DNA
<213> ORGANISM: Artificial Sequence
<220> FEATURE:
<221> NAME/KEY: primer_bind
<222> LOCATION: (1)..(21)
<223> OTHER INFORMATION: /Note="primer Ea-2"
<220> FEATURE:
<223> OTHER INFORMATION: Description of Artificial Sequence: primer

<400> SEQUENCE: 28
tcgtcactgg gtggaaagcc a                                   21
```

```
<210> SEQ ID NO 29
<211> LENGTH: 21
<212> TYPE: DNA
<213> ORGANISM: Artificial Sequence
<220> FEATURE:
<221> NAME/KEY: primer_bind
<222> LOCATION: (1)..(21)
<223> OTHER INFORMATION: /Note="primer Ea-3"
<220> FEATURE:
<223> OTHER INFORMATION: Description of Artificial Sequence: primer

<400> SEQUENCE: 29
```
tacccgccgt cctaaaatgg c                                           21

<210> SEQ ID NO 30
<211> LENGTH: 20
<212> TYPE: DNA
<213> ORGANISM: Artificial Sequence
<220> FEATURE:
<221> NAME/KEY: primer_bind
<222> LOCATION: (1)..(20)
<223> OTHER INFORMATION: /Note="primer Ea-5"
<220> FEATURE:
<223> OTHER INFORMATION: Description of Artificial Sequence: primer

<400> SEQUENCE: 30
tggacttgag ctgtaaacgc                                             20

<210> SEQ ID NO 31
<211> LENGTH: 21
<212> TYPE: DNA
<213> ORGANISM: Artificial Sequence
<220> FEATURE:
<221> NAME/KEY: primer_bind
<222> LOCATION: (1)..(21)
<223> OTHER INFORMATION: /Note="primer Ep-2"
<220> FEATURE:
<223> OTHER INFORMATION: Description of Artificial Sequence: primer

<400> SEQUENCE: 31
gcctccatgg aggtcagatg t                                           21

<210> SEQ ID NO 32
<211> LENGTH: 20
<212> TYPE: DNA
<213> ORGANISM: Artificial Sequence
<220> FEATURE:
<221> NAME/KEY: primer_bind
<222> LOCATION: (1)..(20)
<223> OTHER INFORMATION: /Note="primer Eb-1"
<220> FEATURE:
<223> OTHER INFORMATION: Description of Artificial Sequence: primer

<400> SEQUENCE: 32
gcttgagccc gagacatgtc                                             20

<210> SEQ ID NO 33
<211> LENGTH: 24
<212> TYPE: DNA
<213> ORGANISM: Artificial Sequence
<220> FEATURE:
<221> NAME/KEY: primer_bind
<222> LOCATION: (1)..(24)
<223> OTHER INFORMATION: /Note="primer Eb-2"
<220> FEATURE:
<223> OTHER INFORMATION: Description of Artificial Sequence: primer

<400> SEQUENCE: 33
cccctcgagc tcaatctgta tctt                                        24

<210> SEQ ID NO 34
<211> LENGTH: 27
<212> TYPE: DNA
<213> ORGANISM: Artificial Sequence
<220> FEATURE:
<221> NAME/KEY: primer_bind
<222> LOCATION: (1)..(27)
<223> OTHER INFORMATION: /Note="primer SV40-1"
<220> FEATURE:
<223> OTHER INFORMATION: Description of Artificial Sequence: primer -continued

```
<400> SEQUENCE: 34
gggggatccg aacttgttta ttgcagc                                          27

<210> SEQ ID NO 35
<211> LENGTH: 25
<212> TYPE: DNA
<213> ORGANISM: Artificial Sequence
<220> FEATURE:
<221> NAME/KEY: primer_bind
<222> LOCATION: (1)..(25)
<223> OTHER INFORMATION: /Note="primer SV40-2"
<220> FEATURE:
<223> OTHER INFORMATION: Description of Artificial Sequence: primer

<400> SEQUENCE: 35
gggagatcta gacatgataa gatac                                            25

<210> SEQ ID NO 36
<211> LENGTH: 27
<212> TYPE: DNA
<213> ORGANISM: Artificial Sequence
<220> FEATURE:
<221> NAME/KEY: primer_bind
<222> LOCATION: (1)..(27)
<223> OTHER INFORMATION: /Note="primer Ad5-1"
<220> FEATURE:
<223> OTHER INFORMATION: Description of Artificial Sequence: primer

<400> SEQUENCE: 36
gggagatctg tactgaaatg tgtgggc                                          27

<210> SEQ ID NO 37
<211> LENGTH: 24
<212> TYPE: DNA
<213> ORGANISM: Artificial Sequence
<220> FEATURE:
<221> NAME/KEY: primer_bind
<222> LOCATION: (1)..(24)
<223> OTHER INFORMATION: /Note="primer Ad5-2"
<220> FEATURE:
<223> OTHER INFORMATION: Description of Artificial Sequence: primer

<400> SEQUENCE: 37
ggaggctgca gtctccaacg gcgt                                             24

<210> SEQ ID NO 38
<211> LENGTH: 27
<212> TYPE: DNA
<213> ORGANISM: Artificial Sequence
<220> FEATURE:
<221> NAME/KEY: primer_bind
<222> LOCATION: (1)..(27)
<223> OTHER INFORMATION: /Note="primer ITR1"
<220> FEATURE:
<223> OTHER INFORMATION: Description of Artificial Sequence: primer

<400> SEQUENCE: 38
gggggatcct caaatcgtca cttccgt                                          27

<210> SEQ ID NO 39
<211> LENGTH: 27
<212> TYPE: DNA
<213> ORGANISM: Artificial Sequence
<220> FEATURE:
<221> NAME/KEY: primer_bind
<222> LOCATION: (1)..(27)
<223> OTHER INFORMATION: /Note="primer ITR2"
<220> FEATURE:
<223> OTHER INFORMATION: Description of Artificial Sequence: primer
```

<400> SEQUENCE: 39
ggggtctaga catcatcaat aatatac                                    27

<210> SEQ ID NO 40
<211> LENGTH: 32
<212> TYPE: DNA
<213> ORGANISM: Artificial Sequence
<220> FEATURE:
<221> NAME/KEY: primer_bind
<222> LOCATION: (1)..(32)
<223> OTHER INFORMATION: /Note="primer PCR/MLP1"
<220> FEATURE:
<223> OTHER INFORMATION: Description of Artificial Sequence: primer

<400> SEQUENCE: 40
ggcgaattcg tcgacatcat caataatata cc                              32

<210> SEQ ID NO 41
<211> LENGTH: 32
<212> TYPE: DNA
<213> ORGANISM: Artificial Sequence
<220> FEATURE:
<221> NAME/KEY: primer_bind
<222> LOCATION: (1)..(32)
<223> OTHER INFORMATION: /Note="primer PCR/MLP2"
<220> FEATURE:
<223> OTHER INFORMATION: Description of Artificial Sequence: primer

<400> SEQUENCE: 41
ggcgaattcg gtaccatcat caataatata cc                              32

<210> SEQ ID NO 42
<211> LENGTH: 17
<212> TYPE: DNA
<213> ORGANISM: Artificial Sequence
<220> FEATURE:
<221> NAME/KEY: primer_bind
<222> LOCATION: (1)..(17)
<223> OTHER INFORMATION: /Note="primer PCR/MLP3"
<220> FEATURE:
<223> OTHER INFORMATION: Description of Artificial Sequence: primer

<400> SEQUENCE: 42
ctgtgtacac cggcgca                                               17

<210> SEQ ID NO 43
<211> LENGTH: 49
<212> TYPE: DNA
<213> ORGANISM: Artificial Sequence
<220> FEATURE:
<221> NAME/KEY: primer_bind
<222> LOCATION: (1)..(49)
<223> OTHER INFORMATION: /Note="primer HP/asp1"
<220> FEATURE:
<223> OTHER INFORMATION: Description of Artificial Sequence: primer

<400> SEQUENCE: 43
gtacactgac ctagtgccgc ccgggaaagc ccgggcggca ctaggtcag             49

<210> SEQ ID NO 44
<211> LENGTH: 50
<212> TYPE: DNA
<213> ORGANISM: Artificial Sequence
<220> FEATURE:
<221> NAME/KEY: primer_bind
<222> LOCATION: (1)..(50)
<223> OTHER INFORMATION: /Note="primer HP/asp2"
<220> FEATURE:

```
<223> OTHER INFORMATION: Description of Artificial Sequence: primer

<400> SEQUENCE: 44
gtacctgacc tagtgccgcc cgggctttgc ccgggcggca ctaggtcagt           50

<210> SEQ ID NO 45
<211> LENGTH: 55
<212> TYPE: DNA
<213> ORGANISM: Artificial Sequence
<220> FEATURE:
<221> NAME/KEY: primer_bind
<222> LOCATION: (1)..(55)
<223> OTHER INFORMATION: /Note="primer HP/cla1"
<220> FEATURE:
<223> OTHER INFORMATION: Description of Artificial Sequence: primer

<400> SEQUENCE: 45
gtacattgac ctagtgccgc ccgggcaaag cccgggcggc actaggtcaa tcgat     55

<210> SEQ ID NO 46
<211> LENGTH: 54
<212> TYPE: DNA
<213> ORGANISM: Artificial Sequence
<220> FEATURE:
<221> NAME/KEY: primer_bind
<222> LOCATION: (1)..(54)
<223> OTHER INFORMATION: /Note="primer HP/cla2"
<220> FEATURE:
<223> OTHER INFORMATION: Description of Artificial Sequence: primer

<400> SEQUENCE: 46
gtacatcgat tgacctagtg ccgcccgggt ttgcccgggc ggcactaggt caat      54

<210> SEQ ID NO 47
<211> LENGTH: 45
<212> TYPE: DNA
<213> ORGANISM: Artificial Sequence
<220> FEATURE:
<221> NAME/KEY: misc_feature
<222> LOCATION: (1)..(45)
<223> OTHER INFORMATION: /Note="hac, haw Potential hairpin that can be
      formed after digestion with restriction
      endonuclease Asp7I8 in both the correct and in the
      reverse orientation, respectively"
<220> FEATURE:
<223> OTHER INFORMATION: Description of Artificial Sequence:synthetic
      DNA sequence

<400> SEQUENCE: 47
gtacactgac ctagtgccgc ccgggcaaag cccgggcggc actag               45
```

What is claimed is:

1. A recombinant adenovirus wherein the E3-gp19K coding region is replaced by a transgene, wherein any remaining E3 coding regions are intact, which transgene does not comprise a heterologous promoter and which transgene is under transcriptional control of the adenovirus E3 promoter.

2. A plasmid comprising an adenovirus E3 region wherein the E3-gp19K coding region is replaced by a transgene, wherein the remaining E3 coding regions are intact, which transgene does not comprise a heterologous promoter and which transgene is under transcriptional control of the adenovirus E3 promoter.

* * * * *

UNITED STATES PATENT AND TRADEMARK OFFICE
CERTIFICATE OF CORRECTION

Figure 3A:
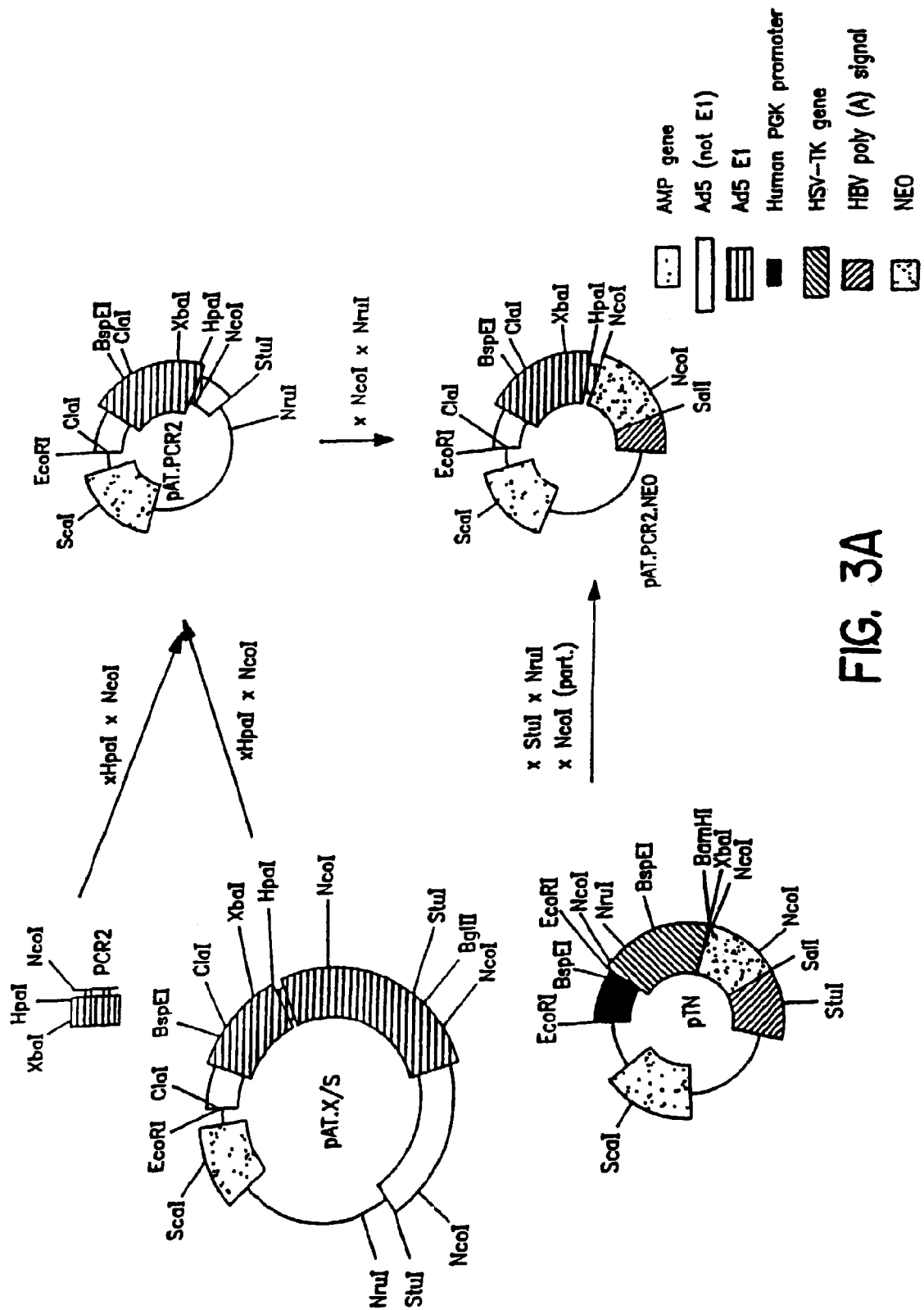
FIG. 3A–B depict construction of pIG.E1A.NEO. pIG.E1A.NEO encodes Ad5 nucleotides 459–1713 operatively linked to the human PGK promoter. Also encoded is the E1B promoter functionally linked to the neomycin resistance gene (Neo$^R$) and the hepatitis B virus (HBV) poly(A) signal. In this construct, the AUG codon of the E1B 21 kDa protein functions as the initiation codon of Neo$^R$. To construct this plasmid, the E1B promoter and initiation codon (ATG) of the E1B 21 kDa protein were PCR amplified with primers Ea-3 and Ep-2, where Ep-2 introduces an Nco I site (5'-CCATGG) at the 21 kDa protein initiation codon. The PCR product (PCRII) was digested with HpaI and NcoI and ligated into the corresponding sites of pAT-X/S, producing pAT-X/S-PCR2. The Nco I-Stu I fragment of pTN, containing the Neo$^R$ and a portion of the HBV poly(A) site were ligated into the Nco I-Nru I sites of pAT-X/S-PCR2, producing pAT-PCR2-NEO. The HBV poly(A) signal was completed by replacing the Sca I-Sal I fragment of pAT-PCR2-NEO with the corresponding fragment of pTN, producing pAT.PCR2.NEO.p(A), and replacing the Sca I-Xba I fragment of pAT.PCR2.NEO.p(A) with the corresponding fragment of pIG.E1A.E1B.X, producing pIG.E1A.NEO.
Figure 3B:
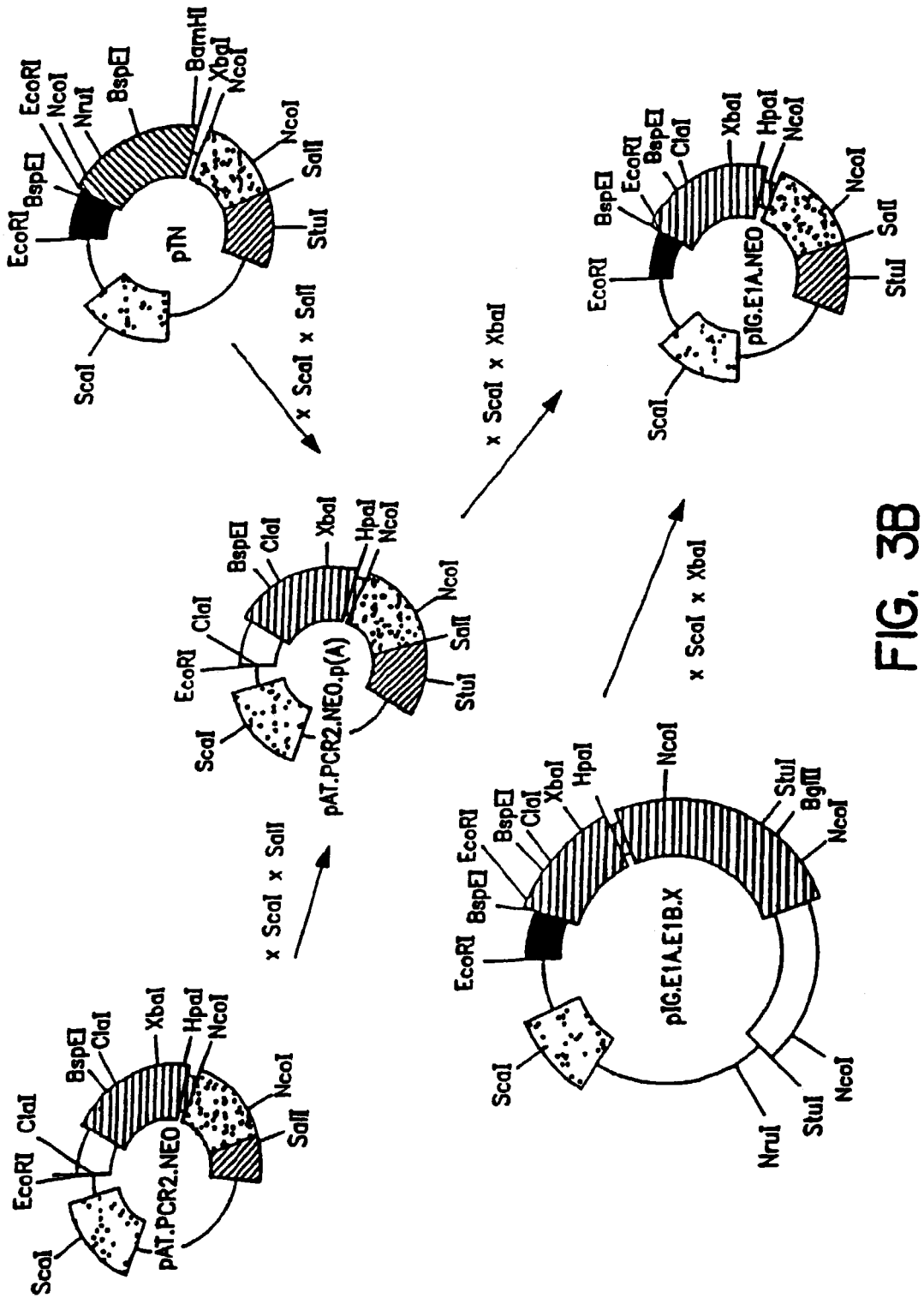

PATENT NO. : 7,037,716 B2
APPLICATION NO. : 10/396548
DATED : May 2, 2006
INVENTOR(S) : Ronald Vogels and Abraham Bout It is certified that error appears in the above-identified patent and that said Letters Patent is hereby corrected as shown below:

In the specification:

| | | |
|---|---|---|
| COLUMN 2, | LINE 26, | change "(19.86)" to --(1986)-- |
| COLUMN 3, | LINE 6, | change "phenotypes area" to --phenotypes are a-- |
| COLUMN 7, | LINE 42, | change "FIG. 3A-B depict" to --FIGS. 3A-B depict-- |
| COLUMN 7, | LINE 46, | change "(NEO$^R$)" to --(NEO$^R$)-- |
| COLUMN 7, | LINE 48, | change "NEO$^R$." to --NEO$^R$.-- |
| COLUMN 7, | LINE 56, | change "NEO$^R$" to --NEO$^R$-- |
| COLUMN 8, | LINE 9, | change "NEO$^R$" to --NEO$^R$-- |
| COLUMN 8, | LINE 12, | change "NEO$^R$" to --NEO$^R$-- |
| COLUMN 8, | LINE 50, | change "pIG.E1A.E IB." to --pIG.E1A.E1B.-- |
| COLUMN 11, | LINE 33, | change "ts 125 mutation:" to --ts125 mutation:-- |
| COLUMN 12, | LINE 22, | change "7:21;5-222)." to --7:215-222).-- |
| COLUMN 12, | LINE 37, | change "E1 A." to --E1A.-- |
| COLUMN 12, | LINE 65, | change "express. E1A" to --express E1A-- |
| COLUMN 12, | LINE 67, | change "E1 -defective" to --E1-defective-- |
| COLUMN 18, | LINE 27, | change "E1B+ hrE2A;" to --E1B+hrE2A;-- |
| COLUMN 19, | LINE 8, | change "well, known" to --well known-- |
| COLUMN 21, | LINE 8, | change "E1 -deleted" to --E1-deleted-- |
| COLUMN 21, | LINE 27, | change "NEO$^R$" to --NEO$^R$-- |
| COLUMN 22, | LINE 15, | change "NEO$^R$," to --NEO$^R$,-- |
| COLUMN 22, | LINE 45, | change "BIII/NruI" to --B1II/NruI-- |
| COLUMN 23, | LINE 64, | change "of6-day old" to --of 6-day old-- |
| COLUMN 25, | LINE 42, | change "inhibitor,50 mM" to --inhibitor, 50 mM-- |
| COLUMN 26, | LINE 11, | change "Ad5-E1 -transformed" to --Ad5-E1-transformed-- |
| COLUMN 26, | LINE 43, | change "PIG.E1A.NEO" to --pIG.E1A.NEO-- |
| COLUMN 26, | LINE 65, | change "HindI1I," to --HindIII,-- |
| COLUMN 27, | LINE 7, | change "C9,we" to --C9, we-- |
| COLUMN 27, | LINE 33, | change "911 ,PER.C3," to --911, PER.C3,-- |

UNITED STATES PATENT AND TRADEMARK OFFICE
CERTIFICATE OF CORRECTION

PATENT NO. : 7,037,716 B2
APPLICATION NO. : 10/396548
DATED : May 2, 2006
INVENTOR(S) : Ronald Vogels and Abraham Bout It is certified that error appears in the above-identified patent and that said Letters Patent is hereby corrected as shown below:

In the specification (continued):

| | | |
|---|---|---|
| COLUMN 27, | LINE 37, | change "celllines." to --cell lines.-- |
| COLUMN 27, | LINE 46, | change "3328.As" to --3328. As-- |
| COLUMN 28, | LINE 31, | change "is. expected" to --is expected-- |
| COLUMN 31, | LINE 9, | change "Pact" to --PacI-- |
| COLUMN 31, | LINE 36, | change "with. BamHI" to --with BamHI-- |
| COLUMN 32, | LINE 16, | change "wildtype" to --wild-type-- |
| COLUMN 33, | LINE 32, | change "adenovirus. genome" to --adenovirus genome-- |
| COLUMN 34, | LINE 42, | change "(HindIII)" to --(HindIII)-- |
| COLUMN 35, | LINE 8, | change "HindI1I-" to --HindIII- -- |
| COLUMN 35, | LINE 64, | change "(2,µg)." to --(2 µg).-- |
| COLUMN 36, | LINE 57, | change "CMV-driven. luciferase gene" to --CMV-driven luciferase gene-- |
| COLUMN 37, | LINE 34, | change "sgrAI" to --SgrAI-- |
| COLUMN 38, | LINE 54, | change "SV40-derivedpolyadenylation" to --SV40-derived poly-adenylation-- |
| COLUMN 39, | LINE 18, | change "control" to --control:-- |
| COLUMN 39, | LINE 44, | change "5'ITR" to --5' ITR-- |
| COLUMN 40, | LINE 10, | change "DNA.(namely," to --DNA (namely,-- |
| COLUMN 42, | LINE 37, | change "fibroblasts.," to --fibroblasts.-- |
| COLUMN 44, | LINE 47, | change "resulting cone" to --resulting clone-- |
| COLUMN 45, | LINE 10, | change "SV40.A" to --SV40. A-- |
| COLUMN 45, | LINE 61, | change "MboI.digested" to --MboI digested-- |

UNITED STATES PATENT AND TRADEMARK OFFICE
CERTIFICATE OF CORRECTION

PATENT NO. : 7,037,716 B2
APPLICATION NO. : 10/396548
DATED : May 2, 2006
INVENTOR(S) : Ronald Vogels and Abraham Bout It is certified that error appears in the above-identified patent and that said Letters Patent is hereby corrected as shown below:

In the claims:
CLAIM 2, COLUMN 66, LINE 54, change "wherein the remaining" to --wherein any remaining--

Signed and Sealed this

Twenty-second Day of January, 2008

JON W. DUDAS
*Director of the United States Patent and Trademark Office*